United States Patent
Kawamoto et al.

(10) Patent No.: US 7,858,800 B2
(45) Date of Patent: Dec. 28, 2010

(54) BIARYL DERIVATIVES

(75) Inventors: Hiroshi Kawamoto, Tsuchiura (JP); Satoru Ito, Tsukuba (JP); Atsushi Satoh, Tsukuba (JP); Yasushi Nagatomi, Tsukuba (JP); Yukari Hirata, Tsukuba (JP); Toshifumi Kimura, Tsukuba (JP); Gentaroh Suzuki, Tsukuba (JP); Akio Sato, Ushiku (JP); Hisashi Ohta, Tsukuba (JP)

(73) Assignee: Banyu Pharmaceutical Co., Ltd., Kudankita, Chiyoda-Ku, Tokyo (JP)

( * ) Notice: Subject to any disclaimer, the term of this patent is extended or adjusted under 35 U.S.C. 154(b) by 965 days.

(21) Appl. No.: 11/629,730

(22) PCT Filed: Jun. 29, 2005

(86) PCT No.: PCT/JP2005/012442

§ 371 (c)(1),
(2), (4) Date: Dec. 15, 2006

(87) PCT Pub. No.: WO2006/004142

PCT Pub. Date: Jan. 12, 2006

(65) Prior Publication Data

US 2007/0191389 A1    Aug. 16, 2007

(30) Foreign Application Priority Data

Jun. 30, 2004    (JP) ............... 2004-194410

(51) Int. Cl.
C07D 401/00    (2006.01)
A61K 31/44    (2006.01)
(52) U.S. Cl. ..................... 546/256; 514/340
(58) Field of Classification Search ............ 546/256; 514/340
See application file for complete search history.

(56) References Cited

U.S. PATENT DOCUMENTS

| 6,090,825 | A | 7/2000 | Andrews et al. |
| 2003/0055085 | A1 | 3/2003 | Wagenen et al. |
| 2003/0114465 | A1 | 6/2003 | Stamford et al. |
| 2004/0127521 | A1 | 7/2004 | Cai et al. |
| 2004/0132726 | A1 | 7/2004 | Arora et al. |
| 2008/0280889 | A1 | 11/2008 | Bilodeau et al. |

FOREIGN PATENT DOCUMENTS

| WO | WO 00/39125 | 7/2000 |
| WO | WO00/63204 | 10/2000 |
| WO | WO 02/008417 | 9/2002 |
| WO | WO03/051797 | 6/2003 |
| WO | WO 2005/061489 | * 7/2005 |
| WO | WO2005100344 | 10/2005 |

OTHER PUBLICATIONS

Supplementary European Search ReportC for EP Appl'n No. 05758117.5 (Nov. 26, 2009).

* cited by examiner

*Primary Examiner*—Rita J Desai
*Assistant Examiner*—John Mabry
(74) *Attorney, Agent, or Firm*—J. Eric Thies; Gerard M. Devlin

(57) ABSTRACT

The present invention relates to a compound represented by the formula (I):

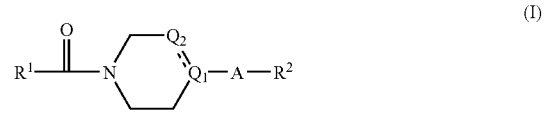

or a pharmaceutically acceptable salt thereof, wherein:

$R^1$ is a linear or branched alkoxy group, a cycloalkoxy group, a linear or branched lower alkyl group, etc.; $R^2$ is halogen atom, a lower alkyl group, etc.; $Q^1$ is carbon atom or nitrogen atom; $Q^2$ is carbon atom which may be substituted with oxo group; the formula (III):

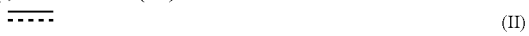

(II)

is a single bond or a double bond; A is a group selected from the group consisting of the substitutent group α; and $R^5$ is hydrogen atom, a lower alkyl group, cyano group, an alkoxy group or a trialkylsilyl group; having an mGluR1 inhibiting action and being useful as treatment and/or prevention of convulsion, acute pain, cerebral disturbance such as cerebral infarction or transient cerebral ischemia onset, anxiety, chemical dependency or Parkinson's disease.

8 Claims, No Drawings

BIARYL DERIVATIVES

CROSS REFERENCE TO RELATED APPLICATIONS

This application is a U.S. National Phase application under 35 U.S.C. §371 of PCT Application No. PCT/JP2005/012442, filed Jun. 29, 2005, which claims priority under 35 U.S.C. §119 from JP Application No. JP2004-194410, filed Jun. 30, 2004.

TECHNICAL FIELD

The present invention relates to biaryl derivatives.

BACKGROUND ART

Glutamic acid is a neurotransmitter which mediates an excitatory transmittance in a central nervous system. In addition to various neurotransmitting actions, glutamic acid participates in many important brain functions such as existence and death as well as differentiation and proliferation of nerve cells, development and maturation of nerve and glia cells and plastic change of neurotransmitting efficiency of developed brain (refer, for example, to *Annual Review of Biophysics and Biomolecular Structure*, volume 23, page 319 (1994)).

According to pharmacological and molecular biological studies, glutamic acid receptors in central nervous system of mammals are classified into two groups which are glutamic acid receptor of an ion channel type and metabotropic glutamic acid receptor (hereinafter, it will be referred to as "mGluR"). Glutamic acid receptor of an ion channel type comprises a complex of different subunit proteins and is an ion channel which is opened and closed by binding of ligand. On the other hand, mGluR is conjugated to GTP-binding protein and shows an action by regulating the activity of ion channel or the production of intracellular second messenger via GTP-binding protein (refer, for example, to *Brain Research Reviews*, volume 26, page 230 (1998)).

According to the result of studies up to now, mGluR has been reported to be present as eight different kinds of subtypes of mGluR1 to 8. They are classified into three subgroups depending upon homology of amino acid sequence, signal transmission and pharmacological characteristics. With regard to intracellular signal transmission, the group I (mGluR1 and 5) activates phospholipase C and the group II (mGluR2 and 3) and the group III (mGluR 4, 6, 7 and 8) regulate the adenylate cyclase activity whereby they suppress the accumulation of cyclic adenosine monophosphate (cAMP) by stimulation with forskolin. The group II is also selectively activated by LY 354740 mentioned, for example, in *Journal of Medicinal Chemistry*, volume 42, page 1027 (1999) while the group III is selectively activated by L-AP4. Further, various kinds of receptors are expressed in a broad range of cerebral and nervous system except mGluR6 specifically existing in the retina and, moreover, each of them shows a characteristic distribution in the brain whereby each receptor has been believed to play different physiological role (refer, for example, to *Neurochemistry International*, volume 24, page 439 (1994) and *European Journal of Pharmacology*, volume 375, page 277 (1999)).

With regard to a compound which is similar to the compound concerning the present invention, a compound represented, for example, by the formula (A) is mentioned (refer to Patent Document 1).

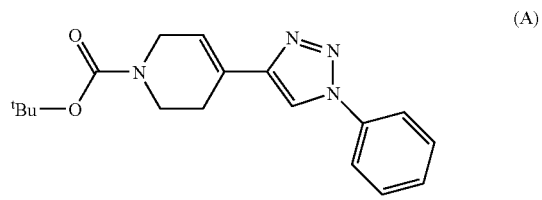

(A)

The use of the compounds concerning the invention mentioned in Patent Document 1 is treatment and prevention of schizophrenia and Parkinson's disease but the compound represented by the above-mentioned formula (A) is an intermediate for the production of the compounds concerning the invention mentioned in Patent Document 1 and there is neither description nor suggestion therein that the compound represented by the formula (A) is useful as treatment and prevention for any disease.

DISCLOSURE OF THE INVENTION

Under such circumstances, an object of the present invention is to provide a novel substance having an inhibitory action on mGluR1.

The present inventors have found that specific diaryl substituted five-membered heterocyclic derivatives have an inhibitory action on mGluR1 and accomplished the present invention.

Thus, in order to achieve the above object, the present invention provides the compounds mentioned in the following (1) to (7) and pharmaceutically acceptable salt thereof.

(1) A compound represented by the formula (I):

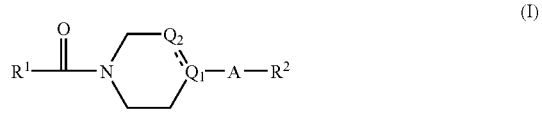

(I)

or a pharmaceutically acceptable salt thereof, wherein:
$R^1$ is
(A) a linear or branched alkoxy group, a cycloalkoxy group or a linear or branched lower alkyl group, or (B) a formula (II):

(II)

wherein:
$R^3$ and $R^4$ each independently is hydrogen atom, a linear or branched lower alkyl group or a cycloalkyl group or $R^3$, $R^4$ and nitrogen atom in the formula (II) together form a four- to seven-membered nitrogen-containing aliphatic heterocyclic group;

said heterocyclic group may have one oxygen atom as a constituting atom of the ring;

$R^2$ is phenyl group or a five- to six-membered unsaturated or partially unsaturated heterocyclic group having 1 to 3 hetero atom(s) in a ring selected from the group consisting of nitrogen atom, sulfur atom and oxygen atom, which may have one to three substitutent(s) in a ring selected from the group consisting of halogen atom, a lower alkyl group, cyano group, nitro group, an alkoxy group, a lower alkylsulfonyl group, oxo group and hydroxyl group;

$Q_1$ is carbon atom or nitrogen atom;

$Q_2$ is carbon atom which may be substituted with oxo group;

the formula (III):

- - - - - - - - (II)

is a single bond or a double bond;

A is a group selected from the group consisting of the substitutent group α;

$R^5$ is hydrogen atom, a lower alkyl group, cyano group, alkoxy group or trialkylsilyl group;

said lower alkyl group may be substituted with an alkoxy group; and except the case where A is a group represented by any of the formula (IV):

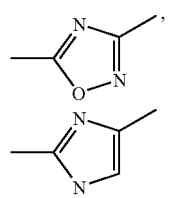 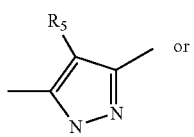 (IV)

and the formula (V):

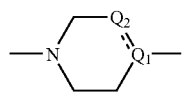 (V)

in the above formula (I) is a group represented by the formula (V-1):

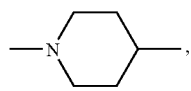 (V-1)

where A is a group represented by the formula (IV-1):

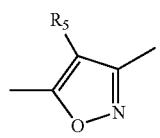

$R^5$ is the same as that defined already) and the above formula (V) is a group represented by the formula (V-2):

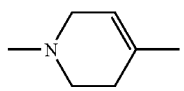 (V-2)

or where A is a group represented by any of the formula (IV-3):

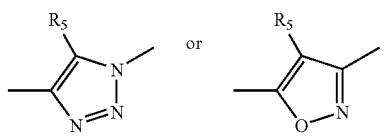 (IV-3)

the above formula (V) is the formula (V-3):

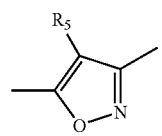 (V-3)

and the above $R^2$ is an unsubstituted phenyl group.

Substituent group α:

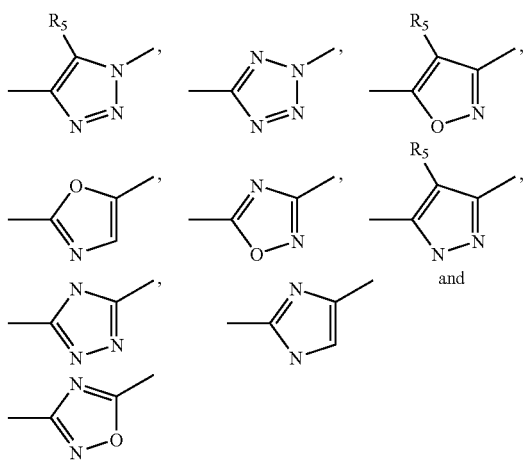

(2) A compound represented by the formula (I):

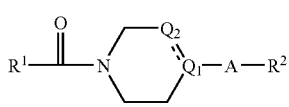 (I)

or a pharmaceutically acceptable salt thereof, wherein:

$R^1$ is (1) a linear or branched alkoxy group, a cycloalkoxy group or a lower alkyl group, or (2) the formula (II):

(II)

wherein:

R³ and R⁴ each independently is a linear or branched lower alkyl group or a cycloalkyl group or R³, R⁴ and nitrogen atom in the formula (II) together form a four- to seven-membered nitrogen-containing aliphatic heterocyclic group;

said heterocyclic group may have one oxygen atom as a constituting atom of the ring;

R² is phenyl group or a five- to six-membered unsaturated or partially unsaturated heterocyclic group having 1 to 3 hetero atom(s) in a ring selected from the group consisting of nitrogen atom, sulfur atom and oxygen atom, which may have one to three substitutent(s) in a ring selected from the group consisting of halogen atom, a lower alkyl group, cyano group, nitro group, an alkoxy group, a lower alkylsulfonyl group, oxo group and hydroxyl group;

$Q_1$ is carbon atom or nitrogen atom;

$Q_2$ is carbon atom which may be substituted with oxo group;

the formula (III):

--------  (III)

is a single bond or a double bond;

A is a group represented by any of the formula (IV-4):

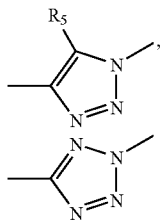
(IV-4)

wherein:

R⁵ is hydrogen atom, a lower alkyl group, cyano group, an alkoxy group or a trialkylsilyl group;

said lower alkyl group may be substituted with an alkoxy group; and except the compound where the above (1) is represented by the formula (I-1):

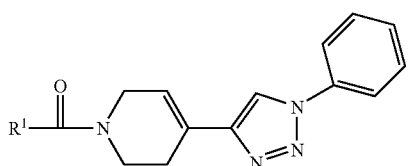
(I-1)

wherein:

R¹ is the same as that defined already.

(3) The compound according to the above (2), or a pharmaceutically acceptable salt thereof, wherein R¹ is a group represented by the formula (II):

(II)

wherein:
each symbol has the same as that defined already.

(4) The compound according to the above (2) or (3), or a pharmaceutically acceptable salt thereof,
wherein A is any group represented by the formula (IV-5):

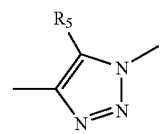 or 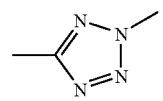
(IV-5)

wherein:
R⁵ is the same as that defined already.

(5) The compound according to any one of above (1) to (4), or a pharmaceutically acceptable salt thereof, wherein the formula (V) is any group represented by the formula (V-4):

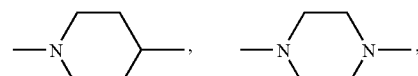
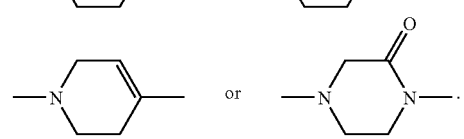
(V-4)

(6) The compound according to any one of the above (1) to (4), or a pharmaceutically acceptable salt thereof, wherein the formula (V) is any group represented by the formula (V-5):

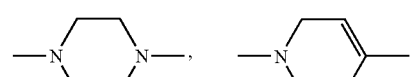
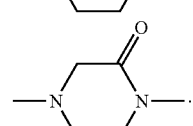
(V-5)

(7) The compound according to claim 1, wherein the compound represented by the formula (I) is isopropyl 4-[1-(2-fluoropyridin-3-yl)-5-methyl-1H-[1,2,3]triazol-4-yl]-1,2,3,6-tetrahydropyridine-1-carboxylate, 4-[1-(2-fluoropyridin-3-yl)-5-methyl-1H-[1,2,3]triazol-4-yl]-1,2,3,6-tetrahydropyridine-1-carboxylic acid pyrrolidineamide, 4-[1-(2-fluoropyridin-3-yl)-5-methyl-1H-[1,2,3]triazol-4-yl]-1,2,3,6-tetrahydropyridine-1-carboxylic acid diethylamide, 4-[1-(2-fluoropyridin-3-yl)-5-methyl-1H-[1,2,3]triazol-4-yl]-1,2,3,6-tetrahydropyridine-1-carboxylic acid piperidineamide, isopropyl 4-[1-(2-chlorophenyl)-5-methyl-1H-[1,2,3]triazol-4-yl]-1,2,3,6-tetrahydropyridine-1-carboxylate, 4-[1-(2-fluoropyridin-3-yl)-5-methyl-1H-[1,2,3]triazol-4-yl]-1,2,3,6-tetrahydropyridine-1-carboxylic acid isopropylmethylamide, 4-[1-(2-fluoropyridin-3-yl)-5-methyl-1H-[1,2,3]triazol-4-yl]-1,2,3,6-tetrahydropyridine-1-carboxylic acid tert-butylamide, isopropyl 4-[1-phenyl-5-methyl-1H-[1,2,3]triazole-4-yl]-1,2,3,6-tetrahydropyridine-1-carboxylate, isopropyl 4-[1-(2-chloropyridin-3-yl)-5-methyl-1H-[1,2,3]triazol-4-yl]-1,2,3,6-tetrahydropyridine-1-carboxylate, isopropyl 4-[1-(2-fluoropyridin-5-yl)-5-methyl-1H-[1,2,3]triazol-4-yl]-1,2,3,6-tetrahydropyridine-1-carboxylate, propyl 4-[1-(2-chloropyridin-3-yl)-5-methyl-1H-[1,2,3]triazol-4-yl(1,2,3,6-tetrahydropyridine-1-carboxylate, ethyl 4-[1-(2-chloropyridin-3-yl)-1H-[1,2,3]triazol-4-yl]-1,2,3,6-tetrahydropyridine-1-carboxylate, 2-methylpropyl 4-[1-(2-chloropyridin-3-yl)-5-methyl-1H-[1,2,3]triazol-4-yl]-1,2,3,6-tetrahydropyridine-1-carboxylate, isopropyl 4-[1-(pyridin-3-yl)-1H-[1,2,3]triazol-4-yl]-1,2,3,6-tetrahydropyridine-1-carboxylate, isopropyl 4-[5-cyano-1-phenyl-1H-[1,2,3]triazol-4-yl]-1,2,3,6-tetrahydropyridine-carboxylate, {4-[1-(2-chloropyridin-3-yl)-5-methyl-1H-[1,2,3]triazole-4-yl]-1,2,3,6-tetrahydropyridine-1-carboxylic acid pyrrolidineamide, 4-[1-(2-fluoro-pyridin-3-yl)-1H-[1,2,3]triazol-4-yl]-1,2,3,6-tetrahydropyridine-1-carboxylic acid isopropylamide, 4-[1-(2-chloro-pyridin-3-yl)-1H-[1,2,3]triazol-4-yl]-1,2,3,6-tetrahydropyridine-1-carboxylic acid isopropylmethylamide, 4-[1-(2-chloropyridin-3-yl)-5-methyl-1H-[1,2,3]triazol-4-yl]-1,2,3,6-tetrahydropyridine-1-carboxylic acid piperidineamide, 4-[1-(2-chloropyridin-3-yl)-5-methyl-1H-[1,2,3]triazol-4-yl]-1,2,3,6-tetrahydropyridine-1-carboxylic acid methyl-tert-butylamide, 4-[1-(2-chloropyridin-3-yl)-1H-[1,2,3]triazol-4-yl]-1,2,3,6-tetrahydropyridine-1-carboxylic acid tert-butylamide, 1-{4-[1-(2-chloropyridin-3-yl)-1H-[1,2,3]triazol-4-yl]-1,2,3,6-tetrahydropyridin-1-yl}-3-methyl-1-butanone, isopropyl 4-[1-(2-fluoropyridin-3-yl)-1H-[1,2,3]triazol-4-yl]-1,2,3,6-tetrahydropyridine-1-carboxylate or isopropyl 4-[1-phenyl-5-propyl-1H-[1,2,3]triazol-4-yl]-1,2,3,6-tetra-hydropyridine-carboxylate or a pharmaceutically acceptable salt thereof.

The compounds of the above (1) to (7) or pharmaceutically acceptable salts thereof have an inhibitory action on mGluR1. Thus, the present invention provides an mGluR1 inhibitor comprising the compound mentioned in (1) to (7) or a pharmaceutically acceptable salt thereof.

It has been reported that, when 3,5-dihydroxyphenylglycine (hereinafter, referred to as DHPG) which is an agonist selective to the group I is administered into a ventricle, convulsion is generated (refer, for example, to *Journal of Neuroscience Research*, volume 51, page 339 (1998)).

On the other hand, in the test using an mGluR1-selective antagonist, it has been reported that, in addition to the fact that RS-1-aminoindan-1,5-dicarboxylic acid (hereinafter, it will be referred to as AIDA) shows a dose-dependent antispasmodic action in spasmodic models induced by pentylenetetrazole which has been commonly used for evaluation of action of antispasmodics (refer, for example, to *Neuropharmacology*, volume 37, page 1465 (1998)), it also shows a suppressive action on convulsion induced by sonic stimulation in mice and rats which genetically show convulsion easily (refer, for example, to *European Journal of Pharmacology*, volume 368, page 17 (1999)). It has been further reported that LY 456236 which is another selective antagonist lowers sustaining time of convulsion and degree thereof in amygdaloidal kindling rat which has been known as a model of human convulsion (refer, for example, to *Neuropharmacology*, volume 43, page 308 (2002)).

Those findings suggest that an mGluR1 inhibitor is useful for prevention or treatment of convulsion.

Accordingly, it is believed that the compounds mentioned in the above (1) to (7) having an mGluR1 inhibitory action or pharmaceutically acceptable salts thereof are effective for prevention or treatment of convulsion.

Further, when DHPG is administered into spinal cavity, an abnormal pain or an excessive pain by mechanical stimulation or an excessive pain by thermal stimulation is generated in rats (refer, for example, to *Neuroreport*, volume 9, page 1169 (1998)).

On the other hand, in investigations using antagonists, when AIDA is administered into brain, pain threshold rises (refer, for example, to *The Journal of Pharmacology & Experimental Therapeutics*, volume 281, page 721 (1997)) and, when AIDA is administered into spinal cavity, an analgesic action is noted in sustained pain models such as a pain-sensitive model by spinal code damage (refer, for example, to *Journal of Neurotrauma*, volume 19, page 23 (2002)) and an arthritis model (refer, for example, to *The Journal of Pharmacology & Experimental Therapeutics*, volume 300, page 149 (2002)).

Those findings suggest that an mGluR1 inhibitor has an analgesic action not only on acute pain but also on inflammatory pain and chronic pain.

Accordingly, it is believed that the compounds mentioned in the above (1) to (7) having an mGluR1 inhibitory action or pharmaceutically acceptable salts thereof are effective for prevention or treatment of acute pain, inflammatory pain or chronic pain.

In addition, in a suppressive action of AIDA on retarded nerve cell death of hippocampus noted in a transient whole cerebral ischemia-reperfusion model (refer, for example, to *Neuropharmacology*, volume 38, page 1607 (1999) and *Neuroscience Letters*, volume 293, page 1 (2000)), in a reducing action on volume of infarction of cerebral cortex in model of subdural bleeding of rats by (3aS,6aS)-6a-naphthalen-2-yl-methyl-5-methylidene-hexahydro-cyclopenta[c]furan-1-one (hereinafter, referred to as "BAY 36-7620") which is an mGluR1-selective antagonist (refer, for example, to *European Journal of Pharmacology*, volume 428, page 203 (2001)) and in R 128494 which is another selective antagonist, reduction of total volume of infarction in a model for ligation of cerebral artery of rat is noted (refer, for example, to *Neuropharmacology*, volume 43, page 295 (2002)).

Those findings suggest the possibility that an mGluR1 inhibitor has a protective action on cerebral disturbance such as cerebral infarction or transient cerebral ischemia onset.

Accordingly, it is believed that the compounds mentioned in the above (1) to (7) having an mGluR1 inhibitory action or pharmaceutically acceptable salts thereof are effective for prevention or treatment of cerebral disturbance such as cerebral infarction or transient cerebral ischemia onset.

Further, when DHPG is administered into cerebral nucleus accumbens, an increase in spontaneous movement is noted and its action is similar to that when a dopamine receptor stimulant is administered (refer, for example, to *European Journal of Neuroscience*, volume 13, page 2157 (2001)) and, furthermore, in *Psychopharmacology*, volume 141, page 405 (1999) for example, prepulse inhibition disorder noted in experimental animals models and in patients suffering from schizophrenia is generated when DHPG is administered into cerebral nucleus accumbens. All of those reactions resulted by DHPG are similar to the reactions noted in dopamine receptor stimulants such as apomorphine or dopamine-liberating drugs such as amphetamine and methamphetamine. On the other hand, it is believed that the already known antipsychotic agents express the action by suppression of an excessively excited dopamine nerve.

The fact that a reaction similar to a dopamine stimulating action is noted by DHPG suggests the participation of mGluR1 and mGluR5 in nucleus accumbens in pathergasia and it is suggested that an mGluR1 inhibitor has a possibility of improving such symptoms.

Accordingly, it is believed that the compounds mentioned in the above (1) to (7) having an mGluR1 inhibitory action or pharmaceutically acceptable salts thereof are effective for prevention or treatment of pathergasia such as schizophrenia.

Further, in a conflict test of a Vogel type using rats which has been commonly used as an evaluation system whereby an anti-anxiety action of a drug is able to be detected, there is a report that R 128494 which is a selective antagonist increases the drinking of water (refer, for example, to *Neuropharmacology*, volume 43, page 295 (2002)).

This finding suggests the possibility that mGluR1 inhibitor has an anti-anxiety action.

Accordingly, it is believed that the compounds mentioned in the above (1) to (7) having an mGluR1 inhibitory action or pharmaceutically acceptable salts thereof are effective for prevention or treatment of anxiety.

Further, in the previously-mentioned Non-Patent Document 16, there is a description that BAY 36-7620 which is an mGluR1-selective antagonist suppresses the intracerebral self-stimulation promoted by MK-801 which is an NMDA receptor antagonist. Since it has been clinically made clear that many of NMDA receptor antagonists result in anaclisis, this test system is believed to be a model which reflects a part of anaclisis by MK-801.

Those findings suggest the possibility that a selective antagonist to mGluR1 receptor is a preventive or treating agent for chemical dependency.

Accordingly, it is believed that the compounds mentioned in the above (1) to (7) having an mGluR1 inhibitory action or pharmaceutically acceptable salts thereof are effective for prevention or treatment of chemical dependency.

Further, in a test where extracellular potential is recorded using brain slices containing subthalamic nucleus of rats, it has been observed that general frequency of active potential increases by topical application of DHPG (refer, for example, to *Brain Research*, volume 766, page 162 (1997) and, therefore, it is suggested that activation of subthalamic nucleus is resulted by mGluR1 or mGluR5. It has been a well-known fact that excitation of subthalamic nucleus is a characteristic feature of Parkinson's disease.

Those findings suggest the possibility that an mGluR1 inhibitor is a preventive or treating agent for Parkinson's disease.

Accordingly, it is believed that the compounds mentioned in the above (1) to (7) having an mGluR1 inhibitory action or pharmaceutically acceptable salts thereof are effective for prevention or treatment of Parkinson's diseases.

Incidentally, reflux esophagitis (GERD) is the most common upper gastrointestinal disorder. An object by the current drug therapy is suppression of secretion of gastric acid or neutralization of gastric acid in the esophagus. It has been thought that main mechanism for back flow is due to a chronic decrease in tension of lower esophageal sphincter. However, according to the report of *Gastroenterol Clin. North Am.*, volume 19, pages 517 to 535 (1990) for example, it is shown that most of reflux episode is resulted by temporary lower esophageal sphincter relaxations (TLESRs) or, in other words, relaxations caused by other than swallowing. In addition, it has been also found that normal gastric acid secretion in patients suffering from GERD is normal.

Lower esophageal sphincter (LES) is apt to be relaxed intermittently. As a result, a mechanical barrier is temporarily lost during relaxation of sphincter and, therefore, gastric juice is able to flow into esophagus. Such a phenomenon is defined as "backflow".

A word "TLESR" meaning a temporary lower esophageal sphincter relaxation is a definition in accordance with *Gastroenterology*, volume 109(2), pages 601 to 610 (1995).

The term "backflow" is defined as a gastric juice which is flown from stomach into esophagus. The reason is that, under such a state, a mechanical barrier is temporarily lost. The word "GERD" meaning reflux esophagitis is a definition in accordance with *Bailliére's Clinical Gastroenterology*, volume 14, pages 759 to 774 (2000).

As a result of the above-mentioned physiological and pathophysiological meanings, it is believed that the compounds mentioned in the above (1) to (7) having an mGluR1 inhibitory action or pharmaceutically acceptable salts thereof are effective for prevention or treatment of gastrointestinal disorder.

BEST MODE FOR CARRYING OUT THE INVENTION

As hereunder, the terms used in the present specification will be illustrated and the compounds of the present invention will be further illustrated.

With regard to "aryl group", a hydrocarbon ring aryl group having 6 to 14 carbons may be listed.

"Lower alkyl group" means a linear or branched alkyl group having 1 to 6 carbon(s) and its examples are methyl group, ethyl group, propyl group, isopropyl group, butyl group, isobutyl group, sec-butyl group, tert-butyl group, pentyl group, isoamyl group, neopentyl group, isopentyl group, 1,1-dimethylpropyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,2,2-trimethylpropyl group and 1-ethyl-2-methylpropyl group.

"Cycloalkyl group" means a cycloalkyl group having 3 to 9 carbons and its examples are cyclopropyl group, cyclobutyl group, cyclopentyl group, cyclohexyl group, cycloheptyl group, cyclooctyl group and cyclononyl group.

"Alkoxy group" means a group where hydrogen atom of hydroxyl group is substituted with the above lower alkyl group and its examples are methoxy group, ethoxy group, propoxy group, isopropoxy group, butoxy group, sec-butoxy group, tert-butoxy group, pentyloxy group, isopentyloxy group, hexyloxy group and isohexyloxy group.

"Halogen atom" means, for example, fluorine atom, chlorine atom, bromine atom an iodine atom.

"Mono-lower alkylamino group" means an amino group where it is mono-substituted with the above lower alkyl group and its examples are methylamino group, ethylamino group, propylamino group, isopropylamino group, butylamino group, sec-butylamino group and tert-butylamino group.

"Di-lower alkylamino group" means an amino group which is di-substituted with same or different above lower alkyl groups and its examples are dimethylamino group, diethylamino group, dipropylamino group, methylpropylamino group and diisopropylamino group.

"Alkylsulfonyl group" means a group where the above alkyl group is bonded to sulfonyl group and its examples are methylsulfonyl group, ethylsulfonyl group, propylsulfonyl group, isopropylsulfonyl group and butylsulfonyl group.

"Trialkylsilyl group" is a silyl group which is tri-substituted with same or different above lower alkyl groups and its examples are trimethylsilyl group and triethylsilyl group.

The compound of the present invention has an mGluR1 inhibitory action and "mGluR1 inhibitory action" used here means any action so far as it inhibits the function of mGluR1 and includes the compound having, for example, an mGluR1 antagonistic action and that which is not antagonistic having an mGluR1 receptor antagonistic action.

In order to more specifically disclose the above formula (I) concerning the present invention, various symbols used for the formula (I)

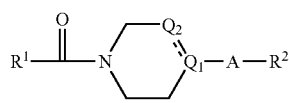

(I)

will be illustrated by following examples.

With regard to the "alkoxy group" represented by $R^1$, its examples are methoxy group, ethoxy group, n-propoxy group, isopropoxy group, n-butoxy group and tert-butoxy group and, among them, n-propoxy group, isopropoxy group and tert-butoxy group are preferred and n-propoxy group and isopropoxy group are more preferred.

With regard to the "linear or branched lower alkyl group" represented by $R^1$, its examples are methyl group, ethyl group, n-propyl group, isopropyl group, n-butyl group, 1-methylpropyl group, tert-butyl group and 1-ethylpropyl group. Among them, isopropyl group, tert-butyl group, 1-methylpropyl group, 1-methylpropyl group and 1-ethylpropyl group are preferred and isopropyl group and tert-butyl group are more preferred.

With regard to the "cycloalkoxy group" represented by $R^1$, its examples are cyclopropyloxy group, cyclobutyloxy group, cyclopentyloxy group, cyclohexyloxy group and cycloheptyloxy group. Among them, cyclopropyloxy group, cyclobutyoxy group and cyclopentyloxy group are preferred and cyclopropyloxy group is more preferred.

The formula (II)

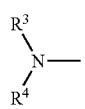

(II)

represented by $R^1$ will be illustrated.

With regard to the "linear or branched lower alkyl group" represented by $R^3$ or $R^4$, its examples are methyl group, ethyl group, n-propyl group, isopropyl group, n-butyl group, tert-butyl group, 1-methylpropyl group and 1-ethylbutyl group. Among them, methyl group, ethyl group, isopropyl group and tert-butyl group are preferred and methyl group, isopropyl group and tert-butyl group are more preferred.

With regard to the "cycloalkyl group" represented by $R^3$ or $R^4$, its examples are cyclopropyl group, cyclobutyl group, cyclopentyl group, cyclohexyl group and cycloheptyl group. Among them, cyclopropyl group and cyclobutyl group are preferred and cyclopropyl group is more preferred.

When $R^3$ and $R^4$ each is a lower alkyl group or a cycloalkyl group, $R^3$ and $R^4$ may be same or different.

With regard to the "four- to seven-membered nitrogen-containing aliphatic heterocyclic group" which is formed by $R^3$ and $R^4$ together with a nitrogen atom in the above formula (II), its examples are pyrrolidin-1-yl group, piperidin-1-yl group and homopiperidin-1-yl group. Among them, pyrrolidin-1-yl group, piperidin-1-yl group and homopiperidin-1-yl group are preferred and pyrrolidin-1-yl group is more preferred.

It is also possible that one of methylene groups constituting the four- to seven-membered nitrogen-containing aliphatic heterocyclic group is substituted with oxygen atom and its example are morpholin-1-yl group and oxazolidin-1-yl group. Among them, morpholin-1-yl group is preferred.

With regard to $R^1$, an alkoxy group, a cycloalkoxy group or a group represented by the formula (II):

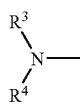

(II)

wherein: each symbol has the same meaning as defined already] is preferred and the group represented by the formula (II) is more preferred.

$R^2$ is phenyl group or a five- to six-membered unsaturated or partially unsaturated hetero ring having, in the ring, one to three hetero atom(s) selected from the group consisting of nitrogen atom, sulfur atom and oxygen atom.

$R^2$ may have, in the ring, one to three substitutent(s) selected from the group consisting of halogen atom, a lower alkyl group, cyano group, nitro group, an alkoxy group, oxo group, hydroxy group and a lower alkylsulfonyl group.

When $R^2$ has two or three the substitutents, they may be same or different.

With regard to the "halogen atom" for the substitutent, its preferred examples are fluorine atom, chlorine atom and bromine atom.

With regard to the "lower alkyl group" for the substitutent, its preferred examples are methyl group, ethyl group and isopropyl group.

With regard to the "alkoxy group" for the substitutent, its preferred examples are methoxy group, ethoxy group, n-propoxy group and isopropoxy group.

With regard to the "five- to six-membered unsaturated hetero ring having one to three hetero atom(s) selected from the group consisting of nitrogen atom, sulfur atom and oxygen atom in the ring", its specific examples are furyl group, thienyl group, pyrrolyl group, imidazolyl group, triazolyl group, pyrazolyl group, thiazolyl group, thiadiazolyl group, isothiazolyl group, oxazolyl group, isoxazolyl group, pyridinyl group, pyrimidinyl group, pyridazinyl group and pyrazinyl group. Among them, preferred ones are pyridinyl group, thienyl group, pyrazinyl group and pyrimidinyl group and more preferred ones are pyridinyl group and thienyl group.

With regard to the "partially unsaturated hetero ring having one to three hetero ring(s) selected from the group consisting of nitrogen atom, sulfur atom and oxygen atom in the ring"

represented by $R^2$, the group represented by the following formula, for example, is preferred.

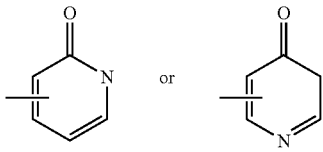

From the above, with regard to $R^2$ which may have one to three substitutent(s) selected from the group consisting of halogen atom, lower alkyl group, cyano group, nitro group, an alkoxy group, oxo group and hydroxyl group in the ring, its more specific examples are phenyl group, furan-2-yl group, furan-3-yl group, thiophen-2-yl group, thiophen-3-yl group, pyrrol-2-yl group, pyrrol-3-yl group, imidazol-2-yl group, imidazol-4-yl group, triazol-3-yl group, pyrazol-4-yl group, thiazol-2-yl group, [1,2,4]thiadiazol-3-yl group, [1,3,4]thiadiazol-2-yl group, isothiazol-3-yl group, oxazol-2-yl group, isoxazol-3-yl group, pyridin-2-yl group, pyridin-3-yl group, pyridin-4-yl group, pyrimidin-2-yl group, pyrimidin-4-yl group, pyridazin-4-yl group, pyrazin-2-yl group, pyridon-3-yl group, pyridon-4-yl group, 2-chlorophenyl group, 3-chlorophenyl group, 4-chlorophenyl group, 2-fluorophenyl group, 3-fluorophenyl group, 4-fluorophenyl group, 2-methylphenyl group, 3-methylphenyl group, 4-methylphenyl group, 2-hydroxyphenyl group, 3-hydroxyphenyl group, 4-hydroxyphenyl group, 2-methoxyphenyl group, 3-methoxyphenyl group, 4-methoxyphenyul group, 2-cyanophenyl group, 3-cyanophenyl group, 4-cyanophenyl group, 2-nitrophenyl group, 3-nitrophenyl group, 4-nitrophenyl group, 2-chloropyridin-3-yl group, 4-chloropyridin-3-yl group, 2-fluoropyridin-3-yl group, 4-fluoropyridin-3-yl group, 6-fluoropyridin-2-yl group, 2-cyanopyridin-3-yl group and 4-cyanopyridin-3-yl group. Among them, phenyl group, thiophen-2-yl group, thiophen-3-yl group, pyridin-2-yl group, pyridin-3-yl group and pyridin-4-yl group are preferred and phenyl group and pyridin-3-yl group are more preferred.

Now, a group represented by the following formula (V) in the formula (I) will be illustrated.

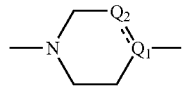

(V)

With regard to the formula (V), it specifically means the groups represented by the formulae (V-4)

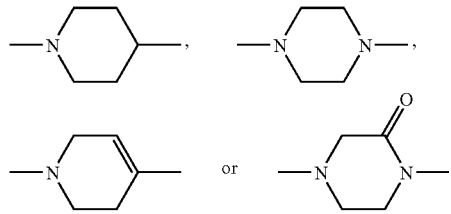

(V-4)

and, among them, the groups represented by the formula (V-5) are preferred

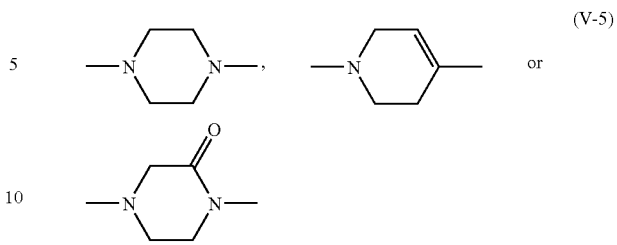

(V-5)

and the group represented by the formula (V-6) is more preferred.

(V-6)

Now, A will be illustrated. A is a group selected from the group consisting of the above substitutent group α:

Substituent Group α

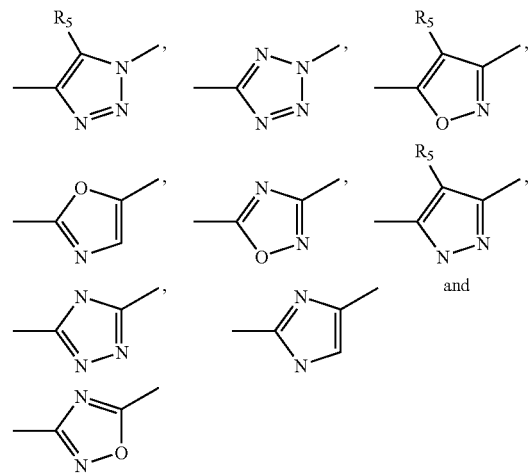

in the formulae, each of the symbols has the same meaning as defined already] and, among them, any of the groups represented by the formula (IV-4):

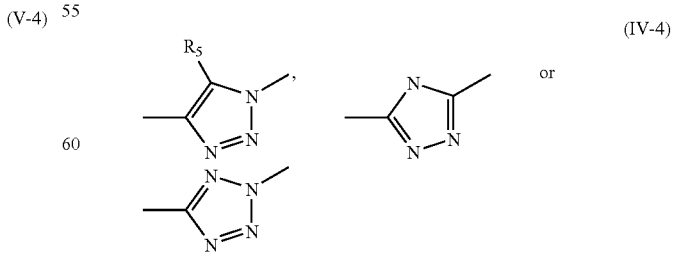

(IV-4)

is preferred, the groups represented by the formulae (IV-5):

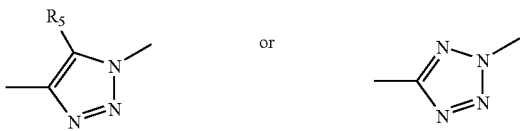

are more preferred and the group represented by the formula (IV-6):

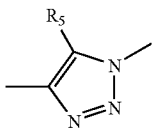

is particularly preferred.

With regard to the "lower alkyl group (the alkyl group may be substituted with an alkoxy group)" represented by $R^5$, its examples are methyl group, ethyl group, isopropyl group and n-propyl group and, among them, methyl group is preferred.

With regard to the "alkoxy group" represented by $R^5$, its examples are methoxy group, ethoxy group and isopropyloxy group.

With regard to the "trialkylsilyl group" represented by $R^5$, its examples are trimethylsilyl group and triethylsilyl group and, among them, trimethylsilyl group is preferred.

With regard to $R^5$, examples of preferred one are methyl group, ethyl group, isopropyl group, n-propyl group, methoxy group, trimethylsilyl group and cyano group; examples of more preferred ones are methyl group, trimethylsilyl group and cyano group; and examples of particularly preferred ones are methyl group, etc.

From the above, with regard to the compound of the present invention represented by the formula (I):

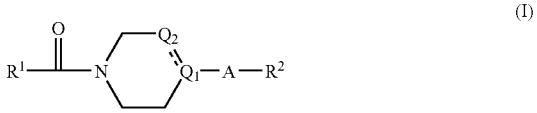

wherein:

each of the symbols has the same meaning as that defined already, its specific examples are isopropyl 4-[1-(2-fluoropyridin-3-yl)-5-methyl-1H-[1,2,3]triazol-4-yl]-1,2,3,6-tetrahydropyridine-1-carboxylate, 4-[1-(2-fluoropyridin-3-yl)-5-methyl-1H-[1,2,3]triazol-4-yl]-1,2,3,6-tetrahydropyridine-1-carboxylic acid pyrrolidineamide, 4-[1-(2-fluoropyridin-3-yl)-5-methyl-1H-[1,2,3]triazol-4-yl]-2,3,6-tetrahydropyridine-1-carboxylic acid diethylamide, 4-[1-(2-fluoropyridin-3-yl)-5-methyl-1H-[1,2,3]triazol-4-yl]-1,2,3,6-tetrahydropyridine-1-carboxylic acid piperidineamide, isopropyl 4-[1-(2-chlorophenyl)-5-methyl-1H-[1,2,3]triazol-4-yl]-1,2,3,6-tetrahydropyridine-1-carboxylate, 4-[1-(2-fluoropyridin-3-yl)-5-methyl-1H-[1,2,3]triazol-4-yl]-1,2,3,6-tetrahydropyridine-1-carboxylic acid isopropylmethylamide, 4-[1-(2-fluoropyridin-3-yl)-5-methyl-1H-[1,2,3]triazol-4-yl]-1,2,3,6-tetrahydropyridine-1-carboxylic acid tert-butylamide, isopropyl 4-[1-phenyl-5-methyl-1H-[1,2,3]triazole-4-yl]-1,2,3,6-tetrahydropyridine-1-carboxylate, isopropyl 4-[1-(2-chloropyridin-3-yl)-5-methyl-1H-[1,2,3]triazol-4-yl]-1,2,3,6-tetrahydropyridine-1-carboxylate, isopropyl 4-[1-(2-fluoropyridin-5-yl)-5-methyl-1H-[1,2,3]triazol-4-yl]-1,2,3,6-tetrahydropyridine-1-carboxylate, propyl 4-[1-(2-chloropyridin-3-yl)-5-methyl-1H-[1,2,3]triazol-4-yl]-1,2,3,6-tetrahydropyridine-1-carboxylate, ethyl 4-[1-(2-chloropyridin-3-yl)-1H-[1,2,3]triazol-4-yl]-1,2,3,6-tetrahydropyridine-1-carboxylate, 2-methylpropyl 4-[1-(2-chloropyridin-3-yl)-5-methyl-1H-[1,2,3]triazol-4-yl]-1,2,3,6-tetrahydropyridine-1-carboxylate, isopropyl 4-[1-(pyridin-3-yl)-1H-[1,2,3]triazol-4-yl]-1,2,3,6-tetrahydropyridine-1-carboxylate, isopropyl 4-[5-cyano-1-phenyl-1H-[1,2,3]triazol-4-yl]-1,2,3,6-tetrahydropyridine-1-carboxylate, 4-[1-(2-chloropyridin-3-yl)-5-methyl-1H-[1,2,3]triazole-4-yl]-1,2,3,6-tetrahydropyridine-1-carboxylic acid pyrrolidineamide, 4-[1-(2-fluoro-pyridin-3-yl)-1H-[1,2,3]triazol-4-yl]-1,2,3,6-tetrahydropyridine-1-carboxylic acid isopropylamide, 4-[1-(2-chloro-pyridin-3-yl)-1H-[1,2,3]triazol-4-yl]-1,2,3,6-tetrahydropyridine-1-carboxylic acid isopropylmethylamide, 4-[1-(2-chloropyridin-3-yl)-5-methyl-1H-[1,2,3]triazol-4-yl]-1,2,3,6-tetrahydropyridine-1-carboxylic acid piperidineamide, 4-[1-(2-chloropyridin-3-yl)-5-methyl-1H-[1,2,3]triazol-4-yl]-1,2,3,6-tetrahydropyridine-1-carboxylic acid methyl-tert-butylamide, 4-[1-(2-chloropyridin-3-yl)-1H-[1,2,3]triazol-4-yl]-1,2,3,6-tetrahydropyridine-1-carboxylic acid tert-butylamide, 1-{4-[1-(2-chloropyridin-3-yl)-1H-[1,2,3]triazol-4-yl]-1,2,3,6-tetrahydropyridin-1-yl}-3-methyl-1-butanone, isopropyl 4-[1-(2-fluoropyridin-3-yl)-1H-[1,2,3]triazol-4-yl]-1,2,3,6-tetrahydropyridine-1-carboxylate and isopropyl 4-[1-phenyl-5-propyl-1H-[1,2,3]triazol-4-yl]-1,2,3,6-tetra-hydropyridine-carboxylate and, among them, preferred ones are isopropyl 4-[1-(2-fluoropyridin-3-yl)-5-methyl-1H-[1,2,3]-triazol-4-yl]-1,2,3,6-tetrahydropyridine-1-carboxylate, 4-[1-(2-fluoropyridin-3-yl)-5-methyl-1H-[1,2,3]triazol-4-yl]-1,2,3,6-tetrahydropyridine-1-carboxylic acid pyrrolidineamide, 4-[1-(2-fluoropyridin-3-yl)-5-methyl-1H-[1,2,3]triazol-4-yl]-1,2,3,6-tetrahydropyridine-1-carboxylic acid diethylamide, 4-[1-(2-fluoropyridin-3-yl)-5-methyl-1H-[1,2,3]triazol-4-yl]-1,2,3,6-tetrahydropyridine-1-carboxylic acid piperidineamide, isopropyl 4-[1-(2-chlorophenyl)-5-methyl-1H-[1,2,3]triazol-4-yl]-1,2,3,6-tetrahydropyridine-1-carboxylate, 4-[1-(2-fluoropyridin-3-yl)-5-methyl-1H-[1,2,3]triazol-4-yl]-1,2,3,6-tetrahydropyridine-1-carboxylic acid isopropylmethylamide, 4-[1-(2-fluoropyridin-3-yl)-5-methyl-1H-[1,2,3]triazol-4-yl]-1,2,3,6-tetrahydropyridine-1-carboxylic acid tert-butylamide, isopropyl 4-[1-(2-fluoropyridin-5-yl)-5-methyl-1H-[1,2,3]triazol-4-yl]-1,2,3,6-tetrahydropyridine-1-carboxylate, 4-[1-(2-chloropyridin-3-yl)-5-methyl-1H-[1,2,3]triazol-4-yl]-1,2,3,6-tetrahydropyridine-1-carboxylic acid pyrrolidineamide and 4-[1-(2-chloropyridin-3-yl)-1H-[1,2,3]triazol-4-yl]-1,2,3,6-tetrahydropyridine-1-carboxylic acid isopropylmethylamide.

The compound (I) of the present invention is able to be produced using a known reaction means or according to a process which is known per se. Incidentally, the compound (I) of the present invention is also able to be produced not only by a common synthetic method in a liquid phase but also by a process using a solid phase which has been significantly developed in recent years such as a combinatorial synthetic method and a parallel synthetic method.

The compound (I-1), (I-2) or (I-3) of the present invention is able to be produced, for example, by the following method.

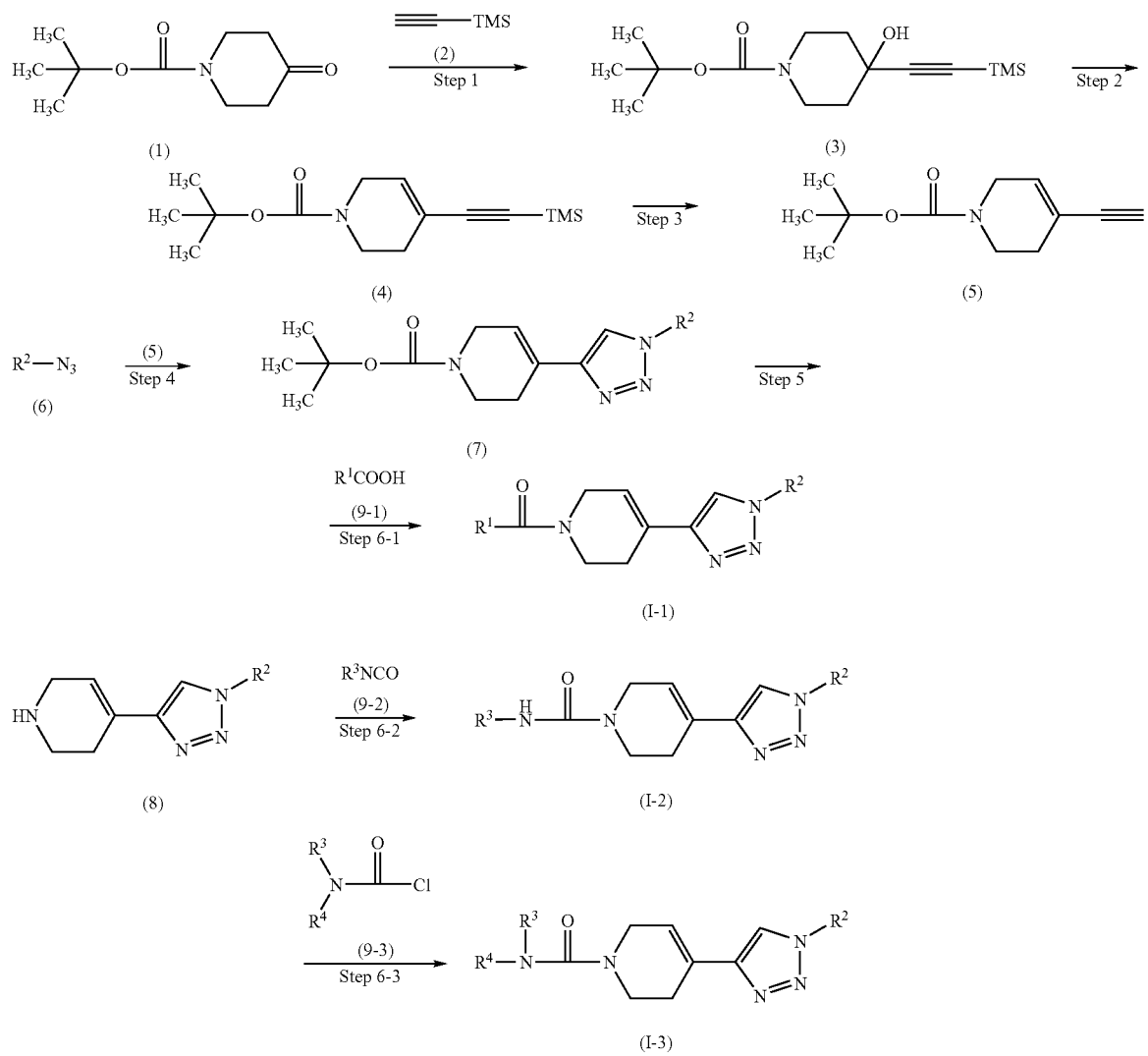

In the formulae, TMS means trimethylsilyl group while other symbols have the same meanings as those defined already.

(Step 1)

This step is a process where 1-Boc-4-piperidone (1) is made to react with trimethylsilyl acetylene (2) in the presence of a base to produce a compound (3). (Here, Boc means tert-butoxycarbonyl group. Hereinafter, it is also used in the same meaning.)

Various acetylene compounds may be used in place of trimethylsilyl acetylene (2) and examples of such acetylene compounds are bis(trimethylsilyl)acetylene, 1-propynyl magnesium bromide, 1-propyl magnesium chloride and 1-propynyl lithium.

Amount of the acetylene compound used in this step is usually 1 to 50 equivalent(s) and, preferably, 2 to 10 equivalents to one equivalent of the compound (1).

Examples of the base used are butyl lithium, lithium diisopropylamide, potassium tert-butoxide, methyl lithium and phenyl lithium and preferred ones are butyl lithium, lithium diisopropylamide and potassium tert-butoxide. When 1-propynyl magnesium bromide or 1-propynyl magnesium chloride is used in place of trimethylsilyl acetylene (2), it is possible to carry out the reaction even if no base is used.

With regard to a solvent for the reaction, there is no particular limitation so far as it does not affect the reaction and its examples are tetrahydrofuran (THF), diethyl ether, toluene, hexane, pyridine, dimethylformamide (DMF) and N-methylpyrrolidone (NMP). Among them, THF, diethyl ether, toluene and hexane are preferred.

Reaction temperature is usually from −78° C. to 100° C. and, preferably, from −78° C. to room temperature.

Reaction time is usually from 10 minutes to 7 days and, preferably, from 30 minutes to 2 hours.

The compound (3) prepared as such is able to be subjected to the next step with or without isolation and purification by means of known separation/purification means such as concentration, concentration in vacuo, crystallization, extraction with solvent, re-precipitation and chromatography.

(Step 2)

This step is a process where the compound (3) is subjected to a dehydration reaction to produce a compound (4). This reaction is able to be carried out, for example, by any of the following (step 2-1) and (step 2-2).

(Step 2-1)

This is a process where the compound (3) is made to react with methanesulfonyl chloride or the like in the presence of a base such as triethylamine.

(Step 2-2)

This is a process where the compound (3) is made to react with thionyl chloride or trifluoroacetic acid (TFA).

With regard to the base used in the step 2-1, diisobutylethylamine, pyridine, collidine, lutidine, dimethylaminopyridine, DBU, etc. may be used besides triethylamine and, among them, triethylamine, pyridine, dimethylaminopyridine, etc. are preferred.

Amount of the base used is usually 1 to 10 equivalent(s) and, more preferably, 1 to 3 equivalent(s) to one equivalent of the compound (3).

Amount of methanesulfonyl chloride used in the step 2-1 is usually to 50 equivalent(s) and, preferably, 1 to 5 equivalent(s) to one equivalent of the compound (3).

Amount of thionyl chloride used in the step 2-2 is usually 1 to 100 equivalent(s) and, preferably, 1 to 10 equivalent(s) to one equivalent of the compound (3).

With regard to the solvent used in the step 2-1, there is no particular limitation so far as it does not affect the reaction and its examples are chloroform, methylene chloride, tetrahydrofuran (THF), diethyl ether, toluene, hexane, ethyl acetate, pyridine, dimethylformamide (DMF) and N-methylpyrrolidone. Among them, chloroform, methylene chloride, THF, diethyl ether and ethyl acetate are preferred.

With regard to the solvent used in the step 2-2, there is no particular limitation so far as it does not affect the reaction and its examples are chloroform, methylene chloride, tetrahydrofuran (THF), diethyl ether, toluene, hexane, ethyl acetate, pyridine, dimethylformamide (DMF) and N-methylpyrrolidone (NMP). Among them, chloroform, methylene chloride and THF are preferred.

Reaction temperature in the step 2-1 is usually from 0° C. to 100° C. and, preferably, from 0° C. to 50° C.

Reaction time in the step 2-1 is usually from 10 minutes to 12 hours and, preferably, from 10 minutes to 2 hours.

Reaction temperature in the step 2-2 is usually from 0° C. to 120° C. and, preferably, from 0° C. to 80° C.

Reaction time in the step 2-2 is usually from 10 minutes to 24 hours and, preferably, from 30 minutes to 5 hours.

The compound (4) prepared as such is able to be subjected to the next step with or without isolation and purification by means of known separation/purification means such as concentration, concentration in vacuo, crystallization, extraction with solvent, re-precipitation and chromatography.

(Step 3)

This step is a process where TMS group in the compound (4) prepared in the above step 2 is removed to produce a compound (5).

Removal of TMS group is able to be carried out by a known method (such as that mentioned in "Protective Groups in Organic Synthesis" by T. W. Greene, second edition, John Wiley & Sons, 1991), a method similar thereto or a combination of them with a conventional method and the compound (4) is made to react, for example, with potassium carbonate, tetrabutylammonium fluoride or hydrogen fluoride to prepare a compound (5).

Amount of potassium carbonate, tetrabutylammonium fluoride or hydrogen fluoride used is usually 1 to 100 equivalent(s) and, preferably, 1 to 5 equivalent(s) to one equivalent of the compound (4).

With regard to the reaction solvent, there is no particular limitation so far as it does not affect the reaction and its examples are tetrahydrofuran (THF), diethyl ether, toluene, hexane, pyridine, dimethylformamide (DMF), N-methylpyrrolidone (NMP), methanol, ethanol and chloroform. Among them, THF, diethyl ether and methanol are preferred.

Reaction temperature is usually from −78° C. to 100° C. and, preferably, from 0° C. to 50° C.

Reaction time is usually from 10 minutes to 7 days and, preferably, from 30 minutes to 2 hours.

The compound (5) prepared as such is able to be subjected to the next step with or without isolation and purification by means of known separation/purification means such as concentration, concentration in vacuo, crystallization, extraction with solvent, re-precipitation and chromatography.

(Step 4)

This step is a process where the compound (6) is made to react with the compound (5) prepared in the previous step 3 to produce a compound (7).

Specific examples of the compound (6) used are phenyl azide, pyridyl azide, fluoropyridyl azide, pyrazyl azide, mono- or di-fluorophenyl azide, mono- or di-chlorophenyl azide and toluyl azide.

Amount of the compound (5) used is usually 0.5 to 50 equivalent(s) and, preferably, 2 to 10 equivalents to one equivalent of the compound (6).

With regard to the reaction solvent, there is no particular limitation so far as it does not affect the reaction and its examples are toluene, benzene, xylene, DMF, NMP, dioxane, THF and DMSO. Among them, toluene and benzene are preferred.

Reaction temperature is usually from 0° C. to 150° C. and, preferably, from 50° C. to 120° C.

Reaction time is usually from 30 minutes to 7 days and, preferably, from 2 hours to 12 hours.

The compound (7) prepared as such is able to be subjected to the next step with or without isolation and purification by means of known separation/purification means such as concentration, concentration in vacuo, crystallization, extraction with solvent, re-precipitation and chromatography.

(Step 5)

This step is a process where the Boc group of the compound (7) prepared in the above step 4 is removed to produce a compound (8).

This reaction is able to be carried out by a known method (such as that mentioned in "Protective Groups in Organic Synthesis" by T. W. Greene, second edition, John Wiley & Sons, 1991), a method similar thereto or a combination of them with a conventional method and, to be more specific, hydrochloric acid-methanol or TFA may be exemplified.

Amount of the hydrochloric acid-methanol or TFA is usually from 1 equivalent to a solvent amount to one equivalent of the compound (7).

With regard to the reaction solvent, there is no particular limitation so far as it does not affect the reaction and its examples are chloroform, tetrahydrofuran (THF), diethyl ether, toluene, hexane, pyridine, dimethylformamide (DMF), N-methylpyrrolidone (NMP), methanol and ethanol. Among them, chloroform, THF and methanol are preferred.

Reaction temperature is usually from −78° C. to 100° C. and, preferably, from 0° C. to 30° C.

Reaction time is usually from 10 minutes to 2 days and, preferably, from 10 minutes to 2 hours.

The compound (8) prepared as such is able to be subjected to the next step with or without isolation and purification by means of known separation/purification means such as concentration, concentration in vacuo, crystallization, extraction with solvent, re-precipitation and chromatography.

(Step 6-1)

This step is a process where the compound (8) prepared in the above step 5 is made to react with a carboxylic acid compound (9-1) or a reactive derivative thereof to produce a compound (I-1) of the present invention. In this reaction, a conventional reaction for production of an amide is carried out by a method mentioned in the literature (such as "Base and Experiments of Peptide Synthesis" by Nobuo Izumiya, et al., Maruzen, 1983; "Comprehensive Organic Synthesis", volume 6, Pergamon Press, 1991; etc.), a method similar thereto or a combination of them with a common method. Thus, it is conducted using a condensing agent which has been known to persons skilled in the art or by an ester activation method, a mixed acid anhydride method, an acid chloride method, a carbodiimide method, etc. which are able to be utilized by persons skilled in the art. With regard to a reagent for production of an amide as such, its examples are thionyl chloride, oxazolyl chloride, N,N-dicyclohexylcarbodiimide, 1-methyl-2-bromopyridinum iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, ethyl chloroformate, isobutyl chloroformate and benzotriazo-1-yloxy-tris(dimethylamino)phosphonium hexafluorophosphate. Among them, preferred ones are thionyl chloride, 1-ethyl-3-(3-dimethylaminopropyl)carbodiimide hydrochloride, N,N-dicyclohexylcarbodiimide and benzotriazo-1-yloxy-tris(dimethylamino)phosphonium hexafluorophosphate. In the reaction for the formation of an amide, it is also possible to use a base and a condensation aid together with the above reagent for the formation of an amide.

Examples of the base used are a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) and 1,5-azabicyclo[4.3.0]non-5-ene (DBN) and an aromatic amine such as pyridine, 4-dimethylaminopyridine, picoline, lutidine, quinoline and isoquinoline. Among them, a tertiary aliphatic amine is preferred and triethylamine and N,N-diisopropylethylamine are particularly preferred.

With regard to the condensation aid used, its examples are N-hydroxybenzotriazole hydrate, N-hydroxysuccinimide, N-hydroxy-5-norbornene-2,3-dicarboxylmide and 3-hydroxy-3,4-dihydro-4-oxo-1,2,3-benzotriazole. Among them, N-hydroxybenzotriazole, etc. are preferred.

Although the amount of the compound (9-1) or a reactive derivative thereof used varies depending upon the type of the compound and of the solvent used as well as upon other reaction conditions, it is usually from 1 to 50 equivalent(s) and, preferably, from 2 to 10 equivalents to one equivalent of the compound (8).

Although the amount of the reagent for the formation of an amide used varies depending upon the type of the compound and of the solvent used as well as upon other reaction conditions, it is usually from 1 to 50 equivalent(s) and, preferably, from 2 to 10 equivalents to one equivalent of the compound (8).

Although the amount of the condensation aid used varies depending upon the type of the compound and of the solvent used as well as upon other reaction conditions, it is usually from 1 to 50 equivalent(s) and, preferably, from 2 to 10 equivalents to one equivalent of the compound (8).

Although the amount of the base used varies depending upon the type of the compound and of the solvent used as well as upon other reaction conditions, it is usually from 1 to 50 equivalent(s) and, preferably, from 2 to 5 equivalents to one equivalent of the compound (8).

Although there is no particular limitation for the reaction solvent used in this step, its specific examples are chloroform, methylene chloride, THF, diethyl ether, DMF, N-methylpyrrolidone, dioxane, DMSO, toluene, benzene and xylene. Among them, preferred examples are chloroform, methylene chloride, THF, diethyl ether, DMF, N-methylpyrrolidone, toluene, benzene and xylene.

Reaction temperature in this step is usually from −78° C. to 150° C. and, preferably, from 0° C. to 50° C.

Reaction time in this step is usually from 30 minutes to 7 days and, preferably, from 30 minutes to 12 hours.

With regard to the base, the reagent for the production of an amide and the condensation aid used in this step, one of them or more in combination may be used.

The compound (26) prepared as such is able to be isolated and purified by a known separation/purification means such as concentration, concentration in vacuo, crystallization, extraction with solvent, re-precipitation and chromatography.

(Step 6-2)

This step is a process for the production of the compound (I-2) of the present invention where the compound (8) prepared in the above step 5 with the compound (9-2) in the presence of a base.

Examples of the base used in this step are a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) and 1,5-azabicyclo[4.3.0]non-5-ene (DBN) and an aromatic amine such as pyridine, 4-dimethylaminopyridine, picoline, lutidine, quinoline and isoquinoline. Among them, a tertiary aliphatic amine is preferred and triethylamine and N,N-diisopropylamine are particularly preferred.

Amount of the base is usually from 1 equivalent to a solvent amount to one equivalent of the compound (8).

With regard to the compound (9-2) used in this step, its examples are tert-butyl isocyanate, isopropyl cyanate and isobutyl cyanate.

Amount of the compound (9-2) is usually from 1 to 50 equivalent(s) and, preferably, from 2 to 10 equivalents to one equivalent of the compound (8).

Although there is no particular limitation for the reaction solvent used in this step, its specific examples are chloroform, methylene chloride, THF, diethyl ether, DMF, N-methylpyrrolidone, dioxane, DMSO, toluene, benzene and xylene. Among them, preferred examples are chloroform, methylene chloride, THF, diethyl ether, DMF, N-methylpyrrolidone, toluene, benzene and xylene.

Reaction temperature in this step is usually from −78° C. to 150° C. and, preferably, from 0° C. to 50° C.

Reaction time in this step is usually from 30 minutes to 7 days and, preferably, from 30 minutes to 12 hours.

The compound (I-2) prepared as such is able to be isolated and purified by a known separation/purification means such as concentration, concentration in vacuo, crystallization, extraction with solvent, re-precipitation and chromatography.

(Step 6-3)

This step is a process for the production of a compound (I-3) of the present invention by the reaction of the compound (8) with the compound (9-3).

With regard to the compound (9-3) used in this step, its examples are dimethylcarbamoyl chloride, diethylcarbamoyl chloride, diisopropylcarbamoyl chloride, isopropylmethylcarbamoyl chloride, 1-pyrrolidinecarbamoyl chloride, 1-piperidinecarbamoyl chloride and 4-morpholinecarbamoyl chloride.

Amount of the (9-3) used is usually from 1 to 50 equivalent(s) and, preferably, from 2 to 10 equivalents to one equivalent of the compound (8).

It is also possible to conduct the reaction of this step using a base.

Examples of the base used are a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) and 1,5-azabicyclo[4.3.0]non-5-ene (DBN) and an aromatic amine such as pyridine, 4-dimethylaminopyridine, picoline, lutidine, quinoline and isoquinoline. Among them, a tertiary aliphatic amine is preferred and triethylamine and N,N-diisopropylamine are particularly preferred.

Although there is no particular limitation for the reaction solvent used in this step, its specific examples are chloroform, methylene chloride, THF, diethyl ether, DMF, N-methylpyrrolidone, dioxane, DMSO, toluene, pyridine, benzene and xylene. Among them, preferred examples are pyridine, chloroform, methylene chloride, THF, diethyl ether, DMF, N-methylpyrrolidone, toluene, benzene and xylene.

Reaction temperature in this step is usually from −78° C. to 150° C. and, preferably, from 0° C. to 50° C.

Reaction time in this step is usually from 30 minutes to 7 days and, preferably, from 30 minutes to 12 hours.

The compound (I-3) prepared as such is able to be isolated and purified by a known separation/purification means such as concentration, concentration in vacuo, crystallization, extraction with solvent, re-precipitation and chromatography.

The compound (I-4), (I-5) or (I-6) according to the present invention is able to be produced by the following methods.

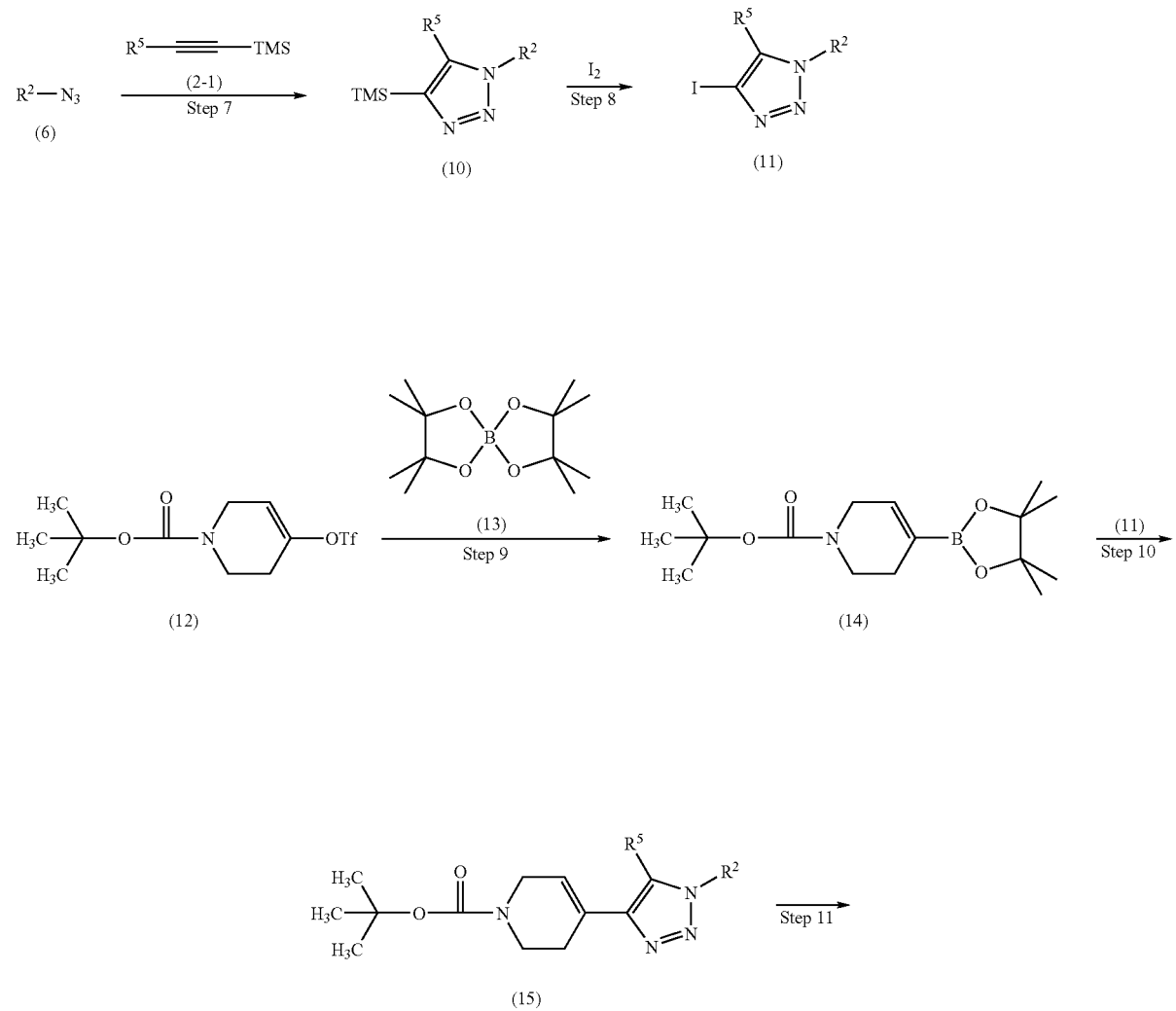

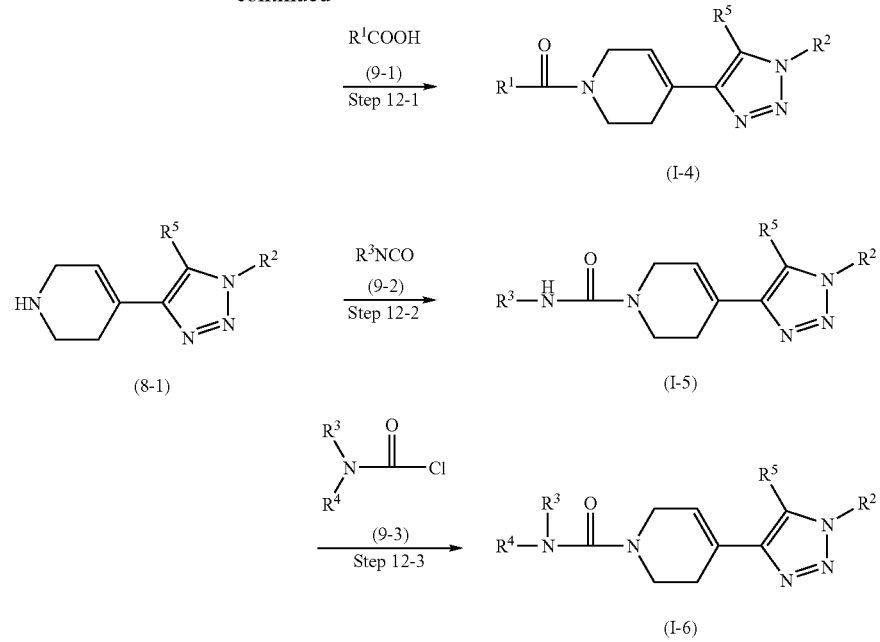

In the formula, Tf is $CF_3$—$S(O)_2$—.

Each step will be illustrated as follows.

(Step 7)

This step is a process where the above compound (6) is made to react with a compound (2-1) to produce a compound (10).

Amount of the compound (2-1) used in this step is usually from 1 to 50 equivalent(s) and, preferably, from 1 to 20 equivalent(s) to one equivalent of the compound (6).

Although there is no particular limitation for the reaction solvent used in this step, its specific examples are toluene, benzene, xylene, DMF, N-methylprrolidone, dioxane, THF and DMSO. Among them, preferred examples are toluene, benzene and xylene.

Reaction temperature in this step is usually from 0° C. to 150° C. and, preferably, from 50° C. to 120° C.

Reaction time in this step is usually from 30 minutes to 7 days and, preferably, from 2 hours to 12 hours.

The compound (10) prepared as such is able to be subjected to the next step with or without isolation and purification by a known separation/purification means such as concentration, concentration in vacuo, crystallization, extraction with solvent, re-precipitation and chromatography.

(Step 8)

This is step is a process where the compound (10) prepared in the above step 7 is made to react with iodine in the presence of $AgBF_4$ to produce a compound (11).

Amount of $AgBF_4$ used in this step is usually from 1 to 50 equivalent(s) and, preferably, from 2 to 10 equivalents to one equivalent of the compound (10).

Although there is no particular limitation for the reaction solvent used in this step, its specific examples are methanol, ethanol, THF, diethyl ether, DMF and dioxane. Among them, preferred examples are methanol, ethanol and THF.

Reaction temperature in this step is usually from −60° C. to 150° C. and, preferably, from 0° C. to room temperature.

Reaction time in this step is usually from 30 minutes to 7 days and, preferably, from 30 minutes to 12 hours.

The compound (11) prepared as such is able to be subjected to the next step with or without isolation and purification by a known separation/purification means such as concentration, concentration in vacuo, crystallization, extraction with solvent, re-precipitation and chromatography.

(Step 9)

This step is a process where the compound (12) is made to react with the compound (13) in the presence of a base and a catalyst to produce a compound (14).

With regard to the base used in this step, its examples are sodium carbonate, potassium carbonate and potassium acetate.

Amount of the base used in this step is usually from 1 to 100 equivalent(s) and, preferably, 1 to 5 equivalent(s) to one equivalent of the compound (12).

With regard to the catalyst used in the present invention, its examples are $Pd(PPh_3)_4$, $Pd_2(dba_3)$ and $PdCl_2(dppf)_2$.

Amount of the catalyst used in this step is usually from 1% mol to 200% mol and, preferably, from 5% mol to 20% mol to one equivalent of the compound (12).

Amount of the boron compound (13) used in this step is usually from 1 to 10 equivalent(s) and, preferably, from 1 to 3 equivalent(s) to one equivalent of the compound (12).

Although there is no particular limitation for the reaction solvent used in this step, its specific examples are toluene, DMF, N-methylpyrrolidone, dioxane, THF, DMSO and water. Among them, preferred examples are toluene, DMF and N-methylpyrrolidone.

Reaction temperature in this step is usually from 0° C. to 150° C. and, preferably, from 50° C. to 120° C.

Reaction time in this step is usually from 30 minutes to 7 days and, preferably, from 6 hours to 12 hours.

The compound (14) prepared as such is able to be subjected to the next step with or without isolation and purification by a known separation/purification means such as concentration, concentration in vacuo, crystallization, extraction with solvent, re-precipitation and chromatography.

The compound (12) which is used in this step is also able to be produced by the reaction of N-Boc-4-piperidone with the compound (12-1) or (12-2) represented by the following formula in a reaction solvent such as THF in the presence of a base such as lithium diisopropylamide (hereinafter, referred to as LDA).

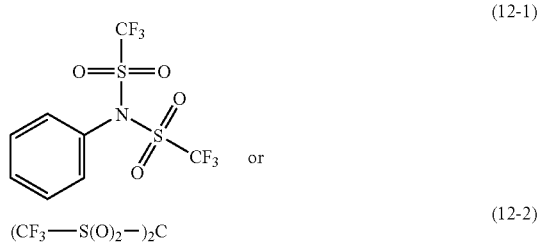

Amount of the base such as LDA used in the production of the compound (12) is usually from 1 to 50 equivalent(s) and, preferably, from 1 to 5 equivalent(s) to one equivalent of N-Boc-4-piperidone.

Although there is no particular limitation for the reaction solvent used in this step, its preferred examples are THF, etc.

Reaction temperature in this step is usually from −78° C. to 100° C. and, preferably, from −78° C. to 30° C.

Reaction time in this step is usually from 0.5 to 24 hour(s) and, preferably, from 30 minutes to 2 hours.

The compound (12) prepared as such is able to be subjected to the step 9 with or without isolation and purification by a known separation/purification means such as concentration, concentration in vacuo, crystallization, extraction with solvent, re-precipitation and chromatography.

(Step 10)

This step is a process where the compound (14) prepared in the above step 9 is made to react with the compound (11) which is prepared in the above step 8 in the presence of a base and a catalyst to produce a compound (15).

With regard to the base used in this step, its examples are sodium carbonate and potassium carbonate.

Amount of the base used in this step is usually from 1 to 10 equivalent(s) and, preferably, 1 to 3 equivalent(s) to one equivalent of the compound (14).

With regard to the catalyst used, its examples are $Pd(PPh_3)_4$, $Pd_2(dba)_3$ and $PdCl_2(dpPf)_2$.

Amount of the catalyst used in this step is usually from 1% mol to 200% mol and, preferably, from 5% mol to 20% mol to one equivalent of the compound (14).

Although there is no particular limitation for the reaction solvent used in this step, its specific examples are toluene, DMF, N-methylpyrrolidone, dioxane, THF, DMSO and water. Among them, preferred examples are toluene, DMF and N-methylpyrrolidone.

Reaction temperature in this step is usually from 0° C. to 150° C. and, preferably, from 50° C. to 120° C.

Reaction time in this step is usually from 30 minutes to 7 days and, preferably, from 6 hours to 12 hours.

The compound (15) prepared as such is able to be subjected to the next step with or without isolation and purification by a known separation/purification means such as concentration, concentration in vacuo, crystallization, extraction with solvent, re-precipitation and chromatography.

(Step 11)

This step is a process where the Boc group of the compound (15) prepared in the above step 10 is removed to produce a compound (8-1).

The reaction in this step may follow the same reaction conditions as in the above step 5.

The compound (8-1) prepared as such is able to be subjected to the next step with or without isolation and purification by a known separation/purification means such as concentration, concentration in vacuo, crystallization, extraction with solvent, re-precipitation and chromatography.

(Step 12-1)

This step is a process where the compound (8-1) prepared in the above step 11 is made to react with a compound (9-1) to produce a compound (I-4) of the present invention.

The reaction in this step may follow the same reaction conditions as in the above step 6-1.

The compound (I-4) prepared as such is able to be isolated and purified by a known separation/purification means such as concentration, concentration in vacuo, crystallization, extraction with solvent, re-precipitation and chromatography.

(Step 12-2)

This step is a process where the compound (8-1) prepared in the above step 11 is made to react with a compound (9-2) to produce a compound (I-5) of the present invention.

The reaction in this step may follow the same reaction conditions as in the above step 6-2.

The compound (I-6) prepared as such is able to be isolated and purified by a known separation/purification means such as concentration, concentration in vacuo, crystallization, extraction with solvent, re-precipitation and chromatography.

(Step 12-3)

This step is a process where the compound (8-1) prepared in the above step 11 is made to react with a compound (9-3) to produce a compound (I-6) of the present invention.

The reaction in this step may follow the same reaction conditions as in the above step 6-3.

The compound (26) prepared as such is able to be subjected to the next step with or without isolation and purification by a known separation/purification means such as concentration, concentration in vacuo, crystallization, extraction with solvent, re-precipitation and chromatography.

The compounds (I-5) and (I-6) of the present invention are able to be produced by the following methods.

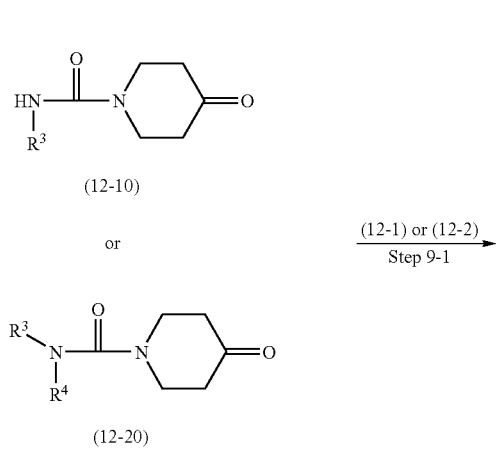

-continued

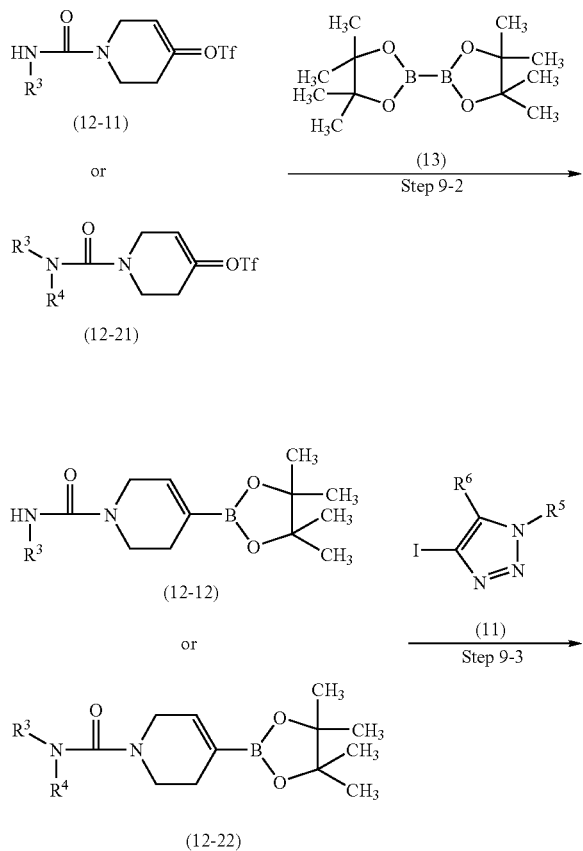

(I-5)

or (I-6)

In the formulae, each of the symbols has the same meaning as defined already.

(Step 9-1)

This step is a process where the compound (12-10) or the compound (12-20) is made to react with the above compound (12-1) or (12-2) in the presence of a base to produce a compound (12-11) or (12-21).

With regard to the base used in this step, its examples are LDA, etc.

Amount of the base used is usually from 1 to 50 equivalent(s) and, preferably, 1 to 5 equivalent(s) to one equivalent of the compound (12-10) or (12-20).

Amount of the compound (12-1) or (12-2) used is usually from 1 to 50 equivalent(s) and, preferably, 1 to 3 equivalent(s) to one equivalent of the compound (12-10) or (12-20).

With regard to the reaction solvent used in this step, although there is no particular limitation so far as it does not affect the reaction, an example thereof is THF.

Reaction temperature in this step is usually from −78° C. to 100° C. and, preferably from 0° C. to 30° C.

Reaction time in this step is usually from 10 minutes to 24 hours and, preferably, from 30 minutes to 2 hours.

The compound (12-11) or (12-21) prepared as such is able to be subjected to the next step with or without isolation and purification by a known separation/purification means such as concentration, concentration in vacuo, crystallization, extraction with solvent, re-precipitation and chromatography.

(Step 9-2)

This step is a process where the compound (12-11) or (12-21) prepared in the above step 9-1 is made to react with a compound (13) in the presence of a base, a catalyst and a ligand to produce a compound (12-12) or (12-22).

Amount of the compound (13) used is usually from 1.0 to 3.0 equivalent(s) and, preferably, from 1.0 to 1.2 equivalent(s) to one equivalent of the compound (12-12) or (12-22).

With regard to the base used in this step, its examples are potassium acetate, triethylamine, PhOK and $Na_2PO_3(OPh)$ and, among them, potassium acetate is preferred.

Amount of the base used is usually from 1.0 to 10 equivalent(s) and, preferably, 1.0 to 5.0 equivalent(s) to one equivalent of the compound (12-11) or (12-21).

With regard to the catalyst used, its examples are $PdCl_2(dppf)_2$, etc.

Amount of the catalyst used is usually from 0.01 to 1.0 equivalent and, preferably, 0.05 to 0.5 equivalent to one equivalent of the compound (12-11) or (12-21).

With regard to the ligand used, its examples are dppf, $PPh_3$ and $AsPh_3$. It is also possible to carry out the present invention even if no ligand is used.

Amount of the ligand used is usually from 1.0 mol % to 100 mol % and, preferably, from 5 mol % to 50 mol % to one equivalent of the compound (12-11) or (12-21).

With regard to the reaction solvent, although there is no particular limitation so far as it does not affect the reaction, its examples are 1,4-dioxane, DMF, toluene and ethanol and, among them, 1,4-dioxane, etc. are preferred.

Reaction temperature is usually from 50° C. to 80° C.

Reaction time in this step is usually from 2 hours to 16 hours.

The compound (12-12) or (12-22) prepared as such is able to be subjected to the next step with or without isolation and purification by a known separation/purification means such as concentration, concentration in vacuo, crystallization, extraction with solvent, re-precipitation and chromatography.

(Step 9-3)

This step is a process where the compound (12-12) or (12-22) prepared in the above step 9-2 is made to react with the compound (11) prepared in the above step 8 in the presence of a base and a catalyst to produced the compound (I-4) or (I-5) of the present invention.

The reaction in this step may be carried out under the same reaction conditions as in the above step 10.

The compound (I-4) or (I-5) prepared as such is able to be isolated and purified by a known separation/purification means such as concentration, concentration in vacuo, crystallization, extraction with solvent, re-precipitation and chromatography.

The compounds (I-7), (I-8) and (I-9) are able to be produced by the following methods.

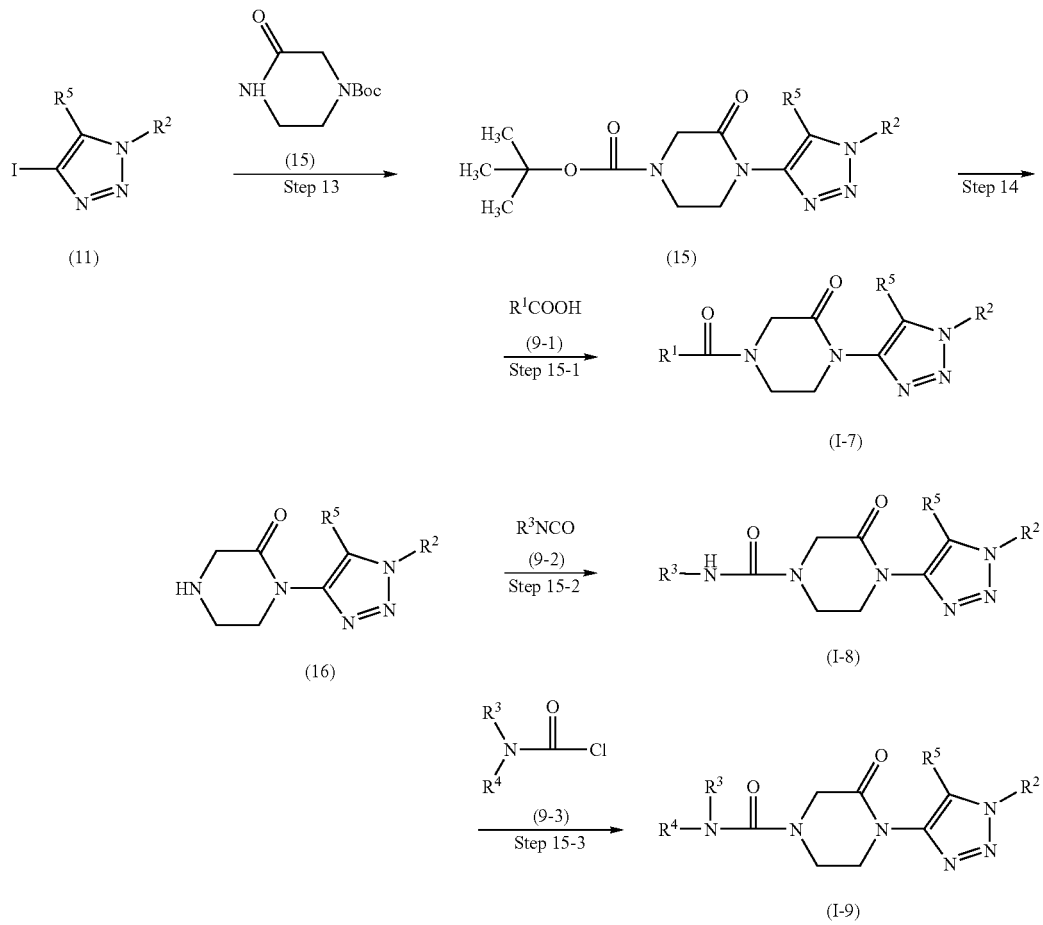

In the formulae, each of the symbols has the same meaning as defined already.

(Step 13)

This step is a process where the compound (11) prepared in the above step 8 is made to react with a compound (15) in the presence of a base, a catalyst and a ligand to produce a compound (15).

With regard to the base used in this step, its examples are potassium phosphate, sodium carbonate and potassium carbonate.

Amount of the compound (15) used is from 1 to 10 equivalent(s) and, preferably, from 1 to 3 equivalent(s) to one equivalent of the compound (11).

Amount of the base used is usually from 1 to 100 equivalent(s) and, preferably, 2 to 10 equivalents to one equivalent of the compound (11).

With regard to the catalyst used, its examples are copper iodide, copper (I) chloride and copper (11) acetate and, among them, copper iodide is preferred.

Amount of the catalyst used is usually from 1% mol to 200% mole and, preferably, from 5% mol to 20% mol to one equivalent of the compound (11).

With regard to the ligand used, its examples are trans-1,2-diamines. To be more specific, its examples are trans-1,2-cyclohexyldiamine, etc.

Amount of the ligand used is usually from 1% mol to 200% mol and, preferably, from 1% mol to 10% mol to one equivalent of the compound (11).

With regard to the reaction solvent used in the present step, although there is no particular limitation so far as it does not affect the reaction, its examples are DMF, N-methylpyrrolidone, dioxane, THF, DMSO and water and, among them, DMF, N-methylpyrrolidone and dioxane are preferred.

Reaction temperature in this step is usually from 0° C. to 150° C. and, preferably, from 50° C. to 120° C.

Reaction time in this step is usually from 30 minutes to 7 days and, preferably, from 6 hours to 12 hours.

The compound (15) prepared as such is able to be subjected to the next step with or without isolation and purification by a known separation/purification means such as concentration, concentration in vacuo, crystallization, extraction with solvent, re-precipitation and chromatography.

(Step 14)

This step is a process where the Boc group of the compound (15) prepared in the above step 13 is removed to produce a compound (16).

The reaction in this step may be carried out under the same conditions as in the above step 5.

The compound (16) prepared as such is able to be subjected to the next step with or without isolation and purification by a known separation/purification means such as concentration, concentration in vacuo, crystallization, extraction with solvent, re-precipitation and chromatography.

The compounds (I-10), (I-11) and (I-12) are able to be produced by the following methods.

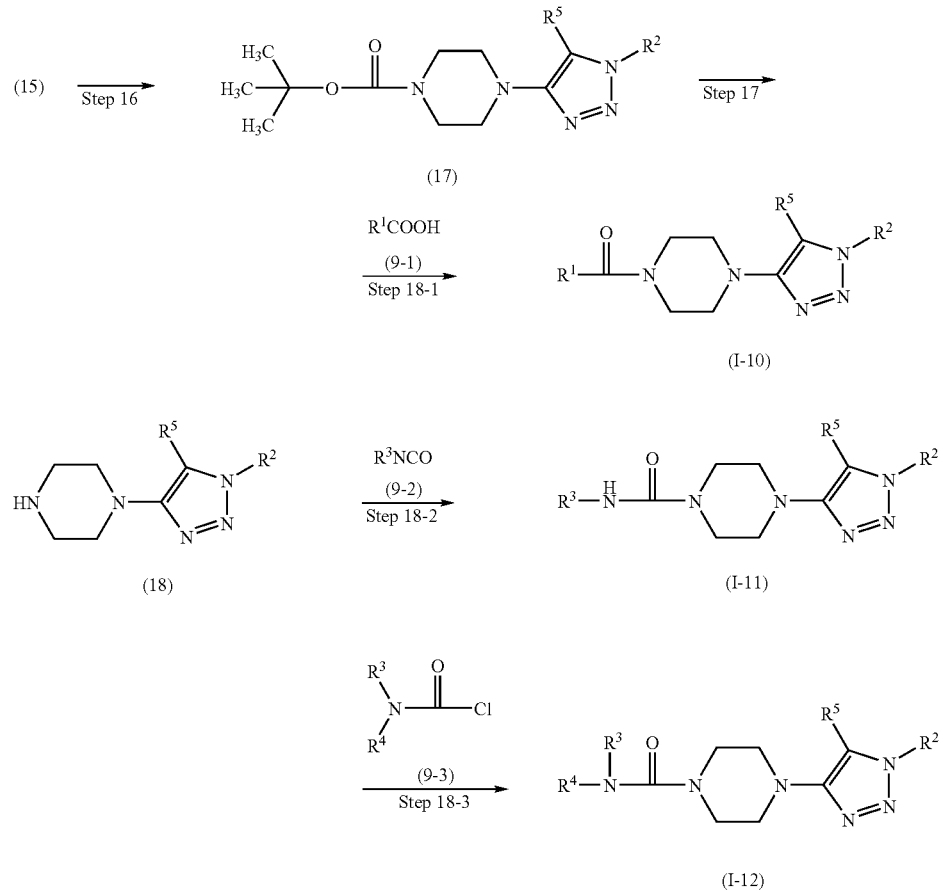

(Step 15-1)

This step is a process where the compound (16) prepared in the above step 14 is made to react with the compound (9-1) to produce a compound (I-7) of the present invention.

The reaction in this step may be carried out under the same conditions as in the above step 6-1.

The compound (I-7) prepared as such is able to be isolated and purified by a known separation/purification means such as concentration, concentration in vacuo, crystallization, extraction with solvent, re-precipitation and chromatography.

(Step 15-2)

This step is a process where the compound (16) prepared in the above step 14 is made to react with the compound (9-2) to produce a compound (I-8) of the present invention.

(Step 15-3)

This step is a process where the compound (16) prepared in the above step 14 is made to react with the compound (9-3) to produce a compound (I-9) of the present invention.

The reaction in this step may be carried out under the same conditions as in the above step 6-3.

The compound (I-9) prepared as such is able to be isolated and purified by a known separation/purification means such as concentration, concentration in vacuo, crystallization, extraction with solvent, re-precipitation and chromatography.

In the formulae, each of symbols has the same meaning as defined already.

(Step 16)

This step is a process where the compound (15) prepared in the above step 13 is reduced to produce a compound (17).

With regard to a reducing agent used in this step, its examples are $BH_3$-$Me_2S$, $BH_3$-THF and $LiAlH_4$.

Amount of the reducing agent used is usually from 1 to 100 equivalent(s) and, preferably, from 5 to 20 equivalents to one equivalent of the compound (15).

With regard to the reaction solvent used in this step, although there is no particular limitation so far as it does not affect the reaction, its specific examples are THF, diethyl ether and chloroform and, among them, THF, diethyl ether, etc. are preferred.

Reaction temperature in this step is usually from −78° C. to 100° C. and, preferably, from 0° C. to 30° C.

Reaction time in this step is usually from 10 minutes to 12 hours and, preferably, from 1 hour to 3 hours.

The compound (15) prepared as such is able to be subjected to the next step with or without isolation and purification by a known separation/purification means such as concentration, concentration in vacuo, crystallization, extraction with solvent, re-precipitation and chromatography.

(Step 17)

This step is a process where the Boc group in the compound (17) prepared in the above step 16 is removed to produce a compound (18).

The reaction in this step may follow the same reaction conditions for the above step 5.

The compound (18) prepared as such is able to be subjected to the next step with or without isolation and purification by a known separation/purification means such as concentration, concentration in vacuo, crystallization, extraction with solvent, re-precipitation and chromatography.

(Step 18-1)

This step is a process where the compound (18) prepared in the above step 17 is made to react with the compound (9-1) to produce a compound (I-10) of the present invention.

The reaction in this step may follow the same reaction conditions for the above step 6-1.

The compound (I-10) prepared as such is able to be isolate and purified by a known separation/purification means such as concentration, concentration in vacuo, crystallization, extraction with solvent, re-precipitation and chromatography.

(Step 18-2)

This step is a process where the compound (18) prepared in the above step 17 is made to react with the compound (9-2) to produce a compound (I-11) of the present invention.

The reaction in this step may follow the same reaction conditions for the above step 6-2.

(Step 18-3)

This step is a process where the compound (18) prepared in the above step 17 is made to react with the compound (9-3) to produce a compound (I-12) of the present invention.

The reaction in this step may follow the same reaction conditions for the above step 6-3.

The compound (I-12) prepared as such is able to be isolate and purified by a known separation/purification means such as concentration, concentration in vacuo, crystallization, extraction with solvent, re-precipitation and chromatography.

The above compound (18) may also be produced by the following process.

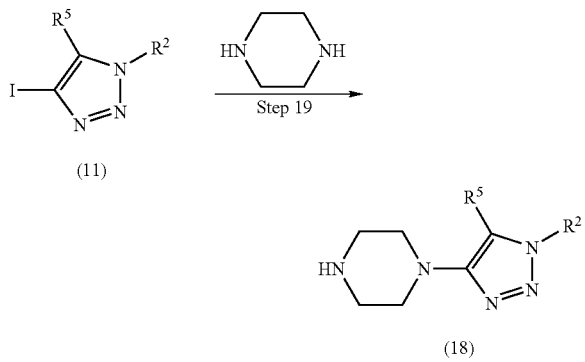

In the formulae, each of symbols has the same meaning as defined already.

(Step 19)

This step is a process where the compound (11) is made to react with piperazine in the presence of a Pd catalyst and BINAP to produce a compound (18).

With regard to the base used in this step, its examples are NaO-tert-Bu, etc.

Amount of the base used is usually from 1 to 50 equivalent(s) and, preferably, 2 to 10 equivalents to one equivalent of the compound (11).

With regard to the Pd catalyst used, its examples are $Pd(OAc)_2$ and $Pd_2(dba)_3$.

Amount of the Pd catalyst used is usually from 0.01 to 1 equivalent and, preferably, from 0.1 to 0.5 equivalent to one equivalent of the compound (11).

Amount of BINAP used in this step, it is usually from 0.01 to 1 equivalent and, preferably, from 0.1 to 0.5 equivalent to one equivalent of the compound (11).

With regard to the reaction solvent used in this step, although there is no particular limitation so far as it does not affect the reaction, its examples are toluene, dioxane, DMF and DME.

Reaction temperature in this step is usually from 0° C. to 150° C. and, preferably, from 50° C. to 100° C.

Reaction time in this step is usually from 1 to 7 day(s) and, preferably, from 2 to 10 hours.

The compound (16) prepared as such is able to be subjected to the step 18-1, 18-2 or 18-3 with or without isolation and purification by a known separation/purification means such as concentration, concentration in vacuo, crystallization, extraction with solvent, re-precipitation and chromatography.

The compound in accordance with the present invention is able to be made into a pharmaceutically acceptable salt or ester by a conventional method and is able to be produced according to a conventional method using the above formulae (I-1) to (I-12) covered by the compound (I) of the present invention.

To be more specific, when the compounds of the above (I) and (I-1) to (I-12) have a basic group derived, for example, from amino group or pyridinyl group in the molecule, it is possible to convert into the corresponding pharmaceutically acceptable salt when the compound is treated with an acid.

Examples of the acid addition salt are salt with hydrogen halide such as hydrochloride, hydrofluoride, hydrobromide and hydroiodide; salt with inorganic acid such as nitrate, perchlorate, sulfate, phosphate and carbonate; salt with a lower alkyl sulfonic acid such as methanesulfonate, trifluoromethanesulfonate and ethanesulfonate; arylsulfonate such as benzenesulfonate and p-toluenesulfonate; salt with organic acid such as fumarate, succinate, citrate, tartrate, oxalate and maleate; and salt with organic acid including amino acid such as glutamate and aspartate.

When the compound of the present invention has an acidic group in the group such as that, for example, in case it has a carboxyl group, it is also possible to convert into the corresponding pharmaceutically acceptable salt when the compound is treated with a base. Examples of the base addition salt as such are salt with alkali metal such as sodium, potassium, that with alkali earth metal such as calcium and magnesium, ammonium salt and that with organic base such as guanidine, triethylamine and dicyclohexylamine.

The compound of the present invention may also be present as any of a hydrate or a solvate of a free compound or a salt thereof.

On the other hand, conversion of salt or ester to a free compound is also able to be carried out by a conventional method.

Due to the mode of the substitutent, the compound according to the present invention may also have a steric isomer such as optical isomer, diastereomeric isomer and geometrical isomer and a tautomer. It goes without saying that all of those isomers are covered by the compound of the present invention. It also goes without saying that any mixture of those isomers is covered by the compound of the present invention.

The compound of the present invention is also able to be used as a radio-labeled substance by conversion of aromatic hydrogen of the compound into tritium, methyl group into $^3H_3C$, $^{14}CH_3$ or $^{11}CH_3$, fluorine into $^{18}F$ and carbon of carbonyl group into isotope such as $^{11}C$.

Among the compound of the present invention, a radio-labeled substance by an appropriate introduction of the above-mentioned isotope into the compound such as isopropyl 4-[1-(2-fluoropyridin-3-yl)-5-methyl-1H-[1,2,3]triazol-4-yl]-1,2,3,6-tetrahydropyridine-1-carboxylate, 4-[1-(2-fluoropyridin-3-yl)-5-methyl-1H-[1,2,3]triazol-4-yl]-1,2,3,6-tetrahydropyridine-1-carboxylic acid pyrrolidineamide, 4-[1-(2-fluoropyridin-3-yl)-5-methyl-1H-[1,2,3]triazol-4-yl]-1,2,3,6-tetrahydropyridine-1-carboxylic acid diethylamide, 4-[1-(2-fluoropyridin-3-yl)-5-methyl-1H-[1,2,3]triazol-4-yl]-1,2,3,6-tetrahydropyridine-1-carboxylic acid piperidineamide, isopropyl 4-[1-(2-chlorophenyl)-5-methyl-1H-[1,2,3]triazol-4-yl]-1,2,3,6-tetrahydropyridine-1-carboxylate, 4-[1-(2-fluoropyridin-3-yl)-5-methyl-1H-[1,2,3]triazol-4-yl]-1,2,3,6-tetrahydropyridine-1-carboxylic acid isopropylmethylamide, 4-[1-(2-fluoropyridin-3-yl)-5-methyl-1H-[1,2,3]triazol-4-yl]-1,2,3,6-tetrahydropyridine-1-carboxylic acid tert-butylamide, isopropyl 4-[1-phenyl-5-methyl-1H-[1,2,3]triazole-4-yl]-1,2,3,6-tetrahydropyridine-1-carboxylate, isopropyl 4-[1-(2-chloropyridin-3-yl)-5-methyl-1H-[1,2,3]triazol-4-yl]-1,2,3,6-tetrahydropyridine-1-carboxylate, isopropyl 4-[1-(2-fluoropyridin-5-yl)-5-methyl-1H-[1,2,3]triazol-4-yl]-1,2,3,6-tetrahydropyridine-1-carboxylate, propyl 4-[1-(2-chloropyridin-3-yl)-5-methyl-1H-[1,2,3]triazol-4-yl]-1,2,3,6-tetrahydropyridine-1-carboxylate, ethyl 4-[1-(2-chloropyridin-3-yl)-1H-[1,2,3]triazol-4-yl]-1,2,3,6-tetrahydropyridine-1-carboxylate, 2-methylpropyl 4-[1-(2-chloropyridin-3-yl)-5-methyl-1H-[1,2,3]triazol-4-yl]-1,2,3,6-tetrahydropyridine-1-carboxylate, isopropyl 4-[1-(pyridin-3-yl)-1H-[1,2,3]triazol-4-yl]-1,2,3,6-tetrahydropyridine-1-carboxylate, isopropyl 4-[5-cyano-1-phenyl-1H-[1,2,3]triazol-4-yl]-1,2,3,6-tetrahydropyridine-1-carboxylate, {4-[1-(2-chloropyridin-3-yl)-5-methyl-1H-[1,2,3]triazole-4-yl]-1,2,3,6-tetrahydropyridine-1-carboxylic acid pyrrolidineamide, 4-[1-2-fluoro-pyridin-3-yl)-1H-[1,2,3]triazol-4-yl]-1,2,3,6-tetrahydropyridine-1-carboxylic acid isopropylamide, 4-[1-(2-chloro-pyridin-3-yl)-1H-[1,2,3]triazol-4-yl]-1,2,3,6-tetrahydropyridine-1-carboxylic acid isopropylmethylamide, 4-[1-(2-chloropyridin-3-yl)-5-methyl-1H-[1,2,3]triazol-4-yl]-1,2,3,6-tetrahydropyridine-1-carboxylic acid piperidineamide, 4-[1-(2-chloropyridin-3-yl)-5-methyl-1H-[1,2,3]triazol-4-yl]-1,2,3,6-tetrahydropyridine-1-carboxylic acid methyl-tert-butylamide, 4-[1-(2-chloropyridin-3-yl)-1H-[1,2,3]triazol-4-yl]-1,2,3,6-tetrahydropyridine-1-carboxylic acid tert-butylamide, 1-{4-[1-(2-chloropyridin-3-yl)-1H-[1,2,3]triazol-4-yl]-1,2,3,6-tetrahydropyridin-1-yl}-3-methyl-1-butanone, isopropyl 4-[1-(2-fluoropyridin-3-yl)-1H-[1,2,3]triazol-4-yl]-1,2,3,6-tetrahydropyridine-1-carboxylate or isopropyl 4-[1-phenyl-5-propyl-1H-[1,2,3]triazol-4-yl]-1,2,3,6-tetra-hydropyridine-carboxylate is preferred. Among them, a radio-labeled substance by an appropriate introduction of the above-mentioned isotope into the compound such as isopropyl 4-[1-(2-fluoropyridin-3-yl)-5-methyl-1H-[1,2,3]triazol-4-yl]-1,2,3,6-tetrahydropyridine-1-carboxylate, 4-[1-(2-fluoropyridin-3-yl)-5-methyl-1H-[1,2,3]triazol-4-yl]-1,2,3,6-tetrahydropyridine-1-carboxylic acid pyrrolidineamide, 4-[1-(2-fluoropyridin-3-yl)-5-methyl-1H-[1,2,3]triazol-4-yl]-1,2,3,6-tetrahydropyridine-1-carboxylic acid diethylamide, 4-[1-(2-fluoropyridin-3-yl)-5-methyl-1H-[1,2,3]triazol-4-yl]-1,2,3,6-tetrahydropyridine-1-carboxylic acid isopropylmethylamide, 4-[1-(2-chlorophenyl)-5-methyl-1H-[1,2,3]triazol-4-yl]-1,2,3,6-tetrahydropyridine-1-carboxylate, 4-[1-(2-fluoropyridin-3-yl)-5-methyl-1H-[1,2,3]triazol-4-yl]-1,2,3,6-tetrahydropyridine-1-carboxylic acid isopropylmethylamide, 4-[1-(2-fluoropyridin-3-yl)-5-methyl-1H-[1,2,3]triazol-4-yl]-1,2,3,6-tetrahydropyridine-1-carboxylic acid tert-butylamide, isopropyl 4-[1-(2-fluoropyridin-5-yl)-5-methyl-1H-[1,2,3]triazol-4-yl]-1,2,3,6-tetrahydropyridine-1-carboxylate, 4-[1-(2-chloropyridin-3-yl)-5-methyl-1H-[1,2,3]triazol-4-yl]-1,2,3,6-tetrahydropyridine-1-carboxylic acid pyrrolidineamide and 4-[1-(2-chloropyridin-3-yl)-1H-[1,2,3]triazol-4-yl]-1,2,3,6-tetrahydropyridine-1-carboxylic acid isopropylmethylamide is more preferred.

When the compound of the present invention is clinically used, it may be prepared into a pharmaceutical preparation by addition of pharmaceutically acceptable additives depending upon the dosage form. With regard to the additives at that time, various additives which have been commonly used in the field of pharmaceutical preparations are able to be used and examples thereof are gelatin, lactose, sugar, titanium oxide, starch, crystalline cellulose, hydroxypropyl methylcellulose, carboxymethyl cellulose, corn starch, microcrystalline wax, white Vaseline, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hydrogenated castor oil, polyvinylpyrrolidone, magnesium stearate, light anhydrous silicic acid, talc, plant oil, benzyl alcohol, acacia, propylene glycol, polyalkylene glycol, cyclodextrin and hydroxypropyl cyclodextrin.

A mixture of the compound of the present invention with the above-mentioned additives is able to be used as a solid preparation (such as tablets, capsules, granules, diluted powder and suppositories) or a liquid preparation (such as syrup, elixir and injection). Such a preparation may be prepared by a conventional method in the field of pharmaceutical preparations. Incidentally, a liquid preparation may be in such as form that it is dissolved or suspended in water or other appropriate medium upon actual use. Especially in the case of an injection preparation, it may be dissolved or suspended in a physiological saline solution or a glucose solution if necessary and, if further necessary, a buffer or a preservative may be added thereto. Such a preparation may contain the compound of the present invention in an amount of 1.0 to 100% by weight and, preferably, 1.0 to 60% by weight.

The compound of the present invention may be made into a pharmaceutical preparation in accordance with, for example, the following Preparation Examples.

PREPARATION EXAMPLE 1

The compound (10 parts) of Example 1 which will be mentioned later, 15 parts of heavy magnesium oxide and 75 parts of lactose are uniformly mixed and made into powdery or granular diluted powder of not more than 350 μm. This diluted powder is filled in capsule containers to prepare capsule preparations.

PREPARATION EXAMPLE 2

The compound (45 parts) of Example 1 which will be mentioned later, 15 parts of starch, 16 parts of lactose, 21 parts of crystalline cellulose, 3 parts of polyvinyl alcohol and 30 parts of distilled water are uniformly mixed, disintegrated, granulated, dried and sieved to prepare granules where the size is 1,410 to 177 μm diameter.

2PREPARATION EXAMPLE 3

Granules are prepared by the same method as in Preparation Example 2, then 3 parts of calcium stearate is added to 96 parts of the granules and the mixture is molded with compression to give tablets each having a diameter of 10 mm.

PREPARATION EXAMPLE 4

To 90 parts of the granules prepared by a method of Preparation Example 2 are added 10 parts of crystalline cellulose and 3 parts of calcium stearate, the mixture is molded by compression to prepare tablets each having 8 mm diameter and a mixed suspension comprising syrup, gelatin and precipitated calcium carbonate is added thereto to prepare sugar-coated tablets.

When the compound of the present invention is used in clinical fields, dose and administering frequency vary depending upon sex, age, body weight and degree of symptom of the patient, type and range of the aimed treating effect, etc. Usually, in the case of oral administration, 0.01 to 100 mg/kg or, preferably, 0.03 to 1 mg/kg is administered to an adult per day once daily or by dividing into several times a day. In the case of parenteral administration, 0.001 to 10 mg/kg or, preferably, 0.001 to 0.1 mg/kg is administered once daily or by diving into several times a day.

Ordinary medical doctors of internal medicine, veterinarians or clinical doctors are able to easily decide the effective dose necessary for inhibition, suppression or stopping of the progress of the disease.

EXAMPLES

Now the present invention will be more specifically illustrated by way of the following Examples although the present invention is never limited by those Examples.

With regard to the silica gel column chromatography in the Examples, Wakogel (registered trade mark) manufactured by Wako Pure Chemicals) C-300 or KP-Sil (registered trade mark) Silica Prepacked Column manufactured by Biotarge was used. With regard to the preparatory thin-layer chromatography, Kieselgel™ 60F$_{254}$, Art. 5744 manufactured by Merck was used. With regard to the basic silica gel column chromatography, Chromatorex (registered trade mark) NH (100 to 250 mesh or 200 to 350 mesh) manufactured by Fuji Silicia Kagaku was used.

Mass spectrum was measured by an electrospray ionization method (ESI) or an atmospheric pressure chemical ionization method (APCI) using a Micromass ZQ manufactured by Waters.

With regard to an NMR spectrum, when measurement was carried out using a heavy dimethyl sulfoxide solution, dimethyl sulfoxide was used as an internal standard, the measurement was conducted using a spectrometer of a type of Gemini-200 (200 MHz; Varian), Gemini-300 (300 MHz; Varian), Mercury 400 (400 MHz; Varian) or Inova 400 (400 MHz; Varian) and total 8 values were mentioned in ppm.

Hereinafter, meanings of the abbreviations in Examples which will be mentioned later will be shown.

i-Bu: isobutyl group
n-Bu: n-butyl group
t-Bu: tert-butyl group
Me: methyl group
Et: ethyl group
Ph: phenyl group
i-Pr: isopropyl group
n-Pr: n-propyl group CDCl$_3$: heavy chloroform
CD$_3$OD: heavy methanol
DMSO-d6: heavy dimethyl sulfoxide Hereinafter, meanings of the abbreviations in nuclear magnetic resonance spectrum will be shown.

s: singlet
d: doublet
dd: double doublet
t: triplet
m: multiplet
br: broad
q: quartet
J: coupling constant
Hz: Herz

Example 1

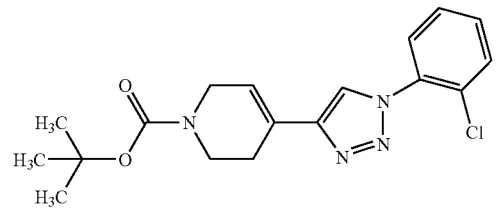

tert-Butyl 4-[1-(2-chlorophenyl)-1H-[1,2,3]-triazol-4-yl]-1,2,3,6-tetrahydropyridine-1-carboxylate 1) Production of 1-azido-2-chlorobenzene 2-Chlorophenylhydrazine hydrochloride (1.0 g) suspended in 6.0 ml of diethyl ether was dropped into 5 ml of concentrated hydrochloric acid cooled at 0° C. After the reaction solution was stirred for 10 minutes, 462 mg of sodium nitrite dissolved in 2.0 ml of water was dropped into the reaction solution and the mixture was stirred for 2 hours together with raising the temperature up to room temperature. Water was added to the reaction solution, the mixture was extracted with ethyl acetate and the ethyl acetate layer washed with a saturated aqueous saline solution and dried over sodium sulfate. The solvent was evaporated in vacuo to give 506 mg of the title compound as a red oily crude product.

2) Production of tert-butyl 4-[1-(2-chlorophenyl)-1H-[1,2,3]-triazol-4-yl]-1,2,3,6-tetrahydropyridine-1-carboxylate The compound (206 mg) prepared in the above 1) and 300 mg of tert-butyl 4-ethynyl-1,2,3,6-tetrahydropyridine-1-carboxylate were dissolved in 8 ml of toluene and stirred at 120° C. for one night. The resulting solution was cooled down to room temperature, the solvent was evaporated in vacuo and the resulting residue was purified by a preparative thin-layer silica gel chromatography (hexane:ethyl acetate=2:1) to give 32.3 mg of the title compound as a white solid.

$^1$HNMR (400 MHz, CDCl$_3$) δ: 1.52 (9H, s), 2.58-2.62 (2H, m), 3.66 (2H, m), 4.11 (1H, s), 6.52 (1H, br), 7.41-7.44 (2H, m), 7.54-7.60 (2H, m), 7.84 (1H, s)

ESI-MS Found: m/z 361.2 [M+H]+.

Example 2

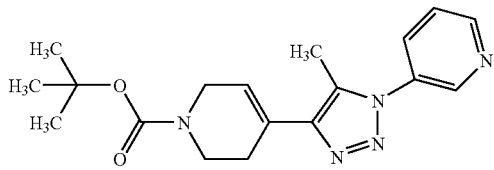

tert-Butyl 4-[5-methyl-1-(pyridin-3-yl)-1H-[1,2,3]-triazol-4-yl]-1,213,6-tetrahyropyridine-1-carboxylate

1) Production of 3-azidopyridine

Sodium azide (1.5 g) dissolved in 5 ml of water was dropped into a solution of 2.0 g of 3-aminopyridine in 15 ml of 10% hydrochloric acid under cooling with ice. After the reaction solution was stirred for 20 minutes under cooling with ice, 1.8 g of sodium nitrite dissolved in 5 ml of water was dropped in the reaction solution. After temperature of the reaction solution was raised up to room temperature, it was stirred for 1 hour. The reaction solution was diluted with chloroform, washed with water and then with a saturated saline solution and dried over sodium sulfate. The solvent was evaporated in vacuo to give 2.5 g of the title crude compound as a brown oily substance.

2) Production of 1-(3-pyridyl)-5-methyl-4-trimethyl-silyl-1H-[1,2,3]triazole Under a nitrogen atmosphere, 6.0 ml of 1-(trimethylsilyl)-1-propynyl was added to a solution of 1.5 g of the compound prepared in the above 1) in 20 ml of toluene and the mixture was stirred at 120° C. for 6 hours. The resulting solution was cooled down to room temperature, the solvent was concentrated in vacuo and the resulting residue was purified by a silica gel column chromatography (hexane:diethyl ether=90:10) to give 1.4 g of the title compound as a yellow oily substance.

3) Production of 1-(3-pyridyl)-5-methyl-4-iodo-1H-[1,2,3]triazole

In a nitrogen atmosphere, 1.3 g of silver tetrafluoroborate and 2.7 g of boron were successively added, under cooling with ice, to a solution of 1.4 g of the compound prepared in the above 2) in 70 ml of methanol and the mixture was stirred at room temperature for one night. After addition of an aqueous solution of sodium thiosulfate, the product was extracted with chloroform and the organic layer washed with water and dried over sodium sulfate. The solvent was evaporated in vacuo and the resulting residue was purified by a silica gel column chromatography (chloroform:methanol=20:1) to give 500 mg of the title compound as a light yellow solid.

$^1$HNMR (300 MHz, CDCl$_3$) δ: 2.26 (3H, s), 7.54 (1H, ddd, J=0.8, 4.8, 8.8 Hz), 7.87 (1H, ddd, J=1.6, 2.8, 8.4 Hz), 8.76-8.79 (2H, m)

ESI-MS Found: m/z 287.1 [M+H]+.

4) Production of tert-butyl 4-[5-methyl-1-(pyridin-3-yl)-1H-[1,2,3]-triazol-4-yl]-1,2,3,6-tetrahydropyridine-1-carboxylate In a nitrogen atmosphere, 100 mg of the compound prepared in the above 3) and 80 mg of tert-butyl 4-(4,4,5,5-tetramethyl-[1,3,2]dioxaboran-yl)-1,2,3,6-tetrahydropyridine-1-carboxylate were dissolved in 5 ml of dimethylformamide, 100 mg of potassium carbonate and 30 mg of [1,1'-bis(diphenylphosphino)ferrocene]dichloropalladium were added and the mixture was stirred at 80° C. for one night. After water was added, the product was extracted with ethyl acetate and the organic layer was washed with water and dried over sodium sulfate. The residue obtained by evaporation of the solvent in vacuo was purified by a preparatory thin-layer silica gel chromatography (chloroform:methanol=9:1) to give 10 mg of the title compound as a white solid.

$^1$HNMR (400 MHz, CDCl$_3$) δ: 1.50 (9H, s), 2.42 (3H, s), 2.71-2.76 (2H, m), 3.68 (2H, t, J=5.6, 11.2 Hz), 4.13 (2H, d, 2.8 Hz), 6.03 (1H, brs), 7.54 (1H, ddd, J=0.8, 4.8, 8.4 Hz), 7.87 (1H, ddd, J=1.6, 2.8, 8.4 Hz), 8.76-8.79 (2H, m)

ESI-MS Found: m/z 342.3 [M+H]+.

Example 3

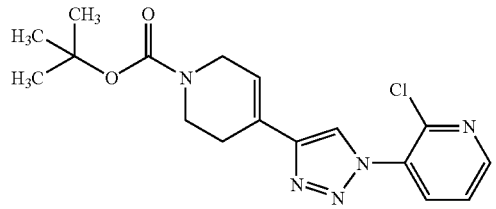

tert-Butyl 4-[1-(2-chloropyridin-3-yl)-1H-[1,2,3]-triazol-4-yl]-1,2,3,6-tetrahydropyridine-1-carboxylate

1) Production of 3-azido-2-chloropyridine

In a nitrogen atmosphere, a solution of 6.3 ml of diisopropylamine in 40 ml of tetrahydrofuran was cooled at −78° C. and, after that, a 1.58M solution of n-butyl lithium in 28 ml of hexane was dropped into this solution. After temperature of the reaction solution was raised to 0° C., it was stirred for 5 minutes, cooled down to −78° C. again and a solution of 5.09 g of 2-chloropyridine in 10 ml of tetrahydrofuran was added thereto. After it was stirred for 10 minutes at −78° C., a solution of 8.9 g of 2,4,6-triisopropylbenzene sulfonazide in 20 ml of tetrahydrofuran was added thereto, the mixture was stirred, temperature thereof was raised to −60° C. and water was added thereto to stop the reaction. The product was extracted with ethyl acetate and dried over sodium sulfate and the solvent was evaporated in vacuo. The resulting residue was purified by a silica gel column chromatography (hexane:ethyl acetate=80:20) to give 4.80 g of the title compound as a brownish gray oily crude product.

2) Production of tert-butyl 4-[1-(2-chloropyridin-3-yl)-1H-[1,2,3]-triazol-4-yl]-1,2,3,6-tetrahydropyridine-1-carboxylate The same operation as in Example 1 was carried out using the azide compound prepared in 1) and tert-butyl 4-ethynyl-1,2,3,6-tetrahydropyridine-1-carboxylate to give the title compound as a white solid.

$^1$HNMR (300 MHz, CDCl$_3$) δ: 1.50 (9H, s), 2.52-2.62 (2H, m), 3.60-3.71 (2H, m), 4.08-4.18 (2H, m), 6.51-6.60 (1H, m), 7.49 (1H, dd, J=5.8, 7.9 Hz), 7.99 (1H, s), 8.04 (1H, dd, J=1.8, 7.9 Hz), 8.56 (1H, dd, J=1.8, 5.8 Hz)

ESI-MS Found: m/z 306.0 [M-t-Bu+H]+.

Example 4

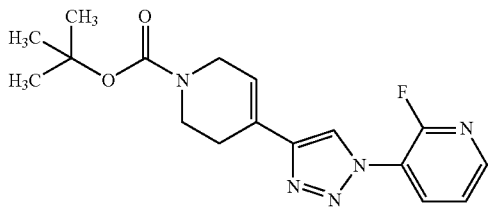

tert-Butyl 4-[1-(2-fluoropyridin-3-yl)-1H-[1,2,3]-triazol-4-yl]-1,2,3,6-tetrahydropyridine-1-carboxylate

1) Production of 3-azido-2-fluoropyridine

Under nitrogen atmosphere, a solution of 5.3 ml of diisopropylamine in 100 ml of tetrahydrofuran was cooled at −78° C. and, after that, a 1.58M solution of n-butyl lithium in 24 ml of hexane was dropped into this solution. After temperature of the reaction solution was raised to 0° C., it was stirred for 5 minutes, cooled down to −78° C. again and a solution of 3.7 g of 2-fluoropyridine in 10 ml of tetrahydrofuran was added thereto. After it was stirred for 10 minutes at −78° C., a solution of 8.9 g of n-dodecylbenzene sulfonamide in 10 ml of tetrahydrofuran was added thereto, the mixture was stirred, temperature thereof was raised to −60° C. and water was added thereto to stop the reaction. The product was extracted with ethyl acetate and dried over sodium sulfate and the solvent was evaporated in vacuo. The resulting residue was purified by a silica gel column chromatography (hexane:ethyl acetate=75:25) to give 3.02 g of the title compound as a brownish gray oily crude product.

2) Production of tert-butyl 4-[1-(2-fluoropyridin-3-yl)-1H-[1,2,3]-triazol-4-yl]-1,2,3,6-tetrahydropyridine-1-carboxylate The same operation as in Example 1 was carried out using the azide compound prepared in 1) and tert-butyl 4-ethynyl-1,2,3,6-tetrahydropyridine-1-carboxylate to give the title compound as a white solid.

$^1$HNMR (300 MHz, CDCl$_3$) δ: 1.50 (9H, s), 2.52 (2H, m), 3.68 (2H, t, J=5.8 Hz), 4.08-4.18 (2H, m), 6.51-6.60 (1H, m), 7.40-7.48 (1H, m), 8.02-8.08 (1H, m), 8.28-8.32 (1H, m), 8.46-8.57 (1H, m)

ESI-MS Found: m/z 290.3 [M-t-Bu+H]+.

Example 5

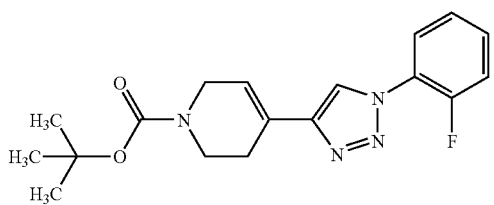

tert-Butyl 4-[1-(2-fluorophenyl)-1H-[1,2,3]triazol-4-yl]-1,2,3,6-tetrahydropyridine-1-carboxylate

1) Production of 1-azido-2-fluorobenzene

Sodium nitrite (510 mg) dissolved in 2 ml of water was dropped, under cooling with ice, into a solution of 1.0 g of 2-fluorophenylhydrazine hydrochloride in 5 ml of concentrated hydrochloric acid and 6 ml of diethyl ether. Temperature of the reaction solution was raised to room temperature followed by stirring for 2 hours. The reaction solution was diluted with diethyl ether, washed with water and then with a saturated saline solution and dried over sodium sulfate. The solvent was evaporated in vacuo to give 402 mg of the crude title compound as a brown oily substance.

2) Production of 4-[1-(2-fluorophenyl)-1H-[1,2,3]-triazol-4-yl]-1,2,3,6-tetrahydropyridine-1-carboxylate The same operation as in Example 1 was carried out using the azide compound prepared in 1) and tert-butyl 4-ethynyl-1,2,3,6-tetrahydropyridine-1-carboxylate to give the title compound as a white solid.

$^1$HNMR (300 MHz, CDCl$_3$) δ: 1.50 (9H, s), 2.02-2.12 (2H, m), 3.67 (2H, t, J=5.8 Hz), 4.08-4.16 (2H, m), 6.48-6.56 (1H, m), 7.22-7.48 (3H, m), 7.91-8.01 (2H, m)

ESI-MS Found: m/z 289.2 [M-t-Bu+H]+.

Example 6

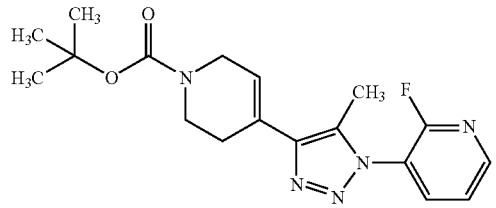

tert-Butyl 4-[1-(2-fluoropyridin-3-yl)-5-methyl-1H-[1,2,3]triazol-4-yl]-1,2,3,6-tetrahydropyridine-1-carboxylate

1) Production of 1-(2-fluoropyridin-3-yl)-5-methyl-4-trimethylsilyl-1H-[1,2,3]triazole To a solution of 1.70 g of the azide compound prepared in Example 4 in 5.0 ml of toluene was added 5.0 g of trimethyl (1-propynyl)silane followed by stirring for one night under heating to reflux. The resulting solution was cooled down to room temperature and the solvent was evaporated in vacuo followed by purifying with a silica gel column chromatography (hexane:ethyl acetate=75:25) to give 1.70 g of the title compounds as a colorless oily substance.

2) Production of 1-(2-fluoropyridin-3-yl)-5-methyl-4-iodo-1H-[1,2,3]-triazole The compound (512 mg) prepared in 1) was dissolved in 20 ml of tetrahydrofuran, 292 mg of silver tetrafluoroborate and 760 mg of iodine were added thereto and the resulting solution was stirred for 3.0 hours at room temperature. The reaction solution was filtered through a Celite, a saturated aqueous solution of sodium thiosulfate was added to the filtrate and the solvent was evaporated in vacuo. Water was added to the residue, the mixture was extracted with ethyl acetate and the ethyl acetate layer washed with a saturated aqueous saline solution and dried over sodium sulfate. The solvent was evaporated in vacuo and the residue was separated/purified by a silica gel column chromatography (chloroform/methanol=50/1) and then by a basic silica gel column chromatography (hexane/ethyl acetate=3/1) to give 485 mg of the title compound as a white solid.

¹HNMR (300 MHz, CDCl₃) δ: 2.31 (3H, d, J=2.0 Hz), 7.41-7.50 (1H, m), 7.92-8.08 (1H, m), 8.40-8.50 (1H, m)

3) Production of tert-butyl 4-[1-(2-fluoropyridin-3-yl)-5-methyl-1H-[1,2,3]triazol-4-yl-1,2,3,6-tetrahydropyridine-1-carboxylate The same operation as in Example 2 was carried out using the iodine compound prepared in 2) and tert-butyl 4-(4,4,5,5-tetramethyl-[1,3,2]dioxaboran-2-yl)-1,2,3,6-tetrahydropyridine-1-carboxylate to give the title compound as a light yellow amorphous substance.

¹HNMR (300 MHz, CDCl₃) δ: 1.50 (9H, s), 2.34 (3H, d, J=2.1 Hz), 2.69-2.80 (2H, m), 3.61-3.72 (2H, m), 4.09-4.18 (2H, m), 6.01-6.09 (1H, m), 7.40-7.50 (1H, m), 7.95-8.04 (1H, m), 8.39-8.48 (1H, m)

ESI-MS Found: m/z 360.4 [M+H]+.

Example 7

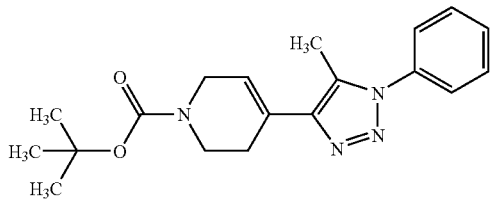

tert-Butyl 4-[1-phenyl-5-methyl-1H-[1,2,3-triazol-4-yl]-1,2,3,6-tetrahydropyridine-1-carboxylate 1) Production of phenyl azide Concentrated hydrochloric acid (20 ml) was cooled at 0° C. and a solution of 2.0 ml of phenylhydrazine in 7.0 ml of diethyl ether was dropped thereinto. After stirring for 10 minutes, a solution of 1.70 g of sodium nitrite dissolved in 2.0 ml of water was dropped thereinto and the mixture was stirred for 1 hour together with raising the temperature up to room temperature. Water was added to the reaction solution, the mixture was extracted with ethyl acetate and the ethyl acetate layer washed with a saturated saline solution and dried over sodium sulfate. The solvent was evaporated in vacuo to give 961 mg of the title compound as a red oily crude product.

2) Production of tert-butyl 4-hydroxy-4-(1-propynyl)-piperidine-1-carboxylate tert-Butyl 4-oxopiperidine-1-carboxylate (2.99 g) was dissolved in 30 ml of tetrahydrofuran, cooled down to −78° C., 40 ml of a 0.5N solution of 1-propynyl magnesium bromide in 40 ml of tetrahydrofuran was dropped thereinto and temperature of the mixture was raised to room temperature followed by stirring for one night. A saturated aqueous solution of sodium hydrogen carbonate was added to the reaction solution to stop the reaction and the product was extracted with ethyl acetate, washed with a saturated aqueous solution of ammonium chloride and dried over sodium sulfate. The solvent was evaporated in vacuo and the resulting residue was purified by a silica gel column chromatography (hexane/ethyl acetate=4/1) to give 1.41 g of the title compound as a crude product.

3) Production of tert-butyl 4-(1-propynyl)-1,2,3,6-tetrahydropyridine-1-carboxylate The compound (720 mg) prepared in the above 2) was dissolved in 20 ml of chloroform, the solution was cooled down to 0° C., 0.84 ml of triethylamine and 0.29 ml of methanesulfonyl chloride were added thereto and temperature of the mixture was raised to room temperature followed by stirring for one night. To the reaction solution was added a saturated aqueous solution of sodium hydrogen carbonate to stop the reaction and the product was extracted with ethyl acetate, washed with a saturated aqueous solution of ammonium chloride was added and dried over sodium sulfate. The solvent was evaporated to give 590 mg of the title product.

¹HNMR (300 MHz, CDCl₃) δ: 1.43 (9H, s), 1.93 (3H, s), 2.10-2.29 (2H, m), 3.41-3.51 (2H, m), 3.87-3.98 (2H, m), 5.90 (1H, br)

4) Production of tert-butyl 4-[1-phenyl-5-methyl-1H-[1,2,3]triazol-4-yl]-1,2,3,6-tetrahydropyridine-1-carboxylate The above-prepared phenyl azide (214 mg) and 200 mg of tert-butyl 4-(1-propynyl)-1,2,3,6-tetrahydropyridine-1-carboxylate prepared in 3) were dissolved in 3 ml of toluene and the solution was stirred at 120° C. for one night. The resulting solution was cooled down to room temperature, the solvent was evaporated in vacuo and the resulting residue was purified by a preparative thin-layer silica gel chromatography (hexane:ethyl acetate=2:1) to give 9.4 mg of the title compound as a white solid.

¹HNMR (400 MHz, CDCl₃) δ: 1.50 (9H, s), 2.37 (3H, s), 2.74-2.76 (2H, m), 3.66 (2H, t, J=5.6 Hz), 4.12 (2H, br), 6.00 (1H, br), 7.42-7.56 (5H, m)

ESI-MS Found: m/z 341.3 [M+H]+.

Example 8

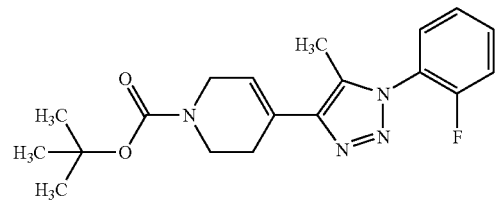

tert-Butyl 4-[1-(2-fluorophenyl)-5-methyl-1H-[1,2,3]-triazol-4-yl]-1,2,3,6-tetrahydropyridine-1-carboxylate 1) Production of 1-azido-2-fluorobenzene Sodium nitrite (510 mg) dissolved in 2 ml of water was dropped, under cooling with ice, into a solution of 1.0 g of 2-fluorophenylhydrazine hydrochloride in 5 ml of concentrated hydrochloric acid and 6 ml of diethyl ether. Temperature of the reaction solution was raised to room temperature followed by stirring for 2 hours. The reaction solution was diluted with diethyl ether, washed with water and then with a saturated saline solution and dried over sodium sulfate. The solvent was evaporated in vacuo to give 400 mg of the title compound as a brown oily crude product.

2) Production of 1-(2-fluorophenyl)-5-methyl-4-tributylstannyl-1H-[1,2,3]triazole Tributyl (1-propynyl)tin (2.9 g) was added to a solution of 400 mg of the compound prepared in the above 1) in 5 ml of toluene followed by stirring at 120° C. for 4.5 hours. The resulting solution was cooled down to room temperature, a saturated aqueous solution of potassium fluoride was added to the reaction solution and the mixture was extracted with ethyl acetate, washed with a saturated saline solution and dried over sodium sulfate. The solvent was evaporated in vacuo and the residue was purified by a silica gel column chromatography (hexane:ethyl acetate=90:10) to give 680 mg of the title compound as a yellow oil product.
$^1$HNMR (300 MHz, CDCl$_3$) δ: 0.90 (9H, t, J=7.5 Hz), 1.19-1.29 (12H, m), 1.35-1.66 (6H, m) 2.32 (3H, s), 7.19-7.24 (2H, m), 7.42-7.49 (2H, m)
APCI-MS Found: m/z 468.5 [M+H]+.

3) Production of tert-butyl 4-[1-(2-fluorophenyl)-5-methyl-1H-[1,2,3]triazol-4-yl]-1,2,3,6-tetrahydropyridine-1-carboxylate Under nitrogen atmosphere, a solution of 32 mg of tert-butyl 4-trifluorosulfonyloxy-1,2,3,6-tetrahydropyridine-1-carboxylate, 30 mg of 1-(2-fluorophenyl)-5-methyl-4-tributylstannyl-1H-[1,2,3]-triazole which is a tin reagent prepared in the above 2) and 2 mg of dichlorobistriphenyl phosphine palladium in 2.0 ml of dioxane was stirred at 110° C. for 4 hours. The reaction solution was cooled down to room temperature and filtered through Celite to remove insoluble matters. The solvent was evaporated in vacuo and the residue was separated and purified by a thin-layer chromatography (ethyl acetate/hexane=1/2) to give 4.87 mg of the title compound as a white solid.
$^1$HNMR (400 MHz, CDCl$_3$) δ: 1.50 (9H, s), 2.30 (3H, d, t=1.6 HZ), 2.74-2.77 (2H, m), 3.65-3.68 (2H, m), 4.12 (2H, br), 6.03 (1H, br), 7.25-7.35 (2H, m), 7.47-7.50 (2H, m)
ESI-MS Found: m/z 359.3 [M+H]+.

Example 9

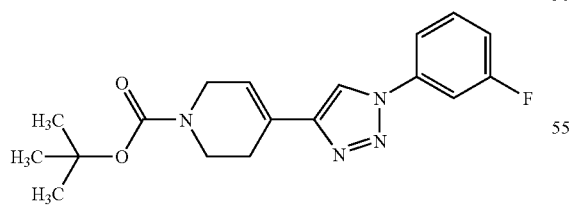

tert-Butyl 4-[1-(2-fluorophenyl)-1H-[1,2,3]triazol-4-yl]-1,2,3,6-tetrahydropyridine-1-carboxylate 1) Production of 1-azido-3-fluorobenzene Sodium nitrite (262 mg) dissolved in 1.0 ml of water was dropped, under cooling with ice, into a solution of 500 mg of 3-fluorophenylhydrazine hydrochloride in 2.5 ml of concentrated hydrochloric acid and 3.0 ml of diethyl ether. Temperature of the reaction solution was raised to room temperature followed by stirring for 3 hours. The reaction solution was diluted with diethyl ether, washed with water and then with a saturated saline solution and dried over sodium sulfate. The solvent was evaporated in vacuo to give 252 mg of the title compound as a brown oily crude product.

2) Production of tert-butyl 4-[1-(3-fluorophenyl)-1H-[1,2,3]triazol-4-yl]1,2,3,6-tetrahydropyridine-1-carboxylate The same operation as in Example 1 was carried out using the azido compound prepared in 1) and tert-butyl 4-ethynyl-1,2,3,6-tetrahydropyridine-1-carboxylate to give the tile compound as a white solid.
$^1$HNMR (300 MHz, CDCl$_3$) δ: 1.50 (9H, s), 2.51-2.60 (2H, m), 3.68 (2H, t, J=5.4 Hz), 4.08-4.16 (2H, m), 6.50-6.58 (1H, m), 7.08-7.18 (1H, m), 7.42-7.57 (3H, m), 7.85 (1H, s)
ESI-MS Found: m/z 289.1 [M-t-Bu+H]+.

Example 10

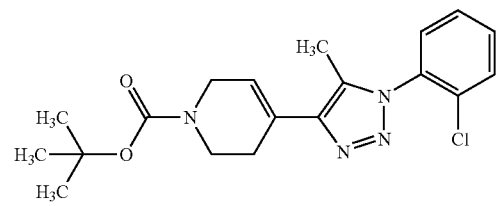

tert-Butyl 4-[1-(2-chlorophenyl)-5-methyl-1H-[1,2,3]-triazol-4-yl]-1,2,3,6-tetrahydropyridine-1-carboxylate The same operation as in Example 7 was carried out using the azide compound prepared in Example 1 and tert-butyl 4-(1-propynyl)-1,2,3,6-tetrahydropyridine-1-carboxylate prepared in 3) of Example 7 to give the title compound as a white solid.
$^1$HNMR (300 MHz, CDCl$_3$) δ: 1.50 (9H, s), 2.25 (3H, s), 2.71-2.81 (2H, m), 3.62-3.72 (2H, m), 4.08-4.18 (2H, m), 6.02-6.10 (1H, m), 7.40-7.62 (4H, m)
ESI-MS Found: m/z 375.3 [M+H]+.

Example 11

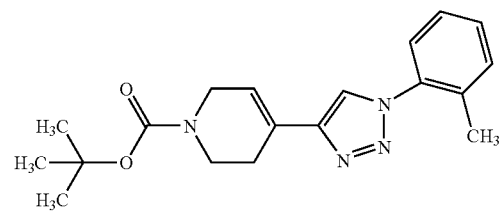

tert-butyl 4-[1-(2-methylphenyl)-1H-[1,2,3]triazol-4-yl]-1,2,3,6-tetrahydropyridine-1-carboxylate 1) Production of 1-azido-2-methylbenzene Reaction was carried out by the same method as in Example 1-1 except that o-tolylhydrazine was used in place of 2-chlorophenylhydrazine hydrochloride used in Example 1-1 to give the title compound.

2) Production of tert-butyl 4-[1-(2-methylphenyl)-1H-[1,2,3]triazol-4-yl]-1,2,3,6-tetrahydropyridine-1-carboxylate Reaction was carried out by the same method as in Example 1-2 except that 1-azido-2-methylbenzene was used in place of 1-azido-2-chlorobenzene used in Example 1-2 to give the title compound.

$^1$HNMR (400 MHz, CDCl$_3$) δ: 1.49 (9H, s), 2.22 (3H, s), 2.58-2.62 (2H, m), 3.66 (2H, t) 4.11 (1H, s), 6.50 (1H, br), 7.25-7.40 (4H, m), 7.62 (1H, s)

ESI-MS Found: m/z 341.3 [M+H]+.

Example 12

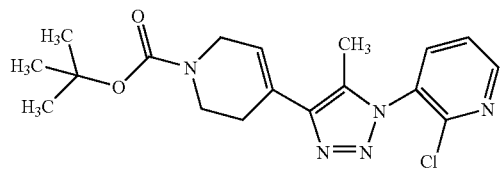

tert-Butyl 4-[1-(2-chloropyridin-3-yl)-5-methyl-1H-[1,2,3]triazol-4-yl]-1,2,3,6-tetrahydropyridine-1-carboxylate 1) Production of 1-(2-chloropyrin-3-yl)-5-methyl-4-trimethylsilyl-1H-[1,2,3]-triazole To a solution of 2.10 g of the azide compound prepared in Example 3 in 15 ml of toluene was added 10 g of trimethyl (1-propynyl)silane followed by stirring for one night under heating to reflux. The resulting solution was cooled down to room temperature, the solvent was evaporate in vacuo and purification was a silica gel column chromatography (hexane:ethyl acetate=75:25) to give 1.35 g of the title compound as a colorless oily product.

2) Production of 1-(2-chloropyridin-3-yl)-5-methyl-4-iodo-1H-[1,2,3]triazole

The compound (1.34 g) prepared in 1) was dissolved in 60 ml of methanol and 2.04 g of silver tetrafluoroborate and 2.54 g of iodine were added to the above solution followed by stirring for 1.5 hours at room temperature. The reaction solution was filtered through Celite, a saturated aqueous solution of sodium thiosulfate was added to the filtrate and the solvent was evaporated in vacuo. Water was added to the residue, the mixture was extracted with ethyl acetate and the ethyl acetate layer was washed with a saturated saline solution and dried over sodium sulfate. The solvent was evaporated in vacuo and the residue was separate and purified by a silica gel column chromatography (hexane/ethyl acetate=2/1) to give 1.43 g of the title compound as a white solid.

$^1$HNMR (300 MHz, CDCl3) δ: 2.27 (3H, s,), 7.45-7.52 (1H, m), 7.76-8.02 (1H, m), 8.60-8.67 (1H, m)

3) Production of tert-butyl 4-[1-(2-chloropyridin-3-yl)-5-methyl-1H-[1,2,3]triazol-4-yl]-1,2,3,6-tetrahydropyridine-1-carboxylate The same operation as in Example 2 was carried out using the iodine compound prepared in 2) and tert-butyl 4-(4,4,5,5-tetramethyl-[1,3,2]dioxaboran-2-yl)-1,2,3,6-tetrahydropyridine-1-carboxylate to give the title compound as a light yellow amorphous product.

$^1$HNMR (300 MHz, CDCl$_3$) δ: 1.50 (9H, s), 2.29 (3H, s), 2.70-2.80 (2H, m), 3.52-3.72 (2H, m), 4.10-4.18 (2H, m), 6.03-6.11 (1H, m), 7.49 (1H, dd, J=7.8, 14.8 Hz), 7.81 (1H, dd, J=1.8, 7.8 Hz), 8.62 (1H, dd, J=1.8, 14.8 Hz)

ESI-MS Found: m/z 376.3 [M+H]+.

Example 13

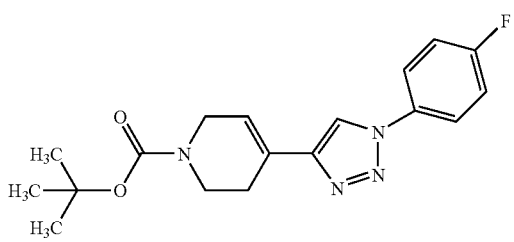

J-000142221-000S001 tert-Butyl 4-[1-(4-fluorophenyl)-1H-[1,2,3]triazol-4-yl]-1,2,3,6-tetrahydropyridine-1-carboxylate 1) Production of 1-azido-4-fluorobenzene A solution of 262 mg of sodium nitrite dissolved in 2.0 ml of water was dropped into a solution of 3.09 g of 4-fluorophenylhydrazine hydrochloride in 20 ml of concentrated hydrochloric acid and 10 ml of diethyl ether under cooling with ice. Temperature of the reaction solution was raised to room temperature followed by stirring for 3 hours. The reaction solution was diluted with diethyl ether, washed with water and then with a saturated saline solution and dried over sodium sulfate. The solvent was evaporated in vacuo to give 1.01 g of the crude title compound as a brown oily substance.

2) Production of tert-butyl 4-[1-(4-fluorophenyl)-1H-[1,2,3]triazol-4-yl]-1,2,3,6-tetrahydropyridine-1-carboxylate The same operation was in Example 1 was carried out using the azide compound prepared in 1) and tert-butyl 4-ethynyl-1,2,3,6-tetrahydropyridine-1-carboxhlate to give the title compound as a white solid.

$^1$HNMR (300 MHz, CDCl$_3$) δ: 1.50 (9H, s), 2.51-2.65 (2H, m), 3.67 (2H, t, J=5.6 Hz), 4.06-4.16 (2H, m), 6.42-6.58 (1H, m), 7.17-7.30 (2H, m), 7.65-7.75 (2H, m), 7.82 (1H, s)

ESI-MS Found: m/z 289.2 [M-t-Bu+H]+.

Example 14

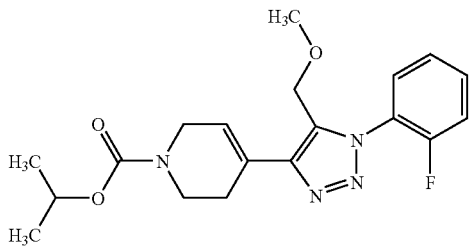

Isopropyl 4-[1-(2-fluorophenyl)-5-methoxymethyl-1H-[1,2,3]triazol-4-yl]-1,2,3,6-tetrahydropyridine-1-carboxylate

1) Production of (3-methoxy-1-propynyl)-trimethyl-silane

In a nitrogen atmosphere, a solution of 0.84 ml of 3-methoxypropyne in tetrahydrofuran was cooled at −78° C., 7.0 ml of a 1.57M solution of n-butyl lithium in hexane was dropped thereinto and a mixture was stirred at 0° C. for 1 hour (solution 1). In another container, a solution of 2.46 ml of trimethylsilyl chloride in tetrahydrofuran was cooled at −78° C., the above-prepared solution 1 was dropped thereinto and the mixture was stirred for 1 hour together with raising the temperature. A saturate aqueous solution of ammonium chloride was added to the reaction solution, the mixture was extracted with ethyl acetated and the extract washed with a saturate saline solution and dried over sodium sulfate. The solvent was evaporated in vacuo and the residue was purified by a silica gel column chromatography (hexane:ethyl acetate=20:1) to give 1.2 g of the title compound as a yellow oil substance.

$^1$HNMR (400 MHz, CDCl$_3$) δ: 0.18 (9H, s), 3.37 (3H, s), 4.07 (2H, s)

2) Production of 1-(2-fluorophenyl)-5-methoxymethyl-4-trimethylsilanyl-1H-[1,2,3]triazole A reaction was carried out by the method mentioned in Example 8-2 except that 1-azido-2-fluorobenzene was used in place of 1-azido-2-chlorobenzene used in Example 1-2 and that (3-methoxy-1-propynyl)-trimethylsilane prepared in the above 1) was used in place of tributyl (1-propynyl)tin used in Example 8-2 to give the title compound.

3) Production of 1-(2-fluorophenyl)-4-iodo-5-methoxymethyl-4-trimethylsilanyl-1H-[1,2,3]triazole 1-(2-Fluorophenyl)-5-methoxymethyl-4-trimethyl-silanyl-1H-[1,2,3]triazole (40 mg) which is the compound prepared in the above 2) was dissolved in 5.0 ml of tetrahydrofuran, 360 mg of iodine and 55 mg of silver tetrafluoroborate were added thereto and the mixture was stirred at room temperature for one night. The reaction solution was filtered through Celite, a saturated aqueous solution of sodium thiosulfate was added to the filtrate and the solvent was evaporated in vacuo. Water was added to the residue, the mixture was extracted with ethyl acetate and the ethyl acetate layer washed with a saturated saline solution and dried over sodium sulfate. After the solvent was evaporated in vacuo, the residue was separated and purified by a silica gel column chromatography (hexane/ethyl acetate=2/1) to give 21.5 mg of the title compound as a white solid.

$^1$HNMR (400 MHz, CDCl$_3$) δ: 3.22 (3H, s), 4.44 (2H, d, J=0.4 Hz), 7.26-7.34 (2H, m), 7.33-7.54 (2H, m)

ESI-MS Found: m/z 334.0 [M+H]+.

4) Production of tert-butyl 4-[1-(2-fluorophenyl)-5-methoxymethyl-1H-[1,2,3]triazol-4-yl]-1,2,3,6-tetrahydropyridine-1-carboxylate In a nitrogen atmosphere, 21 mg of 1-(2-fluorophenyl)-4-iodo-5-methoxymethyl-4-trimethyl-silanyl-1H-[1,2,3]triazole prepared in the above 3), 29 mg of tert-butyl 4-(4,4,5,5-tetramethyl-[1,3,2]dioxaboran-2-yl)-1,2,3,6-tetrahydropyridine-carboxylate and 26 mg of potassium carbonate were dissolved in 3 ml of N,N-dimethylformamide, 2.5 mg of [1,1-bis(diphenylphosphino)-ferrocene] dichloro-palladium was added thereto and the mixture was stirred for one night under heating at 80° C. After the reaction solution was cooled down to room temperature, insoluble matters were removed by filtering through Celite. Water was added to the filtrate, the mixture was extracted with diethyl ether and the diethyl ether layer washed with a saturated saline solution and dried over sodium sulfate. After the solvent was evaporated in vacuo, the residue was separated and purified by a thin-layer chromatography (hexane/ethyl acetate=2/1) to give 8.0 mg of the title compound as a white solid.

$^1$HNMR (400 MHz, CDCl$_3$) δ: 1.49 (9H, s), 2.74-2.77 (2H, m), 3.20 (3H, s), 3.65-3.68 (2H, m), 4.11-4.12 (2H, m), 4.38 (2H, s), 6.17 (1H, br), 7.24-7.34 (2H, m), 7.48-7.54 (2H, m)

ESI-MS Found: m/z 389.2 [M+H]+.

5) Production of isopropyl 4-[1-(2-fluorophenyl)-5-methoxymethyl-1H-[1,2,3]triazol-4-yl]-1,2,3,6-tetrahydropyridine-1-carboxylate tert-Butyl 4-[1-(2-fluorophenyl)-5-methoxymethyl-1H-[1,2,3]triazol-4-yl]-1,2,3,6-tetrahydropyridine-1-carboxylate (5.4 mg) prepared in the above 4) was dissolved in 2.0 ml of a 10% methanolic solution of hydrochloric acid followed by stirring at room temperature for 30 minutes. The solvent was evaporated in vacuo followed, without purification, by dissolving in 0.5 ml of pyridine and 0.02 ml of isopropyl chloroformate was added to the solution followed by stirring for 1 hour. A saturated aqueous solution of ammonium chloride was added to the reaction solution, the mixture was extracted with ethyl acetate, the extract was dried over sodium sulfate and the solvent was evaporated in vacuo. The resulting residue was separate and purified by a thin-layer chromatography (ethyl acetate/hexane=1/2) to give 4.27 mg of the title compound as a white solid.

$^1$HNMR (400 MHz, CDCl$_3$) δ: 1.28 (6H, d, J=6.0 Hz), 2.76-2.77 (2H, m), 3.20 (3H, s), 3.71 (2H, t, J=5.2 Hz), 4.16 (2H, br), 4.38 (2H, s), 4.97 (1H, quintet, J=6.0 Hz), 6.18 (1H, br), 7.27-7.34 (2H, m), 7.48-7.56 (2H, m)

ESI-MS Found: m/z 375.2 [M+H]+.

Example 15

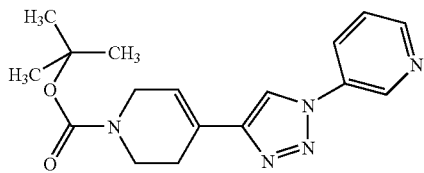

tert-Butyl 4-[1-(pyridin-3-yl)-1H-[1,2,3]triazol-4-yl]-1,2,3,6-tetrahydropyridine-1-carboxylate 3-Azidopyridine (460 mg) prepared in Example 2 and 620 mg of tert-butyl 4-ethynyl-1,2,3,6-tetrahydropyridine-1-carboxylate were dissolved in 8 ml of toluene and the solution was heated to reflux for 20 hours. The reaction solution was returned to room temperature and the solvent was evaporated in vacuo. The resulting residue was separated and produced by a silica gel chromatography (chloroform/methanol=100/1) to give 121 mg of the title compound as a white solid.

$^1$HNMR (300 MHz, CDCl$_3$) δ: 1.50 (9H, s), 2.60 (2H, bs), 3.68 (2H, t, J=5.8 Hz), 4.11-4.16 (2H, m), 6.57 (1H, bs), 7.51 (1H, dd, J=3.3, 7.9 Hz), 7.91 (1H, s), 8.13-8.18 (1H, m), 8.71 (1H, d, J=4.8 Hz), 9.00 (1H, d, J=2.6 Hz)

ESI-MS Found: m/z 328.2 [M+H]+.

Example 16

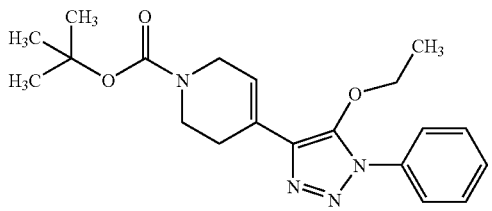

tert-Butyl 4-[5-ethoxy-1-phenyl-1H-[1,2,3]triazol-4-yl]-1,2,3,6-tetrahydropyridine-1-carboxylate

1) Production of 5-ethoxy-1-phenyl-1H-[1,2,3]-triazole

The azide substance prepared in 1) of Example 7 and (trimethylsilyl)ethoxyacetylene were dissolved in 3.0 ml of toluene and the solution was stirred for one night under heating to reflux. After the reaction solution was cooled down to room temperature, the residue was separate and purified by a silica gel column chromatography (hexane/ethyl acetate=1/1) to give 98 mg of the title compound.

2) Production of 5-ethoxy-4-iodo-1-phenyl-1H-[1,2,3]-triazole

The compound prepared in 1) was dissolved in 2 ml of tetrahydrofuran, in a nitrogen atmosphere, 0.41 ml of 1.58M n-butyl lithium was dropped into the solution at −78° C., the mixture was stirred for 10 minutes and 203 mg of iodine was added thereto. After temperature of the reaction solution was raised to room temperature, a saturated aqueous solution of sodium thiosulfate was added to the solution, the mixture was extracted with ethyl acetate and the extract was dried over sodium sulfate. After the solvent was evaporated in vacuo, the residue was separated and purified by a preparatory thin-layer silica gel column chromatography (hexane/ethyl acetate=4/1) to give 121 mg of the title compound.

3) Production of tert-butyl 4-[5-ethoxy-1-phenyl-1H-[1,2,3]triazol-4-yl]-1,2,3,6-tetrahydropyridine-1-carboxylate The same operation as Example 2 was carried out using the compound prepared in 2) and tert-butyl 4-(4,4,5,5-tetramethyl-[1,3,2]dioxaboran-2-yl)-1,2,3,6-tetrahydropyridine-1-carboxylate to give the title compound as a light yellow amorphous substance.

$^1$HNMR (300 MHz, CDCl$_3$) δ: 1.24 (3H, t, J=7.1 Hz), 1.50 (9H, s), 2.68-2.76 (2H, m), 3.61-3.68 (2H, m), 3.92 (2H, q, J=7.1 Hz), 4.07-4.13 (2H, m), 6.31 (1H, brs), 7.40-7.61 (3H, m), 7.67-7.75 (2H, m)

ESI-MS Found: m/z 371.3 [M+H]+.

Example 17

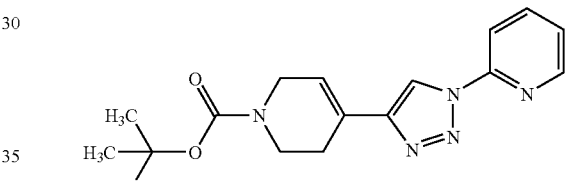

tert-Butyl 4-[1-(pyridin-2-yl)-1H-[1,2,3]triazol-4-yl]-3,6-dimethyl-2H-pyridine-1-carboxylate

1) Production of 2-azidopyridine

Sodium azide (390 mg) was dissolved in 30 ml of methanol and cooled at −78° C., 6.0 ml of a methanolic solution of 740 mg of 1-fluoropyridinium triflate was dropped thereinto and the mixture was stirred for 4 hours. The solvent was evaporated in vacuo and the residue washed with 50 ml of diethyl ether to give 296 mg of the title compound in an ark oily crude product.

2) Production of tert-butyl 4-[1-(pyridin-2-yl)-1H-[1,2,3]triazol-4-yl]-3,6-dimethyl-2H-pyridine-1-carboxylate Reaction was carried out by the same method as in Example 1-2 except that 2-azidopyridine was used in place of 1-azido-2-chlorobenzene used in Example 1-2 to give the title compound.

$^1$HNMR (400 MHz, CDCl$_3$) δ: 1.50 (9H, s), 2.58-2.62 (2H, m), 3.65-3.68 (2H, m), 4.12 (2H, br), 6.58 (1H, br), 7.33-7.35 (2H, m), 7.488-7.92 (2H, m), 8.40) 1H, s), 8.40-8.50 (2H, m)

ESI-MS Found: m/z 328.3 [M+H]+.

Example 18

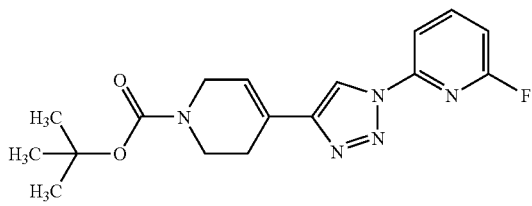

tert-Butyl 4-[1-(6-fluoropyridin-2-yl)-1H-[1,2,3]-triazol-4-yl]-1,2,3,6-tetrahydropyridine-1-carboxylate 1) Production of 2-azido-6-fluorobenzene Reaction was carried out by the same method as in Example 1-1 except that (6-fluoropyridin-2-yl)-hydrazine was used in place of 2-chlorophenylhydrazine hydrochloride used in Example 1-1 to give the title compound.

2) Production of tert-butyl 4-[1-(6-fluoropyridin-2-yl)-1H-[1,2,3]-triazol-4-yl]-1,2,3,6-tetrahydropyridine-1-carboxylate Reaction was carried out by the same method as in Example 1-2 except that 2-azido-6-fluorobenzene was used in place of 1-azido-2-chlorobenzene used in Example 1-2 to give the title compound.

$^1$HNMR (400 MHz, CDCl$_3$) δ: 1.50 (9H, s), 2.56-2.59 (2H, m), 3.67 (2H, t, J=5.5 Hz), 4.13 (2H, d, J=2.6 Hz), 6.58 (1H, br), 6.97 (1H, d, J=8.0 Hz), 8.02 (1H, dd, J=8.0, 7.6 Hz), 8.08 (1H, d, J=7.6 Hz), 8.36 (1H, s)

ESI-MS Found: m/z 346.3 [M+H]+.

Example 19

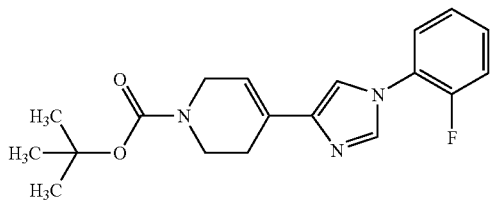

tert-Butyl 4-[1-(2-fluorophenyl)-imidazol-4-yl]-1,2,3,6-tetrahydropyridine-1-carboxylate 1) Production of 4-(1H-imidazol-4-yl)-1,2,3,6-tetra-hydropyridine hydrochloride tert-Butyl 4-hydroxy-4-(1H-imidazol-4-yl)-piperidine-1-carboxylate (20 mg) was dissolved in 6 ml of 6M hydrochloric acid and the solution was stirred at 120° C. for one night. The solvent was evaporated in vacuo and the precipitate was filtered to give 55 mg of the title compound as a dark solid crude product.

2) Production of tert-butyl 4-(1-tert-butoxycarbonyl-1H-imidazol-4-yl)-3,6-dihydro-2H-pyridine-1-carboxylate The compound prepared in the above 1), i.e. 4-(1H-imidazol-4-yl)-1,2,3,6-tetra-hydropyridine hydro-chloride (20 mg) was dissolved in 1.0 ml of tetrahydrofuran, 0.04 ml of triethylamine was added to the solution and the mixture was stirred for 2 hours after addition of 0.06 ml of di-tert-butoxy-carbonyl. Methanol was added to the reaction solution, the solvent was evaporated in vacuo and the residue was separated and purified by a thin-layer chromatography (ethyl acetate/hexane=1/2) to give 55.5 mg of the title compound as a white solid.

$^1$HNMR (400 MHz, CDCl$_3$) δ: 1.46 (9H, s), 1.61 (9H, s), 2.39 (2H, s), 3.58-3.61 (2H, m), 4.05-4.06 (2H, m), 6.43 (1H, br), 7.17 (1H, s), 7.98 (1H, s)

ESI-MS Found: m/z 350.3 [M+H]+.

3) Production of tert-butyl 4-(1H-imidazol-4-yl)-3,6-dihydro-2H-pyridine-1-carboxylate A methanolic solution of ammonium (2.0 ml) was added to 50 mg of the compound prepared in the above 2), i.e. tert-butyl 4-(1-tert-butoxycarbonyl-1H-imidazol-4-yl)-3,6-dihydro-2H-pyridine-1-carboxylate and the mixture was stirred for 5 hours. The solvent was evaporated in vacuo and the precipitate was filtered to give 32 mg of the title product as a white solid.

$^1$HNMR (400 MHz, CDCl$_3$) δ: 1.47 (9H, s), 2.44 (2H, s), 3.58-3.62 (2H, m), 4.02-4.04 (2H, m), 6.18 (1H, br), 6.95 (1H, s), 7.57 (1H, s)

ESI-MS Found: m/z 250.2 [M+H]+.

4) Production of tert-butyl 4-[1-(2-fluorophenyl)-imidazol-4-yl]-1,2,3,6-tetrahydropyridine-1-carboxylate Copper acetate (35 mg) and pyridine (0.02 ml) were added to a solution of 2 mg of the compound prepared in the above 3), i.e. tert-butyl 4-(1H-imidazol-4-yl)-3,6-dihydro-2H-pyridine-1-carboxylate and 35 mg of 2-fluorophenylboric acid in dichloromethane and the solution was stirred for three days. The solvent was evaporated in vacuo and the residue was separated and purified by a thin-layer chromatography (ethyl acetate/hexane=1/2) to give 2.48 mg of the title compound as a white solid.

$^1$HNMR (400 MHz, CDCl$_3$) δ: 1.48 (9H, s), 2.44-2.50 (2H, m), 3.60-3.66 (2H, m), 4.09 (2H, d, J=2.5 Hz), 6.42-6.44 (1H, m), 7.12 (1H, s), 7.33-7.37 (4H, m), 7.76 (1H, s),

ESI-MS Found: m/z 344.3 [M+H]+.

Example 20

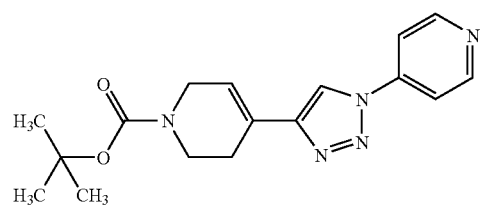

tert-Butyl 4-[1-(pyridin-4-yl)-1H-[1,2,3]triazol-4-yl]-1,2,3,6-tetrahydropyridine-1-carboxylate 1) Production of 4-azidopyridine 4-Chloropyridine (400 mg) was dissolved in 2.6 ml of a 1M aqueous solution of sodium hydroxide and 1.5 ml of ethanol, 340 mg of sodium azide was added to the solution at room temperature and the mixture was stirred at 110° C. for 4 hours. The reaction solution was returned to room temperature, diluted with chloroform and washed with water and then a saturated saline solution. The organic layer was dried over sodium sulfate and the solvent was evaporated in vacuo to give 140 mg of the crude product of the title compound.

2) Production of tert-butyl 4-[1-(pyridin-4-yl)-1H-[1,2,3]triazol-4-yl]-1,2,3,6-tetrahydropyridine-1-carboxylate 4-Azidopyridine (140 mg) prepared in the above 1) and 207 mg of tert-butyl 4-ethynyl-1,2,3,6-tetrahydropyridine-1-carboxylate were dissolved in 3 ml of toluene and the solution was heated to reflux for 20 hours. The reaction solution was returned to room temperature and the solvent was evaporated in vacuo. The resulting residue was separated and produced by a silica gel chromatography (chloroform/methanol=100/1) to give 44 mg of the title compound as a white solid.
¹HNMR (400 MHz, CDCl₃) δ: 1.49 (9H, s), 2.57 (2H, bs), 3.65-3.70 (2H, m), 4.10-4.16 (2H, m), 6.57 (1H, bs), 7.71 (2H, d, J=6.0 Hz), 7.92 (1H, s), 8.77 (2H, d, J=6.4 Hz)
ESI-MS Found: m/z 272.3 [M-t-Bu+2H]+.

Example 21

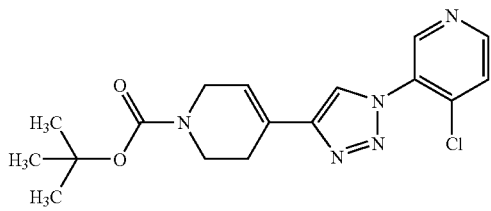

tert-Butyl 4-[1-(4-chloropyridin-3-yl)-1H-[1,2,3]-triazol-4-yl]-1,2,3,6-tetrahydropyridine-1-carboxylate 1) Production of 3-azido-4-chloropyridine In a nitrogen atmosphere, a solution of 0.7 ml of diisopropylamine in 2 ml of tetrahydrofuran was cooled at −78° C. and 3.36 ml of a 1.58M solution of n-butyl lithium in hexane was dropped thereinto. Temperature of the reaction solution was raised to 0° C. followed by stirring for 5 minutes, the solution was cooled down to −78° C. again and a solution of 0.3 g of 3-chloropyridine in 2.0 ml of tetrahydrofuran was added thereto. The solution was stirred at −78° C. for 10 minutes, a solution of 0.85 g of n-dodecylbenzenesulfoneazide in 2.0 ml of tetrahydrofuran was added followed by stirring, temperature of the reaction solution was raised to −60° C. and water was added thereto to stop the reaction. The product was extracted with ethyl acetate and dried over sodium sulfate and the solvent was evaporated in vacuo. The resulting residue was purified by a silica gel column chromatography (hexane: ethyl acetate=75:25) to give 0.69 g of the title compound as a dark reddish-brown oily crude product.

2) Production of tert-butyl 4-[1-(4-chloropyridin-3-yl)-1H-[1,2,3]-triazol-4-yl]-1,2,3,6-tetrahydropyridine-1-carboxylate Reaction was carried out by the same method as in Example 1-2 except that 3-azido-4-chloropyridine was used in place of 1-azido-2-chlorobenzene used in Example 1-2 to give the title compound.
¹HNMR (400 MHz, CDCl₃) δ: 1.48 (9H, s), 2.58 (2H, br), 3.65-3.68 (2H, m), 4.11-4.13 (2H, m), 6.54 (1H, br), 7.53-7.54 (1H, m), 7.85 (1H, s), 8.61-8.62 (1H, m), 8.82 (1H, s)
ESI-MS Found: m/z 362.3 [M+H]+.

Example 22

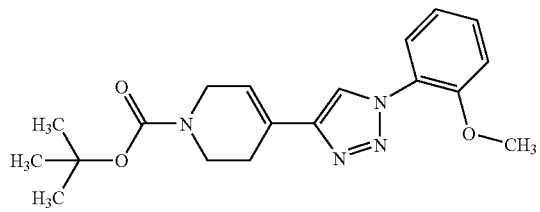

tert-Butyl 4-[1-(2-methoxyphenyl)-1H-[1,2,3]triazol-4-yl]-1,2,3,6-tetrahydropyridine-1-carboxylate 1) Production of 1-azido-2-methoxybenzene Reaction was carried out by the same method as in Example 1-1 except that (2-methoxyphenyl)-hydrazine was used in place of 2-chlorophenylhydrazine used in Example 1-1 to give the title compound as a brown oily crude product.

2) Production of tert-butyl 4-[1-(6-fluoropyridin-2-yl)-1H-[1,2,3]triazol-4-yl]-1,2,3,6-tetrahydropyridine-1-carboxylate Reaction was carried out by the same method as in Example 1-2 except that 1-azido-2-methoxybenzene was used in place of 1-azido-2-chlorobenzene used in Example 1-2 to give the title compound.
¹HNMR (400 MHz, CDCl₃) δ: 1.49 (9H, s), 2.58-2.62 (2H, m), 3.65-3.69 (2H, m), 3.88 (1H, s), 4.10-4.13 (2H, m), 6.50 (1H, br), 7.45-7.87 (2H, m), 7.40 (1H, t), 7.73 (1H, d), 7.96 (1H, s)
ESI-MS Found: m/z 357.3 [M+H]+.

Example 23

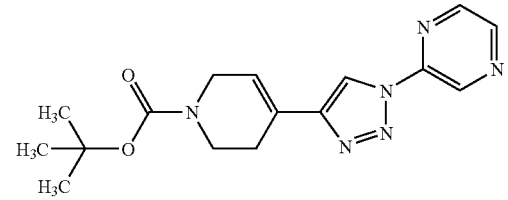

tert-Butyl 4-[1-(pyrazine-2-yl)-1H-[1,2,3]triazol-4-yl]-1,2,3,6-tetrahydropyridine-1-carboxylate

1) Production of tert-butyl 4-cyano-1,2,3,6-tetrahydropyridine-1-carboxylate Diethyl ether (15 ml) and 8 ml of water were added to 790 mg of tert-butyl 4-oxopiperidine-1-carboxylate, 216 mg of sodium cyanide and 672 mg of sodium hydrogen carbonate and the solution was stirred at room temperature for 1.5 hours. The resulting product was extracted with ether, washed with water and a saturated saline solution and dried over sodium sulfate. After the solvent was evaporated in vacuo, 10 ml of chloroform, 0.84 ml of triethylamine and 0.34 ml of methanesulfonyl chloride were added to the resulting residue followed by stirring at room temperature for 20 minutes. The reaction was stopped by water, the product was extracted with chloroform and the organic layer was washed with a saturated sodium hydrogen carbonate and a saturated saline solution and dried over sodium sulfate. The solvent was evaporated in vacuo, 10 ml of pyridine was added to the resulting residue and the mixture was stirred for one night under heating to reflux. After cooling to room temperature, the solvent was evaporated in vacuo followed by adding ethyl acetate and water. The organic layer washed with a saturated saline solution and dried over sodium sulfate and the solvent was evaporated in vacuo. The resulting residue was purified by a silica gel column chromatography (hexane/ethyl acetate=6/1) to give 650 mg of the title compound as a white solid.

$^1$HNMR (300 MHz, CDCl$_3$) δ: 1.47 (9H, s,), 2.30-2.40 (2H, m), 3.50-3.58 (2H, m), 4.01-4.10 (2H, m), 6.57 (1H, br)

2) Production of tert-butyl 4-(5-trimethylsilanyl-1H-[1,2,3-triazol-4-yl]-1,2,3,6-tetrahydropyridine-1-carboxylate A 10% solution (10 ml) of trimethylsilyl diazomethane in hexane was diluted with 20 ml of diethyl ether, cooled down to 0° C. and 3.67 ml of 1.58M n-butyl lithium was dropped thereinto. After it was stirred at 0° C. for 30 minutes, a solution of 974 mg of the compound prepared in the above 1) in 10 ml of diethyl ether was dropped thereinto. After it was stirred at room temperature for 3 hours, water was added thereto to stop the reaction. The product was extracted with ethyl acetate and dried over sodium sulfate and the solvent was evaporated in vacuo. The resulting residue was purified by a silica gel column chromatography (hexane/ethyl acetate=2/1) to give 493 mg of the title compound.

$^1$HNMR (300 MHz, CDCl$_3$) δ: 0.39 (9H, s), 1.50 (9H, s), 2.54-2.70 (2H, m), 3.59-3.71 (2H, m), 4.02-4.12 (2H, m), 5.90-6.00 (1H, m)

3) Production of tert-butyl 4-(1H-[1,2,3]triazol-4-yl)-1,2,3,6-tetrahydropyridine-1-carboxylate The compound (390 mg) prepared in the above 2) was dissolved in 10 ml of ethanol, 70 mg of potassium fluoride and 3 drops of concentrated hydrochloric acid were added thereto and the mixture was stirred at 80° C. for 2.5 hours. After the reaction solution was cooled down to room temperature, the solvent was evaporated in vacuo. To the resulting residue were added chloroform and a saturated sodium hydrogen carbonate, the organic layer was dried over sodium sulfate and the solvent was evaporated in vacuo. The resulting residue was purified by a silica gel column chromatography by a silica gel column chromatography (hexane/ethyl acetate=2/1) to give 220 mg of the title compound.

$^1$HNMR (300 MHz, CDCl$_3$) δ: 1.50 (9H, s), 2.51-2.62 (2H, m), 3.57-3.68 (2H, m), 4.02-4.12 (2H, m), 6.31 (1H, br)

4) Production of tert-butyl 4-[1-(pyrazin-2-yl)-1H-[1,2,3]triazol-4-yl]-1,2,3,6-tetrahydropyridine-1-carboxylate tert-butyl 4-(1H-[1,2,3]triazol-4-yl)-1,2,3,6-tetra-hydropyridine-1-carboxylate (10 mg) prepared in the above 3) was dissolved in 1 ml of N,N-dimethylformamide, 0.04 ml of 2-chloropyrazine, 11 mg of powdery potassium hydroxide and 10 mg of sodium hydride were added thereto and the mixture was stirred for 5 hours under heating at 120° C. The reaction solution was allowed to cool down to room temperature, water was added thereto, the mixture was extracted with ethyl acetate, the extract was dried over sodium sulfate and the solvent was evaporated in vacuo. The resulting residue was separated and purified by a thin-layer chromatography (ethyl acetate/hexane=1/2) to give 4.5 mg of the title compound as a white solid.

$^1$HNMR (400 MHz, CDCl$_3$) δ: 1.49 (9H, s), 2.57-2.58 (2H, m), 3.65-3.68 (2H, m), 4.12-4.13 (2H, br), 6.59-6.60 (1H, br), 8.38 (1H, s), 8.44-8.45 (1H, m), 8.62 (1H, d, 2.5 Hz), 8.52 (1H, d, 1.4 Hz)

ESI-MS Found: m/z 351.3 [M+H]+.

Example 24

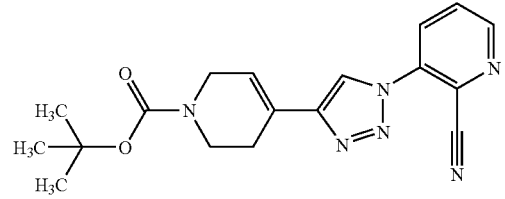

tert-Butyl 4-[1-(2-cyanopyridin-3-yl)-1H-[1,2,3]-triazol-4-yl]-1,2136-tetrahydropyridine-1-carboxylate tert-Butyl 4-[1-(2-chloropyridin-3-yl)-5-methyl-1H-[1,2,3]-triazol-4-yl]-1,2,3,6-tetrahydropyridine-1-carboxylate (143 mg) prepared in Example 12 was dissolved in 5 ml of N,N-dimethylformamide, 23 mg of sodium cyanide was added to the solution and the mixture was heated at 150° C. for 5 hours. The reaction solution was cooled down to room temperature, water was added thereto, the mixture was extracted with ethyl acetate, the extract was dried over sodium sulfate and the solvent was evaporated in vacuo. The resulting residue was separated and purified by a thin-layer chromatography (ethyl acetate/hexane=1/1) to give 7.0 mg of the title compound as a white solid.

$^1$HNMR (400 MHz, CDCl$_3$) δ: 1.50 (9H, s), 2.59-2.61 (2H, m), 3.67-3.70 (2H, m), 4.14-4.15 (2H, m), 6.59-6.60 (1H, m), 7.74-7.77 (1H, m), 8.25 (1H, s), 8.33-8.35 (1H, m), 8.80-8.81 (1H, m)

ESI-MS Found: m/z 353.3 [M+H]+.

Example 25

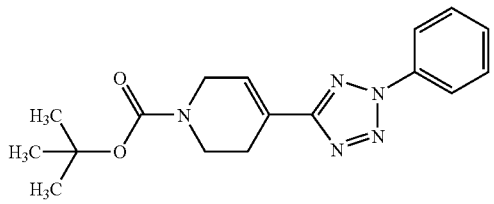

tert-Butyl 4-(2-phenyl-2H-tetrazol-5-yl)-1,2,3,6-tetrahydropyridine-1-carboxylate 1) Production of tert-butyl 4-(2H-tetrazol-5-yl)-112.326-tetrahydropyridine-1-carboxylate Dimethylformamide (2 m) was added to 104 mg of tert-butyl 4-cyano-1,2,3,6-tetrahydropyridine-1-carboxylate prepared in 1) of Example 23, 310 mg of sodium azide and 260 mg of ammonium chloride and the mixture was stirred at 115° C. for 3 hours. After cooling down to room temperature, ethyl acetate and a 2N aqueous solution of sodium hydroxide were added thereto. After the aqueous layer was neutralized with a 1N aqueous solution of hydrochloric acid, the product was extracted with chloroform. The extract was dried over sodium sulfate, the solvent was evaporated in vacuo and the resulting residue was purified by a silica gel thin-layer chromatography (chloroform/methanol=7/1) to give 12 mg of the title compound as a crude product.

2) Production of tert-butyl 4-(2-phenyl-2H-tetrazol-5-yl)-1,2,3,6-tetrahydropyridine-1-carboxylate Methylene chloride (2 ml), 60 mg of molecular sieves 4A, 12 mg of phenylboric acid, 8 μl of pyridine and 24 mg of copper(II) acetate were added to 12 mg of tert-butyl 4-(2H-tetrazol-5-yl)-1,2,3,6-tetrahydropyridine-1-carboxylate prepared in 1) and the mixture was stirred at room temperature for 3 hours. After ethyl acetate and a 2N aqueous solution of sodium hydroxide were added thereto, the organic layer washed with a saturated aqueous solution of ammonium chloride and dried over sodium sulfate and the solvent was evaporated in vacuo. The resulting residue was purified by a silica gel thin-layer chromatography (hexane/ethyl acetate=3/1) to give 1.6 mg of the title compound as a crude product.

$^1$HNMR (300 MHz, CDCl$_3$) δ: 1.50 (9H, s), 2.70-2.78 (2H, m), 3.59 (2H, t, J=5.9 Hz), 4.12-4.21 (2H, m), 6.92-7.01 (1H, m), 7.42-7.61 (3H, m), 8.06-8.15 (2H, m)

ESI-MS Found: m/z 272.2 [M-t-Bu+H]+.

Example 26

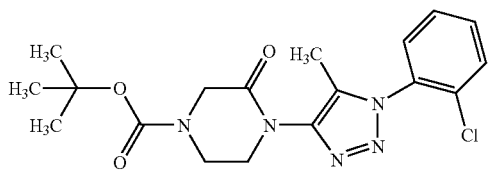

tert-Butyl 4-[1-(2-chlorophenyl)-5-methyl-1H-[1,2,3]-triazol-4-yl]-3-oxopiperazine-1-carboxylate 1) Production of 1-(2-chlorophenyl)-5-methyl-4-trimethylsilyl-1H-[1,2,3]triazole In a nitrogen atmosphere, 6.0 ml of 1-(trimethylsilyl)-1-propynyl was added to a solution of 1.5 g of 2-chlorophenyl azide in 20 ml of toluene and the mixture was stirred at 120° C. for 6 hours. The resulting solution was cooled down to room temperature, the solvent was concentrated in vacuo and the resulting residue was purified by a lica gel column chromatography (hexane: diethyl ether=90:10) to give 1.4 g of the title compound as a yellow oily substance.

2) Production of 1-(2-chlorophenyl)-5-methyl-4-iodo-1H-[1,2,3]triazole

In a nitrogen atmosphere, 1.3 g of silver tetrafluoroborate and 2.7 g of iodine were successively added to a solution of 1.4 g of the compound prepared in the above 1) in 70 ml of methanol and the mixture was stirred for one night at room temperature. After addition of an aqueous solution of sodium thiosulfate thereto, the product was extracted with chloroform and the organic layer washed with water and dried over sodium sulfate. The residue obtained by evaporation of the solvent in vacuo therefrom was purified by a silica gel chromatography (chloroform:methanol=20:1) to give 500 mg of the title compound as a colorless oily product.

3) Production of tert-butyl 4-[1-(2-chlorophenyl)-5-methyl-1H-[1,2,3]-triazol-4-yl]-3-oxopiperazine-1-carboxylate In a nitrogen atmosphere, 200 mg of tripotassium phosphate, 5 mg of copper(I) iodide and 0.1 ml of trans-1,2-diaminocyclohexane were successively added to a solution of 70 mg of the compound prepared in the above 2) and 85 mg of 4-(tert-butyloxycarbonyl)piperazin-2-one in 1 ml of dioxane followed by stirring for one night at 90° C. After water was added thereto, the product was extracted with ethyl acetate and the organic layer washed with water and dried over sodium sulfate. The solvent was evaporated in vacuo and the resulting residue was purified by a preparative thin-layer silica gel chromatography (hexane:ethyl acetate=3:1) to give 40 mg of the title compound as a white solid.

$^1$HNMR (400 MHz, CDCl$_3$) δ: 1.51 (9H, s), 2.13 (3H, s), 3.85 (4H, t, J=5.2 Hz), 4.01 (4H, t, J=5.6 Hz), 4.28 (2H, s), 7.41-7.61 (4H, m)

ESI-MS Found: m/z 392.4 [M+H]+.

Example 27

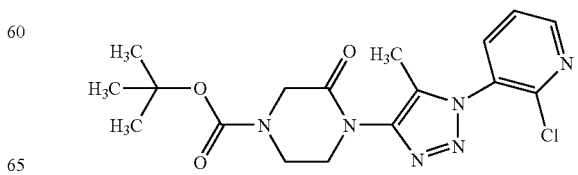

tert-Butyl 4-]1-(2-chloropyridin-3-yl)-5-methyl-1H-[1,2,3]triazol-4-yl]-3-oxopiperazine-1-carboxylate In a nitrogen atmosphere, 900 mg of tripotassium phosphate, 50 mg of copper(I) iodide and 1 ml of trans-1,2-diaminocyclohexane were successively added to a solution of 240 mg of 1-(2-chloropyridin-3-yl)-5-methyl-4-iodo-1H-[1,2,3]triazole prepared in Example 12) and 200 mg of 4-(tert-butyloxycarbonyl)piperazin-2-one in 10 ml of dioxane followed by stirring for one night at 90° C. After water was added thereto, the product was extracted with ethyl acetate and the organic layer washed with water and dried over sodium sulfate. The solvent was evaporated in vacuo and the resulting residue was purified by a silica gel chromatography (hexane:ethyl acetate=3:1) to give 180 mg of the title compound as a white solid.

$^1$HNMR (400 MHz, CDCl$_3$) δ: 1.51 (9H, s), 2.17 (3H, s), 3.86 (2H, t, J=5.2, 10.4 Hz), 4.01 (2H, t, 5.2, 10.4 Hz), 4.28 (2H, s), 7.50 (1H, q, J=4.8, 7.6 Hz), 7.87 (1H, dd, J=2.0, 8.0 Hz), 8.61 (1H, dd, J=2.0, 4.8 Hz)

ESI-MS Found: m/z 337.1 [M+H]+.

Example 28

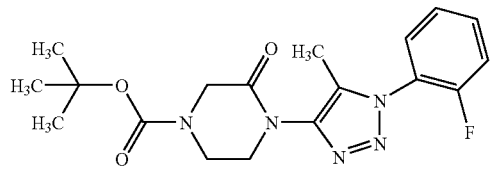

tert-Butyl 4-[1-(2-fluorophenyl)-5-methyl-1H-[1,2,3]-triazol-4-yl]-3-oxopiperazine-1-carboxylate

1) Production of 1-(2-fluorophenyl)-5-methyl-4-trimethylsilyl-1H-[1,2,3]triazole In a nitrogen atmosphere, 6.0 ml of 1-(trimethylsilyl-1-propynyl was added to a solution of 1.5 g of 2-fluorophenyl azide in 20 ml of toluene and the mixture was stirred at 120° C. for 6 hours. After the resulting solution was cooled down to room temperature, the solvent was concentrated in vacuo and the resulting residue was purified by a lica gel column chromatography (hexane: diethyl ether=90:10) to give 1.4 g of the title compound as a yellow oily product.

2) Production of 1-(2-fluorophenyl)-5-methyl-4-iodo-1H-[1,2,3]triazole

In a nitrogen atmosphere, 1.3 g of silver tetrafluoroborate and 2.7 g of iodine were added successively, under cooling with ice, to a solution of 1.4 g of the compound prepared in the above 1) in 70 ml of methanol and the mixture was stirred for one night at room temperature. After an aqueous solution of sodium thiosulfate was added, the product was extracted with chloroform and the organic layer washed with water and dried over sodium sulfate. The residue prepared by evaporation of the solvent in vacuo was purified by a silica gel column chromatography (chloroform:methanol=20:1) to give 500 mg of the title compound as a light yellow solid.

$^1$HNMR (300 MHz, CDCl$_3$) δ: 2.27 (3H, s), 7.27-7.37 (2H, m), 7.50-7.55 (2H, m)

ESI-MS Found: m/z 304.1 [M+H]+.

3) Production of tert-butyl 4-[1-(2-fluorophenyl)-5-methyl-1H-[1,2,3]-triazol-4-yl]-3-oxopiperazine-1-carboxylate Tripotassium phosphate (1100 mg), 50 mg of copper(I) iodide and 1.0 ml of trans-1,2-diaminocyclohexane were successively added to a solution of 360 mg of the compound prepared in the above 2) and 420 mg of 4-(tert-butyloxycarbonyl)piperazin-2-one in 10 ml of dioxane and the mixture was stirred for one night at 90° C. After addition of water, the product was extracted with ethyl acetate and the organic layer washed with water and dried over sodium sulfate. The residue after evaporation of the solvent in vacuo was purified by a preparative thin-layer silica gel chromatography (hexane:ethyl acetate=3:1) to give 90 mg of the title compound as a white solid.

$^1$HNMR (400 MHz, CDCl$_3$) δ: 1.51 (9H, s), 2.18 (3H, d, J=1.2 Hz), 3.85 (2H, t, J=5.4, 10.8 Hz), 3.98 (2H, t, 5.4, 10.8 Hz), 4.28 (2H, s), 7.29-7.36 (2H, m), 7.51-7.56 (2H, m)

ESI-MS Found: m/z 376.2 [M+H]+.

Example 29

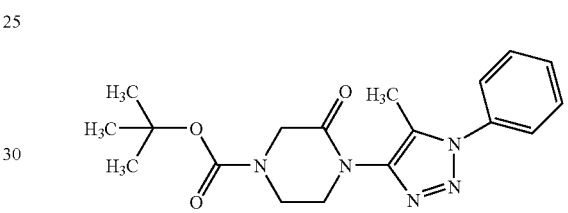

tert-Butyl 4-5-methyl-1-phenyl-1H-[1,2,3]triazol-4-yl)-3-oxopiperazine-1-carboxylate

1) Production of 1-phenyl-5-methyl-4-trimethylsilyl-1H-[1,2,3]triazole

In a nitrogen atmosphere, 6.0 ml of 1-(trimethylsilyl)-1-propynyl was added to a solution of 1.5 g of phenyl azide in 20 ml of toluene and the mixture was stirred at 120° C. for 6 hours. After the resulting solution was cooled down to room temperature, the solvent was concentrated in vacuo and the resulting residue was purified by a lica gel column chromatography (hexane: diethyl ether=90:10) to give 1.4 g of the tile compound as a yellow oily product.

2) Production of 1-phenyl-5-methyl-4-iodo-1H-[1,2,3]-triazole

In a nitrogen atmosphere, 1.3 g of silver tetrafluoroborate and 2.7 g of iodine were successively added, under cooling with ice, to a solution of 1.4 g of the compound prepared in the above 1) in 70 ml of methanol and the mixture was stirred for one night at room temperature. After addition of an aqueous solution of sodium thiosulfate, the product was extracted with chloroform and the organic layer washed with water and dried over sodium sulfate. The residue prepared by evaporation of the solvent was purified by a silica gel chromatography (chloroform:methanol=20:1) to give 500 mg of the title compound as a light yellow solid.

$^1$HNMR (300 MHz, CDCl$_3$) δ: 2.26 (3H, s), 7.45-7.55 (5H, m)

ESI-MS Found: m/z 286.1 [M+H]+.

3) Production of tert-butyl 4-(5-methyl-1-phenyl-1H-[1,2,3]triazol-4-yl)-3-oxopiperazine-1-carboxylate In a nitrogen atmosphere, 1100 mg of tripotassium phosphate, 50 mg of copper(I) iodide and 1.0 ml of trans-1,2-diaminocyclohexane were successively added to a solution of 300 mg of the compound prepared in the above 2) and 420 mg of 4-(tert-butyloxycarbonyl)piperazin-2-one in 10 ml of dioxane and the mixture was stirred for one night at 90° C. After addition of water, the product was extracted with ethyl acetate and the organic layer washed with water and dried over sodium sulfate. The residue after evaporation of the solvent in vacuo was purified by a preparative thin-layer silica gel chromatography (hexane:ethyl acetate=3:1) to give 170 mg of the title compound as a white solid.

$^1$HNMR (400 MHz, CDCl$_3$) δ: 1.51 (9H, s), 2.35 (3H, s), 3.84 (2H, t, J=6.0, 12.0 Hz), 3.97 (2H, t, J=5.6, 11.2 Hz), 4.28 (2H, s), 7.46-7.54 (5H, m)

ESI-MS Found: m/z 358.3 [M+H]+.

Example 30

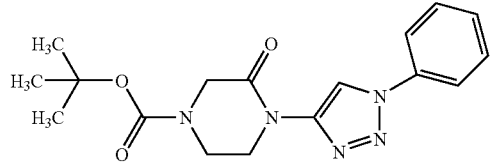

tert-Butyl 4-(1-phenyl-1H-[1,2,3]triazol-4-yl)-3-oxo-piperazine-1-carboxylate

1) Production of 1-phenyl-4-trimethylsilyl-1H-[1,2,3]-triazole

In a nitrogen atmosphere, 2.0 ml of 1-(trimethylsilyl)-ethynyl was added to a solution of 1.0 g of phenyl azide in 20 ml of toluene and the mixture was stirred at 120° C. for 6 hours. After the resulting solution was cooled down to room temperature, the solvent was concentrated in vacuo and the resulting residue was purified by a lica gel column chromatography (hexane:diethyl ether=90:10) to give 0.8 g of the title compound as a yellow oily product.

2) Production of 1-phenyl-4-iodo-1H-[1,2,3]-triazole

In a nitrogen atmosphere, 0.9 g of silver tetrafluoroborate and 1.8 g of iodine were successively added, under cooling with ice, to a solution of 0.8 g of the compound prepared in the above 1) in 40 ml of methanol and the mixture was stirred for one night at room temperature. After addition of an aqueous solution of sodium thiosulfate, the product was extracted with chloroform and the organic layer washed with water and dried over sodium sulfate. The residue prepared by evaporation of the solvent in vacuo was purified by a silica gel chromatography (chloroform:methanol=20:1) to give 500 mg of the title compound as a light yellow solid.

ESI-MS Found: m/z 272.1 [M+H]+.

3) Production of tert-butyl 4-[1-phenyl-1H-[1,2,3]triazol-4-yl]-3-oxopiperazine-1-carboxylate In a nitrogen atmosphere, 100 mg of tripotassium phosphate, 5 mg of copper(I) iodide and 0.1 ml of trans-1,2-diaminocyclohexane were successively added to a solution of 70 mg of the compound prepared in the above 2) and 200 mg of 4-(tert-butyloxycarbonyl)piperazin-2-one in 1 ml of dioxane and the mixture was stirred for one night at 90° C. After addition of water, the product was extracted with ethyl acetate and the organic layer washed with water and dried over sodium sulfate. The residue after evaporation of the solvent in vacuo was purified by a preparative thin-layer silica gel chromatography (hexane:ethyl acetate=3:1) to give 20 mg of the title compound as a white solid.

$^1$HNMR (400 MHz, CDCl$_3$) δ: 1.50 (9H, s), 3.83 (2H, t, J=6.0 Hz), 3.97 (2H, t, J=5.6 Hz), 4.28 (2H, s), 7.46-7.88 (6H, m)

ESI-MS Found: m/z 344.2 [M+H]+.

Example 31

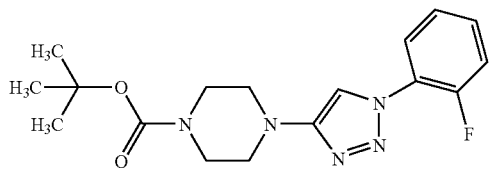

tert-Butyl 4-[1-(2-fluorophenyl)-1H-[1,2,3]triazol-4-4-yl)-piperazine-1-carboxylate 1) Production of 1-(2-fluorophenyl)-4-trimethylsilyl-1H-[1,2,3]-triazole In a nitrogen atmosphere, 6.0 ml of 1-(trimethylsilyl)-ethynyl was added to a solution of 1.5 g of 2-fluorophenyl azide in 20 ml of toluene and the mixture was stirred at 120° C. for 6 hours. After the resulting solution was cooled down to room temperature, the solvent was concentrated in vacuo and the resulting residue was purified by a lica gel column chromatography (hexane:diethyl ether=90:10) to give 1.4 g of the title compound as a yellow oily product.

2) Production of 1-(2-fluorophenyl)-4-iodo-1H-[1,2,3]-triazole

In a nitrogen atmosphere, 1.3 g of silver tetrafluoroborate and 2.7 g of iodine were successively added, under cooling with ice, to a solution of 1.4 g of the compound prepared in the above 1) in 70 ml of methanol and the mixture was stirred for one night at room temperature. After addition of an aqueous solution of sodium thiosulfate, the product was extracted with chloroform and the organic layer washed with water and dried over sodium sulfate. The residue prepared by evaporation of the solvent in vacuo was purified by a silica gel chromatography (chloroform:methanol=20:1) to give 700 mg of the title compound as a colorless oily product.

ESI-MS Found: m/z 304.1 [M+H]+.

3) Production of tert-butyl 4-[1-(2-fluorophenyl-1H-[1,2,3]triazol-4-4-yl)-piperazine-1-carboxylate In a nitrogen atmosphere, 300 mg of tripotassium phosphate, 10 mg of copper(I) iodide and 0.1 ml of trans-1,2-diaminocyclohexane were successively added to a solution of 90 mg of the compound prepared in the above 2) and 150 mg of 4-(tert-butyloxycarbonyl)piperazin-2-one in 2 ml of dioxane and the mixture was stirred for one night at 90° C. After addition of water, the product was extracted with ethyl acetate and the organic layer washed with water and dried over sodium sulfate. A borane methyl sulfide complex (0.1 ml) was added to the residue after evaporation of the solvent in vacuo and the mixture was stirred at room temperature for 1 hour. After addition of pyridine, the residue prepared by evaporation in vacuo was purified by a preparative thin-layer silica gel chromatography (hexane:ethyl acetate=3:1) to give 15 mg of the title compound as a white solid.

$^1$HNMR (400 MHz, CDCl$_3$) δ: 1.49 (9H, s), 3.24 (4H, t, J=5.2 Hz), 3.61 (4H, t, J=5.2 Hz), 7.21-7.43 (4H, m), 7.88-7.95 (1H, m)

ESI-MS Found: m/z 348.4 [M+H]+.

Example 32

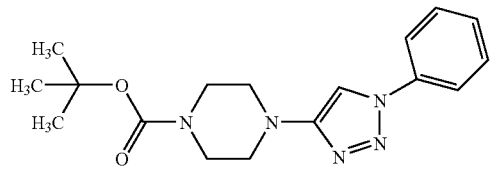

tert-Butyl 4-(1-phenyl-1H-[1,2,3]triazol-4-yl)-piperazine-1-carboxylate

In a nitrogen atmosphere, 200 mg of tripotassium phosphate, 5 mg of copper(I) iodide and 0.1 ml of trans-1,2-diaminocyclohexane were successively added to a solution of 50 mg of 1-phenyl-4-iodo-1H-[1,2,3]triazole and 80 mg of 4-(tert-butyloxycarbonyl)piperazin-2-one in 2 ml of dioxane and the mixture was stirred for one night at 90° C. After addition of water, the product was extracted with ethyl acetate and the organic layer washed with water and dried over sodium sulfate. A borane methyl sulfide complex (0.1 ml) was added to the residue after evaporation of the solvent in vacuo and the mixture was stirred at room temperature for 1 hour. After addition of pyridine, the residue prepared by evaporation in vacuo was purified by a preparative thin-layer silica gel chromatography (hexane:ethyl acetate=3:1) to give 10 mg of the title compound as a white solid.

$^1$HNMR (400 MHz, CDCl$_3$) δ: 1.49 (9H, s), 3.24 (4H, brs), 3.60 (4H, t, J=5.4 Hz), 7.27 (1H, s), 7.35-7.53 (3H, m), 7.68 (2H, d, J=8.0 Hz)

ESI-MS Found: m/z 330.4 [M+H]+.

Example 33

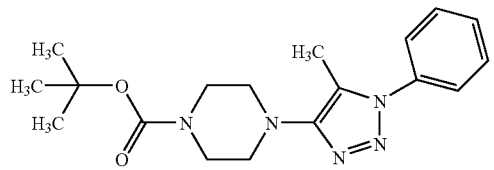

tert-Butyl 4-(1-phenyl-5-methyl-1H-[1,2,3]triazol-4-yl)-piperazine-1-carboxylate In a nitrogen atmosphere, 2 g of tripotassium phosphate, 50 mg of copper(I) iodide and 1 ml of trans-1,2-diaminocyclohexane were successively added to a solution of 500 mg of 1-phenyl-5-methyl-4-iodo-1H-[1,2,3]triazole and 700 mg of 4-(tert-butyloxycarbonyl)piperazin-2-one in 10 ml of dioxane and the mixture was stirred for one night at 90° C. After addition of water, the product was extracted with ethyl acetate and the organic layer washed with water and dried over sodium sulfate. A borane methyl sulfide complex (0.1 ml) was added to the residue after evaporation of the solvent in vacuo and the mixture was stirred at room temperature for 1 hour. After addition of pyridine, the residue prepared by evaporation in vacuo was purified by a silica gel chromatography (hexane:ethyl acetate=3:1) to give 90 mg of the title compound as a white solid.

$^1$HNMR (400 MHz, CDCl$_3$) δ: 1.49 (9H, s), 2.26 (3H, s), 3.12-3.20 (4H, m), 3.59 (4H, t, J=5.0 Hz), 7.40-7.60 (5H, m)

ESI-MS Found: m/z 344.3 [M+H]+.

Example 34

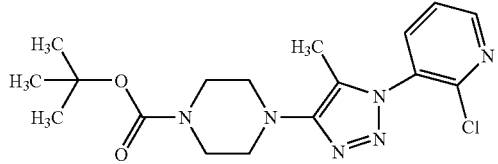

tert-Butyl 4-[1-(2-chloropyridin-3-yl)-5-methyl-1H-[1,2,3]triazol-4-yl)-piperazine-1-carboxylate In a nitrogen atmosphere, 200 mg of tripotassium phosphate, 5 mg of copper(I) iodide and 0.1 ml of trans-1,2-diaminocyclohexane were successively added to a solution of 60 mg of 1-(2-chloropyridin-3-yl)-5-methyl-4-iodo-1H-[1,2,3]triazole and 50 mg of 4-(tert-butyloxycarbonyl)piperazin-2-one in 2 ml of dioxane and the mixture was stirred for one night at 90° C. After addition of water, the product was extracted with ethyl acetate and the organic layer washed with water and dried over sodium sulfate. A borane methyl sulfide complex (0.1 ml) was added to the residue after evaporation of the solvent in vacuo and the mixture was stirred at room temperature for 1 hour. After addition of pyridine, the residue prepared by evaporation in vacuo was purified by a preparative thin-layer silica gel chromatography (hexane:ethyl acetate=3:1) to give 7 mg of the title compound as a white solid.

$^1$HNMR (400 MHz, CDCl$_3$) δ: 1.49 (9H, s), 2.17 (3H, s), 3.14-3.21 (4H, m), 3.55-3.63 (4H, m), 7.45-7.55 (1H, m), 7.75-7.85 (1H, m), 8.55-8.60 (1H, m)

ESI-MS Found: m/z 379.4 [M+H]+.

Example 35

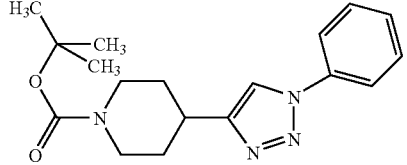

tert-Butyl 4-(1-phenyl-1H-[1,2,3]triazol-4-yl)-piperidine-1-carboxylate tert-Butyl 4-[1-phenyl-1H-[1,2,3]triazol-4-yl]-1,2,3,6-tetrahydropyridine-1-carboxylate (5 mg) was dissolved in 1 ml of ethanol, a catalytic amount of 20% palladium hydroxide was added and the mixture was vigorously stirred for 30 minutes in a hydrogen atmosphere. The reaction solution was filtered through Celite. The solvent was evaporated from the resulting filtrate to give 5 mg of the title compound as a white solid.

$^1$HNMR (300 MHz, CDCl$_3$) δ: 1.48 (9H, s), 1.62-1.76 (2H, m), 2.09 (2H, bd, J=11.3 Hz), 2.84-3.09 (3H, m), 4.13-4.28 (2H, m), 7.43 (1H, t, J=6.3 Hz), 7.52 (2H, t, J=8.5 Hz), 7.68-7.74 (3H, m)

ESI-MS Found: m/z 273.3 [M-t-Bu+2H]+.

Example 36

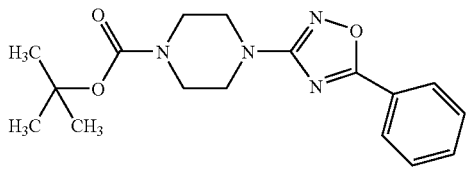

tert-Butyl 4-(5-phenyl-[1,2,4]oxadiazol-3-yl)-piperazine-1-carboxylate

1) Production of tert-butyl 4-(N-hydroxyamidino)-piperazine-1-carboxylate

In a nitrogen atmosphere, a suspension of 7.52 g of tert-butyl 4-cyanopiperazine-1-carboxylate (JMC, 1988, 31, 1036), 7.46 g of hydroxyammonium chloride and 19.7 g of potassium carbonate in 40 ml of ethanol was heated to reflux for 2 hours. The residue prepared by evaporation of the solvent was diluted with ethyl acetate, washed with water and then with a saturated saline solution and dried over sodium sulfate. The solvent was evaporated in vacuo to give 7.51 g of the title compound as a white solid.

ESI-MS Found: m/z 245.2 [M+H]+.

2) Production of tert-butyl 4-(5-phenyl-[1,2,4]oxadiazol-3-yl)-piperazine-1-carboxylate tert-Butyl 4-(N-hydroxyamidino)-piperazine-1-carboxylate (200 mg) prepared in the above 1) was dissolved in 10 ml of toluene, 2.0 g of benzoic acid anhydride was added thereto and the mixture was stirred at 100° C. for 4 hours. The reaction solution was diluted with ethyl acetate, washed with aqueous ammonia and then with a saturated saline solution and dried over sodium sulfate. The residue prepared by evaporation of the solvent was purified by a preparative thin-layer silica gel chromatography (hexane:ethyl acetate=1:1) to give 13.7 mg of the title compound as a white solid.

$^1$HNMR (300 MHz, CDCl$_3$) δ: 1.49 (9H, s), 3.53-3.55 (8H, m), 7.47-7.57 (3H, m), 8.07 (2H, d, J=7.1 Hz)

ESI-MS Found: m/z 231.2 [M-Boc].

Example 37

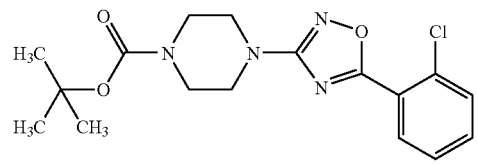

tert-Butyl 4-[5-(2-chlorophenyl)-[1,2,4]oxadiazol-3-yl]-piperazine-1-carboxylate tert-Butyl 4-(N-hydroxyamidino)-piperazine-1-carboxylate (290 mg) prepared in Example 36 was dissolved in 2 ml of pyridine, 0.20 ml of 2-chlorobenzoyl chloride was added thereto and the mixture was heated to reflux for 1 hour. The reaction solution was diluted with diethyl ether, washed with 1N hydrochloric acid, a saturated aqueous solution of sodium hydrogen carbonate and a saturated saline solution and dried over anhydrous magnesium sulfate. The residue prepared by evaporation of the solvent was purified by a preparative thin-layer silica gel chromatography (hexane:ethyl acetate=7:3) to give 64.0 mg of the title compound as a white solid.

$^1$HNMR (300 MHz, CDCl$_3$) δ: 1.49 (9H, s), 3.53-3.55 (8H, m), 7.36-7.56 (3H, m), 8.00 (1H, dd, J=1.4 and 7.8 Hz)

ESI-MS Found: m/z 265.1 [M-Boc].

Example 38

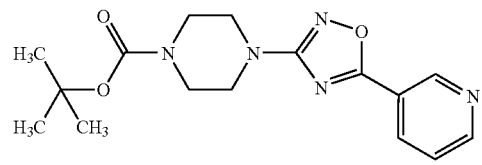

tert-Butyl 4-(5-pyridin-3-yl-[1,2,4]oxadiazol-3-yl)-piperazine-1-carboxylate tert-Butyl 4-(N-hydroxyamidino)-piperazine-1-carboxylate (320 mg) prepared in Example 36 was dissolved in 3 ml of tetrahydrofuran, 36 mg of sodium hydride was added thereto, the mixture was stirred at 60° C. for 15 minutes, a solution of 360 mg of methyl nicotinate in 2 ml of tetrahydrofuran was added thereto and the mixture was heated to reflux for 1 hour. The reaction solution was diluted with ethyl acetate, washed with water and a saturated saline solution and dried over sodium sulfate. The residue prepared by evaporation of the solvent was purified by a preparative thin-layer silica gel chromatography (hexane:ethyl acetate=1:1) to give 39.7 mg of the title compound as a white solid.

$^1$HNMR (300 MHz, CDCl$_3$) δ: 1.49 (9H, s), 3.53-3.58 (8H, m), 7.43-7.48 (1H, m), 8.31-8.35 (1H, m), 8.79-8.81 (1H, m), 9.30 (1H, d, J=1.4 Hz)

ESI-MS Found: m/z 332.3 [M+H].

Example 39

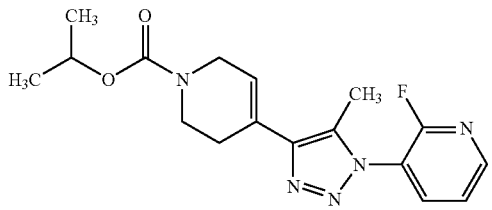

Isopropyl 4-[1-(2-fluoropyridin-3-yl)-5-methyl-1H-[1,2,3]triazol-4-yl]-1,2,3,6-tetrahydropyridine-1-carboxylate 1) Production of isopropyl 4-(1-propynyl)-1,2,3,6-tetrahydropyridine-1-carboxylate tert-Butyl 4-(1-propynyl)-1,2,3,6-tetrahydropyridine-1-carboxylate (410 mg) prepared in 3) of Example 7 was dissolved in 10% methanolic hydrochloric acid followed by stirring at room temperature for 3 hours and the solvent was evaporated in vacuo. The resulting residue was dissolved in 10 ml of methylene chloride and cooled down to 0° C. and 0.56 ml of triethylamine and 354 mg of isopropyl chloroformate were dropped thereinto. After raising its temperature to room temperature, the reaction was stopped by a saturated aqueous solution of sodium hydrogen carbonate. The product was extracted with ethyl acetate and the organic layer washed with a saturated aqueous solution of ammonium chloride and dried over sodium sulfate. After the solvent was evaporated, the residue was separate and purified by a silica gel column chromatography (hexane/ethyl acetate=4/1) to give 384 mg of a crude product of the title compound.

2) Production of isopropyl 4-[1-(2-fluoro-pyridin-3-yl)-5-methyl-1H-[1,2,3]triazol-4-yl-1,2,3,6-tetrahydropyridine-1-carboxylate The same operation as in Example 7 was carried out using isopropyl 4-(1-propynyl)-1,2,3,6-tetrahydropyridine-1-carboxylate prepared in 1) and the azide substance prepared in Example 4 to give the title compound as a light yellow solid.

$^1$HNMR (300 MHz, CDCl$_3$) δ: 1.28 (6H, d, J=6.3 Hz), 2.34 (3H, d, J=2.0 Hz), 2.70-2.80 (2H, m), 3.67-3.78 (2H, m), 4.10-4.20 (2H, m), 4.98 (1H, sept, J=6.3 Hz), 6.01-6.09 (1H, m), 7.41-7.49 (1H, m), 7.95-8.03 (1H, m), 8.38-8.47 (1H, m)

ESI-MS Found: m/z 346.3 [M+H]+.

Example 40

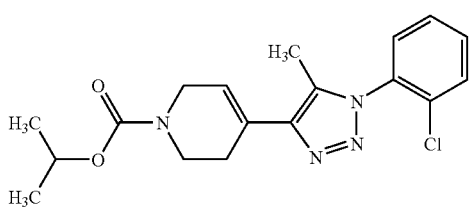

Isopropyl 4-[1-(2-chlorophenyl)-5-methyl-1H-[1,2,3]-triazol-4-yl]-1,2,3,6-tetrahydropyridine-1-carboxylate 1) Production of 4-[1-(2-chlorophenyl)-5-methyl-1H-[1,2,3]triazol-4-yl]-1,2,3,6-tetrahydropyridine hydrochloride tert-Butyl 4-[1-(2-chlorophenyl)-5-methyl-1H-[1,2,3]-triazol-4-yl]-1,2,3,6-tetrahydropyridine-1-carboxylate (40 mg) prepared in Example 10 was dissolved in 10% methanolic hydrochloric acid and stirred at room temperature for 3.5 hours and the solvent was evaporated in vacuo to give the title compound as a mixture.

2) Production of isopropyl 4-[1-(2-chlorophenyl)-5-methyl-1H-[1,2,3]-triazol-4-yl]-1,2,3,6-tetrahydropyridine-1-carboxylate Methylene chloride (2 ml), 0.2 ml of triethylamine and 0.1 ml of isopropyl chloroformate were added to the amine substance prepared in 1) and the mixture was stirred at room temperature for 15 minutes. Reaction was stopped by a saturated aqueous solution of sodium hydrogen carbonate, the product was extracted with ethyl acetate and the organic layer washed with a saturated aqueous solution of ammonium chloride and dried over sodium sulfate. After the solvent was evaporated in vacuo and the residue was separated and purified by a silica gel thin-layer chromatography (hexane/ethyl acetate=1/1) to give 18.5 mg of the title compound as a light yellow oily product.

$^1$HNMR (300 MHz, CDCl$_3$) δ: 1.28 (6H, d, J=6.1 Hz), 2.25 (3H, s), 2.72-2.83 (2H, m), 3.65-3.78 (2H, m), 4.10-4.22 (2H, m), 4.98 (1H, sept, J=6.1 Hz), 6.01-6.11 (1H, m), 7.40-7.65 (4H, m)

ESI-MS Found: m/z 361.1 [M+H]+.

Example 41

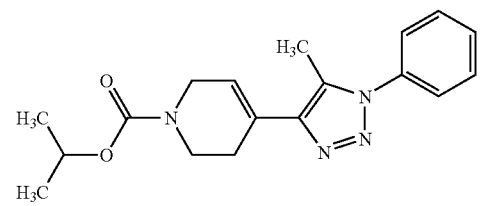

Isopropyl 4-[1-phenyl-5-methyl-1H-[1,2,3]triazol-4-yl-1,2,3,6-tetrahydropyridine-1-carboxylate 1) Production of 4-(5-methyl-1-phenyl-1H-[1,2,3]-triazol-4-yl]-1,2,3,6-tetrahydropyridine hydrochloride tert-Butyl 4-[1-phenyl-5-methyl-1H-[1,2,3]-triazol-4-yl]-1,2,3,6-tetrahydropyridine-1-carboxylate (7.4 mg) prepared in Example 7 was dissolved in 2.0 ml of 10% methanolic hydrochloric acid solution and stirred at room temperature for 10 minutes. The solvent was evaporated in vacuo to give the title compound as a brown solid crude product.

2) Production of isopropyl 4-[1-phenyl-5-methyl-1H-[1,2,3]-triazol-4-yl]-1,2,3,6-tetrahydropyridine-1-carboxylate Pyridine (0.5 ml) and 0.01 ml of isopropyl chloroformate were added to 4-(5-methyl-1-phenyl-1H-[1,2,3]-triazol-4-yl]-1,2,3,6-tetrahydropyridine hydrochloride prepared in the above 1) and the mixture was stirred for one night. A saturated aqueous solution of ammonium chloride was added to the reaction solution, the mixture was extracted with ethyl acetate, the organic layer was dried over sodium sulfate and the solvent was evaporated in vacuo. The resulting residue was separated and purified by a thin-layer chromatography (ethyl acetate/hexane=1/2) to give 3.5 mg of the title compound as a white solid.

$^1$HNMR (400 MHz, CDCl$_3$) δ: 1.28 (6H, d, J=6.4 Hz), 2.37 (3H, s), 2.73-2.76 (2H, m), 3.70 (2H, t, J=6.0 Hz), 4.14 (2H, m), 4.96 (1H, quintet, J=6.4 Hz), 5.99 (1H, br), 7.42-7.44 (2H, m), 7.50-7.55 (3H, m)

ESI-MS Found: m/z 327.3 [M+H]+.

Example 42

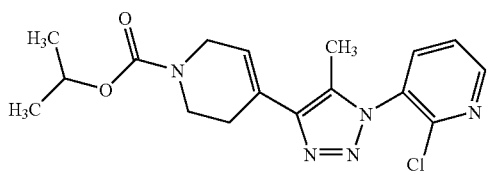

Isopropyl 4-[1-(2-chloropyridin-3-yl)-5-methyl-1H-[1,2,3]-triazol-4-yl]-1,2,3,6-tetrahydropyridine-1-carboxylate 1) Production of 4-[1,2-chloropyridin-3-yl)-5-methyl-1H-[1,2,3]triazol-4-yl]-1,2,3,6-tetrahydropyridine hydrochloride tert-Butyl 4-[1-(2-chloropyridin-3-yl)-5-methyl-1H-[1,2,3]-triazol-4-yl]-1,2,3,6-tetrahydropyridine-1-carboxylate (265 mg) prepared in Example 12 was dissolved in 4.0 ml of a 10% methanolic hydrochloric acid and stirred for 2.5 hours and the solvent was evaporated in vacuo to give the title compound as a mixture.

2) Production of isopropyl 4-[1-(2-chloropyridin-3-yl)-5-methyl-1H-[1,2,3]-triazol-4-yl]-1,2,3,6-tetrahydropyridine-1-carboxylate Methylene chloride (3 ml), 0.28 ml of triethylamine and 98 mg of isopropyl chloroformate were added to the amine substance prepared in 1) and the mixture was stirred at room temperature for 1 hour. Reaction was stopped by a saturated aqueous solution of sodium hydrogen carbonate, the product was extracted with ethyl acetate and the organic layer washed with a saturated aqueous solution of ammonium chloride and dried over sodium sulfate. After the solvent was evaporated in vacuo and the residue was separated and purified by a silica gel column chromatography (hexane/ethyl acetate=1/1) to give 110 mg of the title compound as a white solid.

$^1$HNMR (300 MHz, CDCl$_3$) δ: 1.28 (6H, d, J=6.3 Hz), 2.30 (3H, s), 2.71-2.82 (2H, m), 3.67-3.78 (2H, m), 4.11-4.21 (2H, m), 4.98 (1H, sept, J=6.3 Hz), 6.02-6.11 (1H, br), 7.46-7.52 (1H, m), 7.78-7.86 (1H, m), 8.59-8.65 (1H, m)

ESI-MS Found: m/z 362.1 [M+H]+.

Example 43

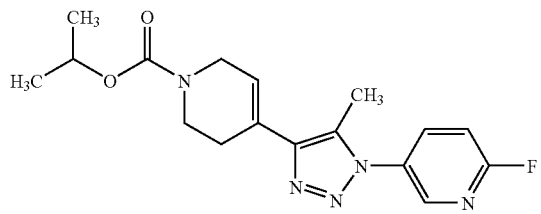

Isopropyl 4-[1-(2-fluoropyridin-5-yl)-5-methyl-1H-[1,2,3]triazol-4-yl]-1,2,3,6-tetrahydropyridine-1-carboxylate 1) Production of 5-azido-2-fluoropyridine In a nitrogen atmosphere, a solution of 3.5 g of 5-bromo-2-fluoropyridine in 40 ml of diethyl ether was cooled at −78° C. and 8.3 ml of 2.6M n-butyl lithium was dropped into this solution. After the reaction solution was stirred at −78° C. for 10 minutes, a solution of 5.1 g of 2,4,6-triisopropylbenzene sulfoneazide in 20 ml of diethyl ether was added thereto, the mixture was stirred and raised to −65° C. temperature and the reaction was stopped by addition of water. The product was extracted with diethyl ether and dried over sodium sulfate and the solvent was evaporated in vacuo. The resulting residue was purified by a silica gel column chromatography (hexane: ethyl acetate=75:25) to give 1.80 g of the title compound as a dark reddish-brown oily crude product.

2) Production of isopropyl 4-[1-(2-fluoropyridin-5-yl)-5-methyl-1H-[12.3]triazol-4-yl]-1,2,3,6-tetrahydropyridine-1-carboxylate The same operation as in Example 7 was carried out using the azide substance prepared in 1) and isopropyl 4-1-propynyl)-1,2,3,6-tetrahydropyridine-1 carboxylate prepare in Example 39 to give the title compound as a white solid.

$^1$HNMR (300 MHz, CDCl$_3$) δ: 1.28 (6H, d, J=6.2 Hz), 2.41 (3H, s), 2.68-2.80 (2H, m), 3.64-3.78 (2H, m), 4.10-4.20 (2H, m), 4.99 (1H, quin, J=6.2 Hz), 6.00-6.08 (1H, m), 7.10-7.20 (1H, m), 7.90-8.00 (1H, m), 8.32-8.40 (1H, m)

ESI-MS Found: m/z 346.2 [M+H]+.

Example 44

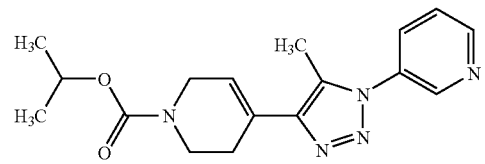

Isopropyl 4-[1-(pyridine-3-yl)-1H-[1,2,3]triazol-4-yl]-1,2,3,6-tetrahydropyridine-1-carboxylate 1) Production of 4-[1-(pyridin-3-yl)-1H-[1,2,3]-triazol-4-yl]-1,2,3,6-tetrahydropyridine A 4N solution of hydrochloric acid in dioxane (3 ml) was added to 15 mg of tert-butyl 4-[5-methyl-1-(pyridine-3-yl)-1H-[1,2,3]triazol-4-yl]-1,2,3,6-tetrahydropyridine-1-carboxylate, the mixture was stirred at room temperature for 3 hours and the solvent was evaporated in vacuo to give 6 mg of the title compound as a white solid.

2) Isopropyl 4-[1-(pyridine-3-yl)-1H-[1,2,3]triazol-4-yl]-1,2,3,6-tetrahydropyridine-1-carboxylate In a nitrogen atmosphere, 3 mg of the compound prepared in the above 1) was dissolved in 1 ml of chloroform, 0.03 ml of isopropyl chloroformate and 0.06 ml of triethylamine were added thereto and the mixture was stirred at room temperature for one night. After the solvent was evaporated in vacuo, the resulting residue was purified by a preparatory thin layer silica gel chromatography (chloroform:methanol=9:1) to give 1 mg of the title compound as a white solid.

$^1$HNMR (400 MHz, CDCl$_3$) δ: 1.28 (6H, d, J=5.6 Hz), 2.41 (3H, s), 2.72-2.80 (2H, m), 3.71 (2H, t, J=5.6 Hz), 4.16 (2H, brs), 4.93-5.02 (1H, m), 6.02 (1H, brs), 7.47-7.55 (1H, m), 7.81-7.88 (1H, m), 8.73-8.78 (2H, m)

ESI-MS Found: m/z 328.2 [M+H]+.

Example 45

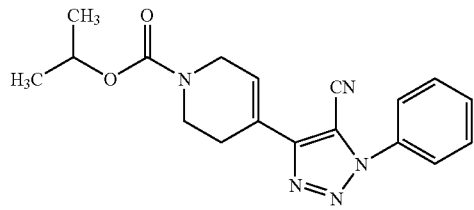

Isopropyl 4-[5-cyano-1-phenyl-1H-[1,2,3]triazol-4-yl]-1,2,3,6-tetrahydropyridine-carboxylate 1) Production of ethyl 3-phenyl-5-trimethylsilanyl-1H-[1,2,3]triazole-2-carboxylate Ethyl 3-(trimethylsilyl)propionate (4.0 g) was added to a solution of 800 mg of the phanylazide which is the compound of Example 7-1 in 10 ml of toluene and the mixture was stirred at 120° C. for 2 hours. The resulting solution was cooled down to room temperature and purified by a silica gel column chromatography (hexane/ethyl acetate=5/1) to give 450 mg of the title compound as a yellow oily crude product.

$^1$HNMR (400 MHz, CDCl$_3$) δ: 0.44 (9H, s), 1.21-1.23 (3H, m), 4.24-4.26 (2H, m), 6.90-7.50 (5H, m)

ESI-MS Found: m/z 290.1 [M+H]+.

2) Production of 3-phenyl-5-trimethylsilanyl-1H-[1,2,3]triazole-2-carboxylic acid Ethyl 3-phenyl-5-trimethylsilanyl-1H-[1,2,3]triazole-2-carboxylate (3.0 mg) which is the compound prepared in the above 2) was dissolved in 20 ml of tetrahydrofuran/water, 1.0 ml of 3N lithium hydroxide was dropped thereinto and the mixture was stirred at room temperature for one night. The solvent was evaporated in vacuo, a saturated aqueous solution of sodium hydrogen carbonate was added to the residue, the mixture was subjected to a back extraction with ethyl acetate, an aqueous layer was neutralized with 1M hydrochloric acid and extracted with ethyl acetate and the ethyl acetate layer washed with a saturated saline solution and dried over sodium sulfate. The solvent was evaporated in vacuo to give 630 mg of the title compound as a white solid.

$^1$HNMR (400 MHz, CDCl$_3$) δ: 0.42 (9H, s), 7.42-7.49 (5H, m)

ESI-MS Found: m/z 262.2 [M+H]+.

3) Production of 3-phenyl-5-trimethylsilanyl-1H-[1,2,3]triazole-2-carboxylic acid amide In a nitrogen atmosphere, 630 mg of 3-phenyl-5-trimethylsilanyl-1H-[1,2,3]triazole-2-carboxylic acid which is the compound prepared in the above 2) was dissolved in 5 ml of dichloromethane, 671 mg of 1-hydroxybenzotriazole monohydrate and 907 mg of a water-soluble dichlorohexyl carbodiimide were added thereto, the reaction solution was cooled down to −78° C. and ammonia gas was introduced thereinto followed by stirring for 2 days. Water was added to the reaction solution, the mixture was extracted with ethyl acetate and the ethyl acetate layer washed with a saturated saline solution and dried over sodium sulfate. The solvent was evaporated in vacuo and the residue was separated and purified by a silica gel column chromatography (hexane/ethyl acetate=2/1) to give 550 mg of the title compound as a white solid.

4) Production of 3-phenyl-1H-[1,2,3]triazole-4-carbonitrile 3-phenyl-5-trimethylsilanyl-1H-[1,2,3]triazole-2-carboxylic acid amide (550 mg) which is the compound prepared in the above 3) was dissolved in 2.0 ml of pyridine, 801 mg of 4-methylbenzenesulfonic acid chloride was added thereto and the mixture was stirred at 130° C. for one day. Water was added to the reaction solution, the mixture was extracted with ethyl acetate and the ethyl acetate layer washed with a saturated saline solution and dried over sodium sulfate. After the solvent was evaporated in vacuo and the residue was separated and purified by a thin-layer chromatography (hexane/ethyl acetate=5/1) to give 113 mg of the title compound as a white solid.

$^1$HNMR (400 MHz, CDCl$_3$) δ: 7.60-7.76 (5H, m), 8.30 (1H,s)

5) Production of 3-(2-fluoropyridin-3-yl)-5-iodo-4-carbonitrile-1H-[1,2,3]triazole In a nitrogen stream, 113 mg of 3-phenyl-1H-[1,2,3]triazole-4-carbonitrile which is the compound prepared in the above 4) was dissolved in 3.0 ml of tetrahydrofuran, the reaction solution was cooled at −78° C., 0.85 ml of 1.57M n-butyl lithium/hexane solution was dropped thereinto, the mixture was stirred for 5 minutes, 503 mg of iodine was added and the mixture was stirred for 2 hours by raising the temperature up to room temperature. A saturated aqueous solution of ammonium chloride was added to the reaction solution and the solvent was evaporated in vacuo. The residue was extracted with ethyl acetate and the ethyl acetate layer washed with a saturated aqueous solution of sodium thiosulfate and a saturated saline solution and dried over sodium sulfate. The solvent was evaporated in vacuo and the residue was separate and purified by a thin-layer chromatography (hexane/ethyl acetate=2/1) to give 44 mg of the title compound as a white solid.

6) Production of propyl 4-(4,4,5,5-tetramethyl-[1,3,2]dioxaboran-2-yl)-1,2,3,6-tetrahydropyridine-1-carboxylate Diisopropylamine (4.2 ml) was dissolved in 20 ml of tetrahydrofuran and cooled at −78° C. and 19 ml of a solution of 1.58M n-butyl lithium in hexane was dropped thereinto. After the temperature thereof was raised to 0° C., it was cooled down to −78° C. again and 10 ml of a solution of 3.70 g of isopropyl 4-oxopiperidine-1-carboxylate in tetrahydrofuran was dropped thereinto. After the mixture was stirred at −78° C. for 5 minutes, a solution of 7.15 g of N-phenyltrifluoromethane sulfonimide in 10 ml of tetrahydrofuran was added thereto. After the reaction solution was warmed up to room temperature and stirred for one night, reaction was stopped by water. The product was extracted with ethyl acetate and the extract washed with water for four times and dried over sodium sulfate. The solvent was evaporated in vacuo, 50 ml of 1,4-dioxane, 2.94 g of potassium acetate, 2.54 g of bis(pinacolate) diborane, 408 mg of [1,1-bis(diphenylphosphino)-ferrocene]dichloropalladium and 277 mg of 1,1-bis(diphenylphosphino)-ferrocene were added to the resulting residue and the mixture was stirred at 80° C. for one night. The reaction solution was cooled down to room temperature and filtered through Celite and the filtrate was concentrated in vacuo. The resulting residue was purified by a silica gel column chromatography (hexane/ethyl acetate=2:1) to give 1.31 g of the title compound.

$^1$HNMR (300 MHz, CDCl$_3$) δ: 1.20-1.30 (18H, m), 2.18-2.28 (2H, m), 3.42-3.52 (2H, m), 3.92-4.02 (2H, m), 4.93 (1H, sept, J=5.9 Hz), 6.47 (1H, br)

7) Production of isopropyl 4-[5-cyano-1-phenyl-1H-[1,2,3]triazol-4-yl]-1,2,3,6-tetrahydropyridine-carboxylate In a nitrogen atmosphere, 10 mg of 3-(2-fluoropyridin-3-yl)-5-iodo-4-carbonitrile-1H-[1,2,3]-triazole prepared in the above 5), 19 mg of isopropyl 4-(4,4,5,5-tetramethyl-[1,3,2] dioxaboran-2-yl)-1,2,3,6-tetrahydropyridine-carboxylate prepared in the above 6) and 5 mg of potassium carbonate were dissolved in 3 ml of N,N-dimethylformamide, 5 mg of [1,1-bis(diphenylphosphino)-ferrocene]dichloropalladium was added thereto and the mixture was stirred for one night with heating at 80° C. The reaction solution was cooled down to room temperature and insoluble matters were removed by filtering through Celite. Water was added to the filtrate, the mixture was extracted with diethyl ether and diethyl ether layer washed with a saturated saline solution and dried over sodium sulfate. The solvent was evaporated in vacuo and the residue was separate and purified by a thin-layer chromatography (hexane/ethyl acetate=2/1) to give 4.03 mg of the title compound as a white solid.

$^1$HNMR (400 MHz, CDCl$_3$) δ: 1.27-1.29 (6H, m), 2.79 (2H, br), 3.71-3.74 (2H, m), 4.22 (2H, br), 4.95-5.01 (1H, m), 6.81 (1H, br), 7.57-7.63 (3H, m), 7.72-7.74 (2H, m)

ESI-MS Found: m/z 338.2 [M+H]+.

Example 46

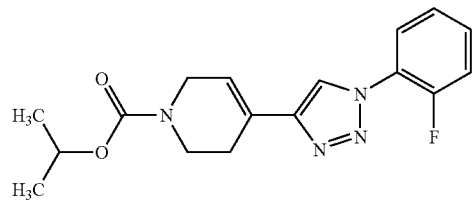

Isopropyl 4-[1-(2-fluorophenyl)-1H-[1,2,3]triazol-4-yl]-1,2,3,6-tetrahydropyridine-1-carboxylate 1) Production of 4-[1-(2-fluorophenyl)-1H-[1,2,3]-triazol-4-yl]-1,2,3,6-tetrahydropyridine hydrochloride tert-Butyl 4-[1-(2-fluorophenyl)-1H-[1,2,3]triazol-4-yl]-1,2,3,6-tetrahydropyridine-1-carboxylate (70 mg) prepared in Example 5 was dissolved in 2.0 ml of 4N hydrochloric acid/ethyl acetate solution followed by stirring at room temperature for 30 minutes. The solvent was evaporated in vacuo to give the title compound as a brown crude product.

2) Production of isopropyl 4-[1-(2-fluorophenyl)-1H-[1,2,3]triazol-4-yl]-1,2,3,6-tetrahydropyridine-1-carboxylate 4-[1-(2-Fluorophenyl)-1H-[1,2,3]-triazol-4-yl]-1,2,3,6-tetrahydropyridine hydrochloride (22.7 mg) prepared in the above 1) was dissolved in 0.5 ml of pyridine and 0.06 ml of isopropyl chloroformate was added thereto followed by stirring for 1 hour. A saturated aqueous solution of ammonium chloride was added to the reaction solution and the product was extracted with ethyl acetate, dried over sodium sulfate and the solvent was evaporated in vacuo. The resulting residue was separated and purified by a thin-layer chromatography (ethyl acetate/hexane=1/1) to give 4.9 mg of the title compound as a white solid.

$^1$HNMR (400 MHz, CDCl$_3$) δ: 1.28 (6H, d, J=3.11 Hz), 2.58-2.62 (2H, m), 3.68-3.72 (2H, m), 4.15 (2H, m), 4.96 (1H, p, J=3.11 Hz), 6.53 (1H, brs), 7.24-7.31 (2H, m), 7.40-7.43 (2H, m), 7.93-7.97 (1H, m)

ESI-MS Found: m/z 331.3 [M+H]+.

Example 47

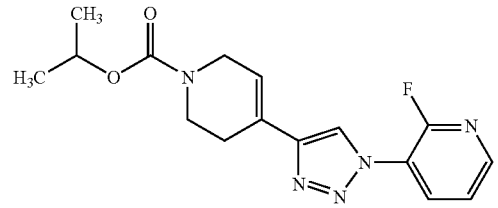

Isopropyl 4-[1-(2-fluoropyridin-3-yl)-1H-[1,2,3]-triazol-4-yl]-1,2,3,6-tetrahydropyridine-1-carboxylate 1) 4-[1-(2-fluoropyridin-3-yl)-1H-[1,2,3]triazol-4-yl]-1,2,3,6-tetrahydropyridine formate tert-Butyl 4-[1-(2-fluoropyridin-3-yl)-1H-[1,2,3]-triazol-4-yl]-1,2,3,6-tetrahydropyridine-1-carboxylate (24 mg) prepared in Example 4 was dissolved in 2 ml of formic acid, followed by stirring for one night at room temperature and the solvent was evaporated in vacuo to give the title compound as a mixture.

2) Production of isopropyl 4-[1-(2-fluoropyridin-3-yl)-1H-[1,2,3]-triazol-4-yl]-1,2,3,6-tetrahydropyridine-1-carboxylate Pyridine (2 ml) and 0.15 ml of isopropyl chloroformate were added to the amine substance prepared in 1) followed by stirring at room temperature for 1.5 hours. The reaction was stopped by a saturated sodium hydrogen carbonate solution, the product was extracted with ethyl acetate and the organic layer washed with a saturated aqueous solution of ammonium chloride and dried over sodium sulfate. After the solvent was evaporated in vacuo, the residue was separated and purified by a silica gel thin-layer chromatography (ethyl acetate) to give 5.0 mg of the title product as a colorless oily substance.

$^1$HNMR (300 MHz, CDCl$_3$) δ: 1.28 (6H, t, J=6.2 Hz), 2.53-2.62 (2H, m), 3.66-3.78 (2H, m), 4.11-4.20 (2H, m), 4.98 (1H, sept, J=6.2 Hz), 6.51-6.60 (1H, m), 7.39-7.49 (1H, m), 8.01-8.10 (1H, m), 8.26-8.32 (1H, m), 8.46-8.55 (1H, m)

ESI-MS Found: m/z 332.1 [M+H]+.

Example 48

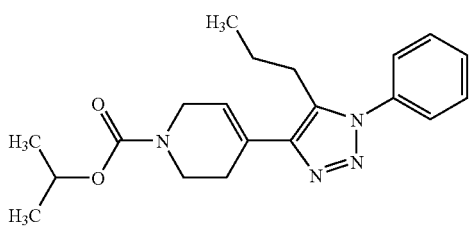

Isopropyl 4-[1-phenyl-5-propyl-1H-[1,2,3]triazol-4-yl]-1,2,3,6-tetrahydropyridine-carboxylate 1) Production of 1-phenyl-5-propyl-4-trimethylsilanyl-1H-[1,2,3]triazole Reaction was carried out by the same method as in Example 45-1 except that trimethyl-1-pentynylsilane was used in place of ethyl 3-(trimethylsilyl)propionate of Example 45-1 to give the title compound.

$^1$HNMR (400 MHz, CDCl$_3$) δ: 0.40 (9H, s), 0.79-0.40 (3H, m), 1.37 (2H, m), 2.65-2.69 (2H, m), 7.37-7.51 (5H, m)

ESI-MS Found: m/z 260.3 [M+H]+.

2) Production of 4-iodo-1-phenyl-5-propyl-1H-[1,2,3]-triazole

1-Phenyl-5-propyl-4-trimethylsilanyl-1H-[1,2,3]-triazole (260 mg) prepared in the above 1) was dissolved in 5.0 ml of tetrahydrofuran, 389 mg of silver tetrafluoroborate and 507 mg of iodine were added thereto and the mixture was stirred at room temperature for one night. The reaction solution was filtered through Celite, a saturated aqueous solution of sodium thiosulfate was added to the filtrate and the solvent was evaporated in vacuo. Water was added to the residue, the mixture was extracted with ethyl acetate and the ethyl acetate layer washed with a saturated saline solution and dried over sodium sulfate. After the solvent was evaporated in vacuo, the residue was separated and purified by a silica gel column chromatography (hexane/ethyl acetate=2/1) to give 180 mg of the title compound as a white solid.

$^1$HNMR (400 MHz, CDCl$_3$) δ: 0.83-0.87 (3H, m), 1.46-1.53 (2H, m), 2.65-2.69 (2H, m), 7.38-7.40 (2H, m), 7.52-7.54 (3H, m)

ESI-MS Found: m/z 314.1 [M+H]+.

3) Production of isopropyl 4-[1-phenyl-5-propyl-1H-[1,2,3]triazol-4-yl]-1,2,3,6-tetrahydropyridine-carboxylate In a nitrogen atmosphere, 30 mg of 4-iodo-1-phenyl-5-propyl-1H-[1,2,3]-triazole prepared in the above 2), 34 mg of isopropyl 4-(4,4,5,5-tetramethyl-[1,3,2]dioxaboran-2-yl)-1,2,3,6-tetrahydropyridine-carboxylate prepared in Example 45-6 and 26 mg of potassium carbonate were dissolved in 3 ml of N,N-dimethylformamide, 7.7 mg of [1,1-bis(diphenylphosphino)-ferrocene]dichloropalladium was added thereto and the mixture was stirred with heating at 80° C. for one night. After the reaction solution was cooled down to room temperature, insoluble matters were removed by filtering through Celite. Water was added to the filtrate, the mixture was extracted with diethyl ether and the diethyl ether layer washed with a saturated saline solution and dried over sodium sulfate. After the solvent was evaporated in vacuo, the residue was separated and purified by a thin-layer chromatography (hexane/ethyl acetate=2/1) to give 9.04 mg of a white solid.

$^1$HNMR (400 MHz, CDCl$_3$) δ: 0.80-0.85 (3H, m), 1.27 (6H, d, J=6.0 Hz), 1.40-1.46 (2H, m), 2.68-2.74 (4H, m), 3.68-3.71 (2H, m), 4.14 (2H, br), 4.95-4.98 (1H, m), 6.00 (1H, br), 7.38-7.41 (2H, m), 7.51-7.54 (3H, m)

ESI-MS Found: m/z 355.3 [M+H]+.

Example 49

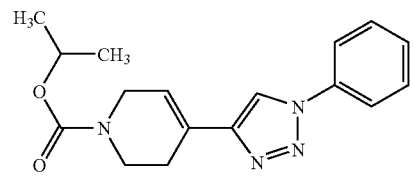

Isopropyl 4-[1-phenyl-1H-[1,2,3]triazol-4-yl]-1,2,3,6-tetrahydropyridine-1-carboxylate 1) Production of 4-[1-phenyl-1H-[1,2,3]triazol-4-yl]-1,2,3,6-tetrahydropyridine tert-Butyl 4-[1-phenyl-1H-[1,2,3]triazol-4-yl]-1,2,3,6-tetrahydropyridine-1-carboxylate (50 mg) was dissolved in 1 ml of formic acid followed by stirring at room temperature for 4 hours. After formic acid was evaporated in vacuo, the residue was dissolved in chloroform and washed with a saturate aqueous solution of sodium bicarbonate and then with a saturated saline solution. After the organic layer was dried over sodium sulfate, the solvent was evaporated in vacuo to give 35 mg of crude product of the title compound as an oily substance.

2) Production of isopropyl 4-[1-phenyl-1H-[1,2,3]-triazol-4-yl]-1,2,3,6-tetrahydropyridine-1-carboxylate 4-[1-phenyl-1H-[1,2,3]triazol-4-yl]-1,2,3,6-tetra-hydropyridine (35 mg) prepared in the above 1) was dissolved in 1 ml of pyridine and 1 ml of chloroform, 32 µl of isopropyl chloroformate was added and the mixture was stirred at room temperature for 1 hour. After an excessive reagent was decomposed by addition of methanol, the reaction solution was concentrated in vacuo and the resulting residue was separated and purified by a preparative thin-layer chromatography (chloroform/methanol 60/1) to give 47 mg of the title compound as a white solid.

¹HNMR (300 MHz, CDCl₃) δ: 1.28 (6H, d.J=6.3 Hz), 2.60 (2H, bs), 3.72 (2H, t, J=5.5 Hz), 4.12-4.19 (2H, m), 4.91-5.04 (1H, m), 6.53 (1H, bs), 7.44 (1H, t, J=7.1 Hz), 7.53 (2H, t, J=8.4 Hz), 7.74 (2H, d, J=8.2 Hz), 7.88 (1H, s)

ESI-MS Found: m/z 313.3 [M+H]+.

Example 50

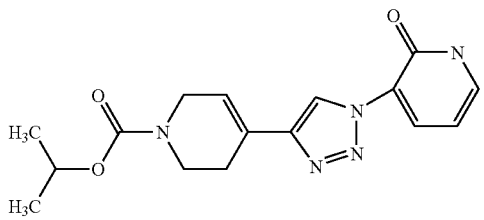

Isopropyl 4-[1-(2(1H)-pyridon-3-yl)-1H-[1,2,3]-triazol-4-yl]-1,2,3,6-tetrahydropyridine-1-carboxylate As a by-product of Example 47, 3.4 mg of the title compound was prepared as a light yellow oily substance.

¹HNMR (300 MHz, CDCl₃) δ: 1.27 (6H, d, J=6.3 Hz), 2.55-2.66 (2H, m), 3.64-3.76 (2H, m), 4.08-4.21 (2H, m), 4.97 (1H, sept, J=6.3 Hz), 6.48-6.58 (2H, m), 7.46 (1H, dd, J=1.6, 6.6 Hz), 8.38 (1H, dd, J=1.6, 7.7 Hz), 8.72 (1H, s), 11.72-12.02 (1H, brs)

ESI-MS Found: m/z 330.1 [M+H]+.

Example 51

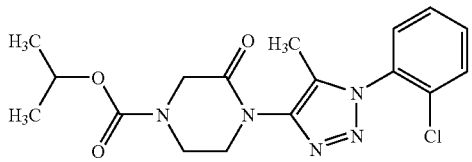

Isopropyl 4-[1-(2-chlorophenyl)-5-methyl-1H-[1,2,3]-triazol-4-yl]-3-oxopiperazine-1-carboxylate 1) Production of 4-[1-(2-chlorophenyl)-5-methyl-1H-[1,2,3]triazol-4-yl]-3-oxopiperazine 4N Hydrochloric acid solution in dioxane (10 ml) was added to 150 mg of tert-butyl 4-[1-(2-chlorophenyl)-5-methyl-1H-[1,2,3]-triazol-4-yl]-3-oxopiperazine-1-carboxylate prepared in Example 26, the mixture was stirred at room temperature for 3 hours and the solvent was evaporated in vacuo to give 110 mg of the title compound as a white solid.

ESI-MS Found: m/z 292.2 [M+H]+.

2) Isopropyl 4-[1-(2-chlorophenyl)-5-methyl-1H-[1,2,3]triazol-4-yl]-3-oxopiperazine-1-carboxylate In a nitrogen atmosphere, 8 mg of the compound prepared in the above 1) was dissolved in 1 ml of chloroform, 0.03 ml of isopropyl chloroformate and 0.06 ml of triethylamine were added thereto and the mixture was stirred at room temperature for 2 hours. After the solvent was evaporate in vacuo, the resulting residue was purified by a preparative thin-layer silica gel chromatography (chloroform:methanol=9:1) to give 8 mg of the title compound as a white solid.

¹HNMR (400 MHz, CDCl₃) δ: 1.30 (6H, d, J=6.4 Hz), 2.12 (3H, s), 3.89 (2H, t, J=5.0 Hz), 4.02 (2H, t, J=5.4 Hz), 4.31 (2H, s), 4.94-5.02 (1H, m), 7.45-7.61 (4H, m)

Example 52

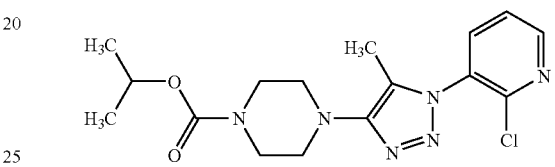

Isopropyl 4-[1-(2-chloropyridin-3-yl)-5-methyl-1H-[1,2,3]triazol-4-yl]-piperazine-1-carboxylate 4N Hydrochloric acid solution in dioxane (10 ml) was added to 3 mg of tert-Butyl 4-[1-(2-chloropyridin-3-yl)-5-methyl-1H-[1,2,3]triazol-4-yl)-piperazine-1-carboxylate prepared in Example 34, the mixture was stirred at room temperature for 3 hours, the solvent was evaporated in vacuo, the residue was dissolved in 1 ml of chloroform and, in a nitrogen atmosphere, 0.03 ml of isopropyl chloroformate and 0.06 ml of triethylamine were added thereto and the mixture was stirred at room temperature for 2 hours. After the solvent was evaporated in vacuo, the resulting residue was purified by a preparative thin-layer silica gel chromatography (chloroform:methanol=9:1) to give 2 mg of the title compound as a white solid.

¹HNMR (400 MHz, CDCl₃) δ: 1.27 (6H, d, J=6.4), 2.17 (3H, s), 3.15-3.22 (4H, m), 3.60-3.47 (4H, m), 4.90-5.00 (1H, m), 7.40-7.50 (1H, m), 7.75-7.85 (1H, m), 8.55-8.60 (1H, m)

ESI-MS Found: m/z 365.3 [M+2H]+.

Example 53

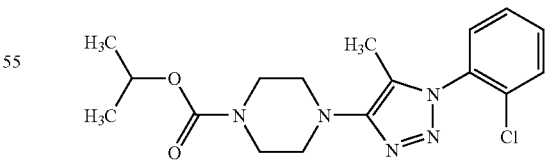

Isopropyl 4-[1-(2-chlorophenyl)-5-methyl-1H-[1,2,3]-triazol-4-yl-piperazine-1-carboxylate A boran-methyl sulfide complex (0.5 ml) was added to 10 mg of 1-tert-butyl 4-[1-(2-chlorophenyl)-5-methyl-1H-[1,2,3]-triazol-4-yl]-3-oxopiperazine-1-carboxylate prepared in Example 26 followed by stirring at room temperature for 1 hour. After pyridine was added thereto, 3 ml of 4N hydrochloric acid/dioxane solution was added to the residue obtained by evaporation of the solvent in vacuo and the resulting solution was stirred for 3 hours at room temperature. Thereafter, the residue obtained by evaporation of the solvent in vacuo was dissolved in 1 ml of chloroform and, in a nitrogen atmosphere, 0.1 ml of isopropyl chlorocarbonate and 0.2 ml of triethylamine were added thereto followed by stirring at room temperature for 2 hours. After the solvent was evaporated in vacuo, the resulting residue was purified by a preparative thin-layer silica gel chromatography (chloroform:methanol=9:1) to give 8 mg of the title compound as a white solid.

$^1$HNMR (400 MHz, CDCl$_3$) δ: 1.27 (6H, d, J=6.0 Hz), 2.12 (3H, s), 3.18 (4H, t, J=5.0 Hz), 3.63 (4H, t, J=5.2 Hz), 4.91-4.99 (1H, m), 7.38-7.60 (4H, m)

ESI-MS Found: m/z 364.3 [M+H]+.

Example 54

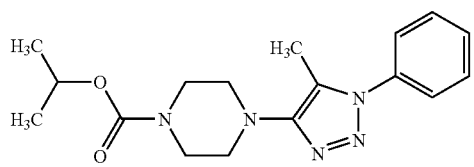

Isopropyl 4-(5-methyl-1-phenyl-1H-[1,2,3]triazol-4-yl)-piperazine-1-carboxylate 4N hydrochloric acid solution in dioxane (3 ml) was added to 7 mg of 1-tert-butyl 4-[5-methyl-1-phenyl-1H-[1,2,3]triazol-4-yl]-piperazine-1-carboxylate followed by stirring at room temperature for 3 hours, the solvent was evaporated in vacuo therefrom, the resulting residue was dissolved in 1 ml of chloroform and, in a nitrogen atmosphere, 0.1 ml of isopropyl chloroformate and 0.2 ml of triethylamine were added thereto followed by stirring for one night at room temperature. After the solvent was evaporated in vacuo, the resulting residue was purified by a preparative thin-layer silica gel chromatography (chloroform:methanol=9:1) to give 2 mg of the title compound as a white solid.

$^1$HNMR (400 MHz, CDCl$_3$) δ: 1.27 (6H, d, J=6.0 Hz), 2.26 (3H, s), 3.11-3.20 (4H, m), 3.58-3.67 (4H, m), 4.90-5.00 (1H, m), 7.40-7.57 (5H, m)

ESI-MS Found: m/z 330.2 [M+H]+.

Example 55

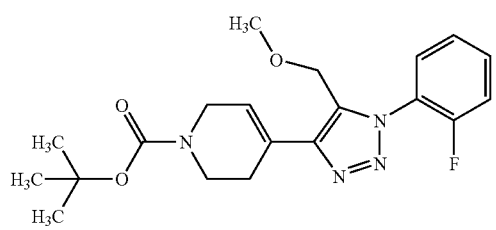

tert-Butyl 4-[1-(2-fluorophenyl)-5-methoxymethyl-1H-[1,2,3]triazol-4-yl]-1,2,3,6-tetrahydropyridine-carboxylate Reaction was carried out by the same method as in Example 14-1, 2 and 3 to give the title compound.

$^1$HNMR (400 MHz, CDCl$_3$) δ: 1.49 (9H, s), 2.74-2.77 (2H, m), 3.20 (3H, s), 3.65-3.68 (2H, m), 4.11-4.12 (2H, m), 4.38 (2H, s), 6.17 (1H, br), 7.24-7.34 (2H, m), 7.48-7.54 (2H, m)

ESI-MS Found: m/z 389.2 [M+H]+.

Example 56

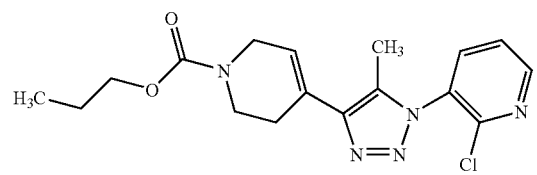

Propyl 4-[1-(2-chloropyridin-3-yl)-5-methyl-1H-[1,2,3]triazol-4-yl]-1,2,3,6-tetrahydropyridine-1-carboxylate Methylene chloride (2 ml), 0.04 ml of triethylamine and 0.02 ml of n-propyl chloroformate were added to 6.0 mg of the amine substance prepared in 1) of Example 42 followed by stirring at room temperature for one night. After the solvent was evaporated in vacuo, the residue was separated and purified by a silica gel thin-layer chromatography (ethyl acetate) to give 5.5 mg of the title compound as a colorless amorphous substance.

$^1$HNMR (300 MHz, CDCl$_3$) δ: 0.98 (3H, t, J=7.4 Hz), 1.61-1.78 (2H, m), 2.30 (3H, s), 2.72-2.83 (2H, m), 3.68-3.78 (2H, m), 4.11 (2H, t, J=6.6 Hz), 4.12-4.23 (2H, m), 6.02-6.12 (1H, m), 7.50 (1H, dd, J=1.8, 4.8 Hz), 7.82 (1H, dd, J=1.8, 7.7 Hz), 8.62 (1H, dd, J=1.8, 4.8 Hz)

ESI-MS Found: m/z 362.1 [M+H]+.

Example 57

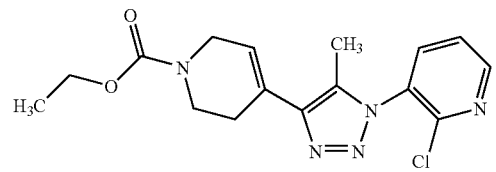

Ethyl 4-[1-(2-chloropyridin-3-yl)-1H-[1,2,3]triazol-4-yl]-1,2,3,6-tetrahydropyridine-1-carboxylate Methylene chloride (2 ml), 0.04 ml of triethylamine and 0.02 ml of ethyl chloroformate were added to 6.0 mg of the amine substance prepared in 1) of Example 42 followed by stirring at room temperature for one night. After the solvent was evaporated in vacuo, the residue was separated and purified by a silica gel thin-layer chromatography (ethyl acetate) to give 6.2 mg of the title compound as a colorless amorphous substance.

$^1$HNMR (300 MHz, CDCl$_3$) δ: 1.30 (3H, t, J=7.1 Hz), 2.29 (3H, s), 2.71-2.81 (2H, m), 3.64-3.77 (2H, m), 4.12-4.23 (4H, m), 6.02-6.11 (1H, m), 7.50 (1H, dd, J=4.8, 7.8 Hz), 7.81 (1H, dd, J=1.7, 7.8 Hz), 8.61 (1H, dd, J=1.7, 4.8 Hz)

ESI-MS Found: m/z 348.1 [M+H]+.

Example 58

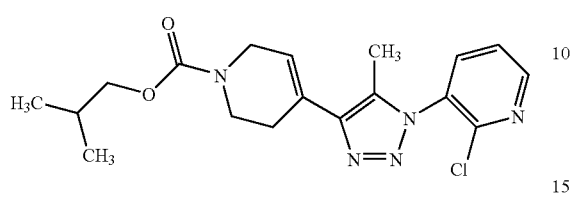

2-Methylpropyl 4-[1-(2-chloropyridin-3-yl)-5-methyl-1H-[1,2,3]-triazol-4-yl]-1,2,3,6-tetrahydropyridine-1-carboxylate Methylene chloride (2 ml), 0.04 ml of triethylamine and 0.02 ml of isobutyl chloroformate were added to 6.0 mg of the amine substance prepared in 1) of Example 42 followed by stirring at room temperature for one night. After the solvent was evaporated in vacuo, the residue was separated and purified by a silica gel thin-layer chromatography (ethyl acetate) to give 5.8 mg of the title compound as a colorless amorphous substance.

$^1$HNMR (300 MHz, CDCl$_3$) δ: 0.97 (6H, d, J=6.7 Hz), 1.88-2.08 (1H, m), 2.30 (3H, s), 2.74-2.85 (2H, m), 3.70-3.79 (2H, m), 3.92 (2H, d, J=6.7 Hz), 4.15-4.22 (2H, m), 6.04-6.13 (1H, m), 7.50 (1H, dd, J=4.8, 7.8 Hz), 7.83 (1H, dd, J=1.8, 7.8 Hz), 8.62 (1H, dd, J=1.8, 4.8 Hz)

ESI-MS Found: m/z 376.1 [M+H]+.

Example 59

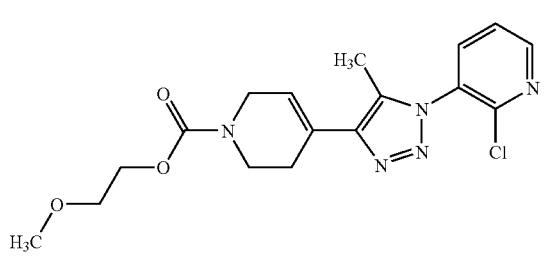

Methoxyethyl 4-[1-(2-chloropyridin-3-yl)-[1,2,3]-triazol-4-yl]-1,2,3,6-tetrahydropyridine-1-carboxylate 2-Chloro-3-[5-methyl-4-(1,2,3,6-tetrahydropyridin-4-yl)-[1,2,3]triazol-1-yl]-pyridine hydrochloride (3.0 mg) prepared in Example 42-1 was dissolved in 1.0 ml of dichloromethane and 0.02 ml of triethylamine and 0.02 ml of 2-methoxyethyl chloroformate were added thereto followed by stirring at room temperature for 10 minutes. The solvent was evaporated in vacuo and the residue was separated and purified by a thin-layer chromatography (ethyl acetate) to give 1.36 mg of the title compound as a white solid.

$^1$HNMR (400 MHz, CDCl$_3$) δ: 2.28 (3H, s), 2.77 (2H, br), 3.40 (3H, s), 3.63 (2H, t, J=3.2 Hz), 3.72 (2H, t, J=6.0 Hz), 4.18-4.19 (2H, br), 4.27-4.30 (2H, m), 6.05 (1H, br), 7.48 (1H, dd, J=4.8, 8.0 Hz), 7.80 (1H, dd, J=1.6, 8.0 Hz), 8.60 (1H, dd, J=1.6, 4.8 Hz)

ESI-MS Found: m/z 378.1 [M+H]+.

Example 60

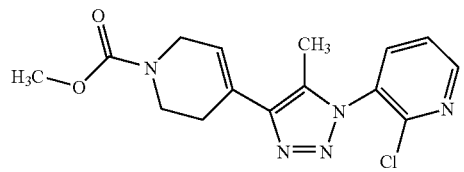

Methyl 4-[1-(2-chloropyridin-3-yl)-5-methyl-1H-[1,2,3]-triazol-4-yl]-1,2,3,6-tetrahydropyridine-1-carboxylate Methylene chloride (0.5 ml), 0.05 mol of triethylamine and 0.02 ml of ethyl chloroformate were added to 2.3 mg of the amine substance prepared in 1) of Example 42 followed by stirring at room temperature for 10 minutes. After the solvent was evaporated in vacuo, the residue was separated and purified by a silica gel thin-layer chromatography (ethyl acetate) to give 2.2 mg of the title compound as a colorless amorphous substance.

$^1$HNMR (300 MHz, CDCl$_3$) δ: 2.29 (3H, s), 2.71-2.82 (2H, m), 3.68-3.79 (5H, m), 4.11-4.21 (2H, m), 6.02-6.10 (1H, m), 7.45-7.52 (1H, m), 7.79-7.86 (1H, m), 8.59-8.65 (1H, m)

ESI-MS Found: m/z 334.1 [M+H]+.

Example 61, Example 62

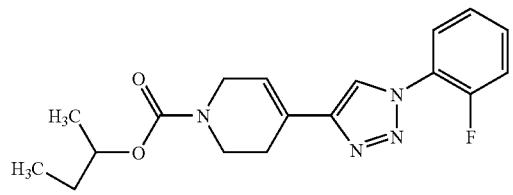

1-Methylpropyl 4-[1-(2-fluorophenyl)-1H-[1,2,3]-triazol-4-yl]-1,2,3,6-tetrahydropyridine-1-carboxylate Racemic 2-butanol (54 μl) was dissolved in 3 ml of methylene chloride, 96 mg of dimidazole carbodiimide was added thereto followed by stirring at room temperature for one night and the solvent was evaporated in vacuo. To the resulting residue were added 28 mg of the amine substance prepared in 1) of Example 46, 0.1 ml of diisopropylethylamine and 3.0 ml of 1,2-dichloroethane followed by stirring under heating to reflux for 3 hours. After cooling down to room temperature, a 40% methanolic solution of methylamine was added followed by stirring for 1 hour. After the solvent was evaporated in vacuo, the residue was separated and purified by a silica gel thin-layer column chromatography (ethyl acetate/hexane=2/3) to give 32 mg of a racemic title compound in a colorless oily substance.

The resulting racemic compound was subjected to an optical resolution using an optically active column (Chiralpak AD Column manufactured by Daicel; hexane/isopropanol/diethylamine=4/1/0.1) to give 4.30 mg of a compound which was called, for the sake of convenience, as a (2R*) substance of the title compound from the earlier fraction and 4.11 mg of another compound which was called, for the sake of convenience, as a (2S*) substance of the title compound from the latter fraction both being as a colorless oily product.

$^1$HNMR (200 MHz, CDCl$_3$) δ: 0.93 (3H, t, J=7.4 Hz), 1.24 (3H, d, J=6.3 Hz), 1.41-1.72 (2H, m), 2.51-2.68 (2H, m), 365-3.78 (2H, m), 4.10-4.20 (2H, m), 4.69-4.90 (1H, m), 6.48-6.60 (1H, m), 7.10-7.51 (3H, m), 7.87-8.04 (2H, m)

ESI-MS Found: m/z 345.1 [M+H]+.

Example 63

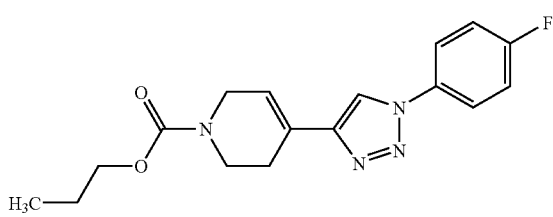

Propyl 4-[1-(4-fluorophenyl)-1H-[1,2,3]triazol-4-yl]-1,2,3,6-tetrahydropyridine-1-carboxylate 1) 4-(1-(4-fluorophenyl)-1H-[1,2,3]-triazol-4-yl)-1,2,3,6-tetrahydropyridine tert-Butyl 4-[1-(4-fluorophenyl)-1H-[1,2,3]triazol-4-yl]-1,2,3,6-tetrahydropyridine-1-carboxylate (50 mg) prepared in Example 13 was dissolved in 4.0 ml of 4N-hydrochloric acid/ethyl acetate, the mixture was stirred for one night and, after evaporation of the solvent in vacuo, a saturate sodium hydrogen carbonate and chloroform were added. The organic layer was dried over sodium sulfate and the solvent was evaporated in vacuo to give the title compound as a mixture.

2) Production of propyl 4-[1-(4-fluorophenyl)-1H-[1,2,3]triazol-4-yl]-1,2,3,6-tetrahydropyridine-1-carboxylate Pyridine (2.0 ml) and 0.15 ml of n-propyl chloroformate were added to 15 mg of the amine substance prepared in 1) followed by stirring at room temperature for 30 minutes. The reaction was stopped with water, the product was extracted with ethyl acetate and the organic layer washed with a saturated aqueous solution of ammonium chloride and dried over sodium sulfate. After the solvent was evaporated in vacuo, the residue was separated and purified by a silica gel column chromatography (hexane/ethyl acetate=3/2) to give 18.2 mg of the title compound as a white solid.

$^1$HNMR (300 MHz, CDCl$_3$) δ: 0.97 (3H, t, J=7.4 Hz), 1.60-1.76 (2H, m), 2.53-2.67 (2H, m), 3.68-3.78 (2H, m), 4.09 (2H, t, J=6.7 Hz), 4.12-4.20 (2H, m), 6.47-6.58 (1H, m), 7.15-7.30 (2H, m), 7.64-7.75 (2H, m), 7.82 (1H, s)

ESI-MS Found: m/z 331.1 [M+H]+.

Example 64

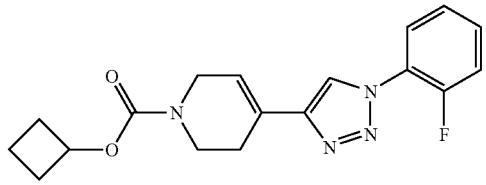

Cyclobutyl 4-[1-(2-fluorophenyl)-1H-[1,2,3]triazol-4-yl]-1,2,3,6-tetrahydropyridine-1-carboxylate Cyclobutanol (63 µl) was dissolved in 3 ml of methylene chloride, 97 mg of dimidazole carbodiimide was added thereto followed by stirring at room temperature for one night and the solvent was evaporated in vacuo. To the resulting residue were added 20 mg of the amine substance prepared in 1) of Example 46, 0.1 ml of diisopropylethylamine and 3.0 ml of 1,2-dichloroethane followed by stirring under heating to reflux for 3 hours. After cooling it down to room temperature, a 40% methylamine/methanol solution was added thereto followed by stirring for 1 hour. After the solvent was evaporated in vacuo, the residue was separated and purified by a silica gel thin-layer chromatography (ethyl acetate/hexane=2/3) and then by a silica gel thin-layer chromatography (chloroform/methanol 15/1) to give 13.9 mg of the title compound as a colorless oily product.

$^1$HNMR (300 MHz, CDCl$_3$) δ: 1.50-1.87 (2H, m), 1.96-2.19 (2H, m), 2.25-2.42 (2H, m), 2.53-2.69 (2H, m), 3.71 (2H, t, J=5.7 Hz), 4.10-4.12 (2H, m), 4.99 (1H, quin, J=7.1 Hz), 6.54 (1H, br), 7.22-7.49 (3H, m), 7.91-8.02 (2H, m)

ESI-MS Found: m/z 343.3 [M+H]+.

Example 65

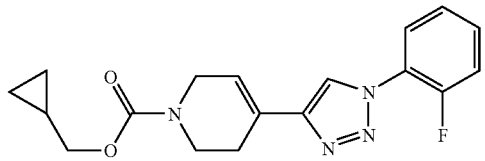

Cyclopropylmethyl 4-[1-(2-fluorophenyl)-1H-[1,2,3]-triazol-4-yl]-1,2,3,6-tetrahydropyridine-1-carboxylate Cyclopropanemethanol (65 µl) was dissolved in 3 ml of methylene chloride, 97 mg of dimidazole carbodiimide was added thereto followed by stirring at room temperature for one night and the solvent was evaporated in vacuo. To the resulting residue were added 20 mg of the amine substance prepared in 1) of Example 46, 0.1 ml of diisopropylethylamine and 3.0 ml of 1,2-dichloroethane followed by stirring under heating to reflux for 3 hours. After cooling it down to room temperature, a 40% methylamine/methanol solution was added thereto followed by stirring for 1 hour. After the solvent was evaporated in vacuo, the residue was separated and purified by a silica gel thin-layer column chromatography (ethyl acetate/hexane=1/2) and then by a silica gel thin-layer column chromatography (chloroform/methanol 15/1) to give 9.9 mg of the title compound as a colorless oily product.

$^1$HNMR (300 MHz, CDCl$_3$) δ: 0.22-0.33 (2H, m), 0.51-0.61 (2H, m), 1.08-1.23 (1H, m), 2.57-2.69 (2H, m), 3.74 (2H, t, J=5.8 Hz), 3.96 (2H, d, J=7.3 Hz), 4.15-4.22 (2H, m), 6.55 (1H, br), 7.22-7.49 (3H, m), 7.91-8.02 (2H, m)

ESI-MS Found: m/z 343.2 [M+H]+.

Example 66

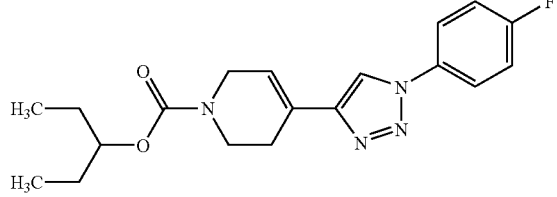

1-Ethylpropyl 4-[1-(4-fluorophenyl)-1H-[1,2,3]-triazol-4-yl]-1,2,3,6-tetrahydropyridine-1-carboxylate 2-Pentanol (21 μl) was dissolved in 1 ml of methylene chloride, 32 mg of dimidazole carbodiimide was added thereto followed by stirring at room temperature for one night and the solvent was evaporated in vacuo. To the resulting residue were added 50 mg of the amine substance prepared in 1) of Example 63, 0.1 ml of diisopropylethylamine and 3.0 ml of 1,2-dichloroethane followed by stirring under heating to reflux for 3 hours. After cooling it down to room temperature, a 40% methylamine/methanol solution was added thereto followed by stirring for 1 hour. After the solvent was evaporated in vacuo, the residue was separated and purified by a silica gel thin-layer chromatography (ethyl acetate/hexane=2/3) to give 7.8 mg of the title compound as a white solid.

$^1$HNMR (300 MHz, CDCl$_3$) δ: 0.92 (6H, t, J=7.5 Hz), 1.50-1.72 (4H, m), 2.53-2.68 (2H, m), 3.73 (2H, t, J=5.7 Hz), 4.13-4.21 (2H, m), 4.71 (1H, quin, 6.2 Hz), 6.45-6.69 (1H, m), 7.15-7.30 (2H, m), 7.65-7.75 (2H, m), 7.82 (1H, s)

ESI-MS Found: m/z 359.3 [M+H]+.

Example 67

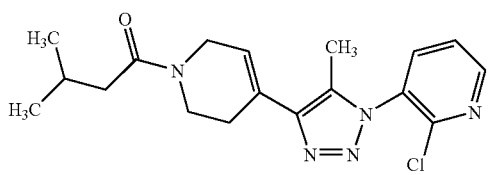

1-{4-[1-(2-chloropyridin-3-yl)-1H-[1,2,3]triazol-4-yl]-1,2,3,6-tetrahydropyridin-1-yl}-3-methyl-1-butanone To the amine substance (6.0 mg) prepared in 1) of Example 42 were added 1 ml of methylene chloride, 0.06 ml of triethylamine and 0.03 ml of isovaleryl chloride followed by stirring at room temperature for 1 hour. After the solvent was evaporated in vacuo, the residue was separated and purified by a silica gel thin-layer chromatography (ethyl acetate) to give 6.88 mg of the title compound as a colorless oily product.

$^1$HNMR (300 MHz, CDCl$_3$) δ: 0.87-1.20 (6H, m), 1.40-2.33 (6H, m), 2.66-2.90 (2H, m), 3.70-3.92 (2H, m), 4.15-4.36 (2H, m), 6.02-6.21 (1H, m), 7.45-7.54 (1H, m), 7.79-7.86 (1H, m), 8.59-8.67 (1H, m)

ESI-MS Found: m/z 360.2 [M+H]+.

Example 68

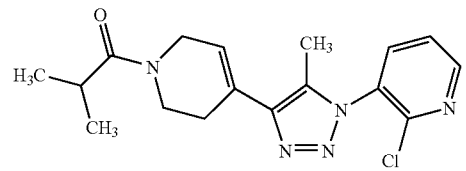

1-{4-[1-(2-chloropyridin-3-yl)-5-methyl-1H-[1,2,3]-triazol-4-yl]-1,2,3,6-tetrahydropyridin-1-yl}-2-methyl-1-propanone To the amine substance (6.0 mg) prepared in 1) of Example 42 were added 1 ml of methylene chloride, 0.06 ml of triethylamine and 0.03 ml of isobutyryl chloride followed by stirring at room temperature for 1 hour. After the solvent was evaporated in vacuo, the residue was separated and purified by a silica gel thin-layer chromatography (ethyl acetate) to give 6.76 mg of the title compound as a colorless oily product.

$^1$HNMR (300 MHz, CDCl$_3$) δ: 1.10-1.21 (6H, m), 2.30 (3H, s), 2.69-2.99 (3H, m), 3.70-3.92 (2H, m), 4.20-4.35 (2H, m), 6.01-6.20 (1H, m), 7.45-7.53 (1H, m), 7.79-7.85 (1H, m), 8.60-8.65 (1H, m)

ESI-MS Found: m/z 346.1 [M+H]+.

Example 69

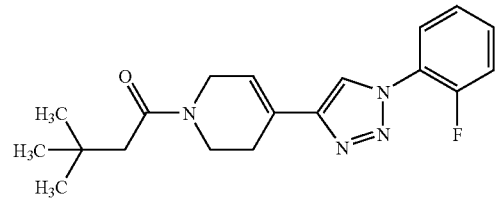

1-{4-[1-(2-fluorophenyl)1H-[1,2,3]triazol-4-yl]-1,2,3,6-tetrahydropyridin-1-yl}-3,3-dimethylbutan-1-one To the amine substance prepared in 1) of Example 46 were added 3 ml of chloroform, 0.1 ml of triethylamine and 0.05 ml of tert-butylacetyl chloride followed by stirring at room temperature for 2 hours. The reaction was stopped by a saturated sodium hydrogen carbonate solution and the product was extracted with ethyl acetate followed by drying over sodium sulfate. After the solvent was evaporated in vacuo, the residue was separated and purified by a silica gel thin-layer chromatography (ethyl acetate) and the by a silica gel thin-layer chromatography (chloroform/methanol=10/1) to give 11 mg of the title compound as a white solid.

$^1$HNMR (200 MHz, CDCl$_3$) δ: 0.99-1.13 (9H, m), 2.25-2.38 (2H, m), 2.50-2.76 (2H, m), 3.70-3.93 (2H, m), 4.17-4.33 (2H, m), 6.41-6.62 (1H, m), 7.20-7.51 (3H, m), 7.89-8.02 (2H, m)

ESI-MS Found: m/z 343.2 [M+H]+.

Example 70

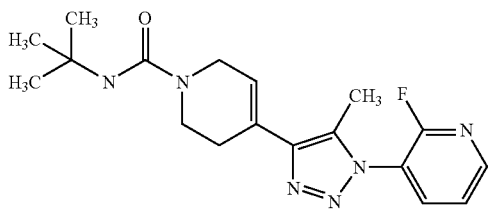

{4-[1-(2-Fluoropyridin-3-yl)-5-methyl-1H-[1,2,3]-triazol-4-yl]-1,2,3,6-tetrahydropyridine-1-carboxylic acid tert-butylamide 1) Production of 4-[1-(2-fluoropyridin-3-yl)-5-methyl-1H-[12,3]triazol-4-yl]-1,2,3,6-tetrahydropyridine Trifluoroacetic acid (3.0 ml) was added to 189 mg of tert-Butyl 4-[1-(2-fluoropyridin-3-yl)-5-methyl-1H-[1,2,3]triazol-4-yl]-1,2,3,6-tetrahydropyridine-1-carboxylate prepared in Example 6 followed by stirring at room temperature for 10 minutes and the solvent was evaporated in vacuo therefrom followed by adding a saturated sodium hydrogen carbonate and chloroform were added thereto. After the organic layer was dried over sodium sulfate, the solvent was evaporated in vacuo to give the title compound as a mixture.

2) Production of {4-[1-(2-Fluoropyridin-3-yl)-5-methyl-1H-[1,2,3]triazol-4-yl]-1,2,3,6-tetrahydropyridine-1-carboxylic acid tert-butylamide Methylene chloride (2 ml), 0.08 ml of triethylamine and 0.04 ml of tert-butyl isocyanate were added to 10 mg of the amine substance prepared in 1) followed by stirring at room temperature for one night. After the solvent was evaporated in vacuo and the residue was separate and purified by a silica gel thin-layer chromatography (ethyl acetate) to give 9 mg of the title compound as a white solid.

$^1$HNMR (300 MHz, CDCl$_3$) δ: 1.39 (9H, s), 2.34 (3H, d, J=2.0 Hz), 2.72-2.81 (2H, m), 3.57-3.63 (2H, m), 4.02-4.08 (2H, m), 4.34 (1H, bes), 6.04-6.11 (1H, m), 7.41-7.49 (1H, m), 7.95-8.05 (1H, m), 8.39-8.45 (1H, m)

ESI-MS Found: m/z 359.3 [M+H]+.

Example 71

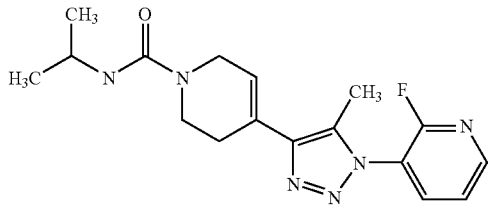

4-[1-(2-Fluoropyridin-3-yl)1H-[1,2,3]triazol-4-yl-1,2,3,6-tetrahydropyridine-1-carboxylic acid isopropylamide To 100 mg of the amine substance prepared in 1) of Example 70 were added 4 ml of methylene chloride, 0.14 ml of triethylamine and 0.2 ml of isopropyl isocyanate followed by stirring at room temperature for 30 minutes. The reaction was stopped by addition of water and the product was extracted with ethyl acetate followed by drying over sodium sulfate. After the solvent was evaporated in vacuo, the residue was separated and purified by a silica gel column chromatography (ethyl acetate) to give 48 mg of the title compound as a white solid.

$^1$HNMR (300 MHz, CDCl$_3$) δ: 1.19 (6H, d, J=6.5 Hz), 2.34 (3H, d, J=1.9 Hz), 2.72-2.82 (2H, m), 3.64 (2H, t, J=5.6 Hz), 3.95-4.12 (3H, m), 4.21-4.31 (1H, m), 6.04-6.12 (1H, m), 7.40-7.50 (1H, m), 7.95-8.06 (1H, m), 8.40-8.47 (1H, m)

ESI-MS Found: m/z 345.2 [M+H]+.

Example 72

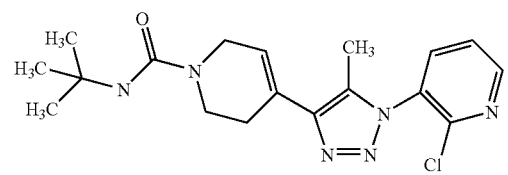

4-[1:2-Chloropyridin-3-yl)1H-[1,2,3]triazol-4-yl]-1,2,3,6-tetrahydropyridine-1-carboxylic acid tert-butylamide The same operation as in Example 70 was carried out using the amine substance prepared in 1) of Example 42 to give the title compound.

$^1$HNMR (300 MHz, CDCl$_3$) δ: 1.39 (9H, s), 2.30 (3H, s), 2.72-2.82 (2H, m), 3.57-3.63 (2H, m), 4.01-4.08 (2H, m), 4.36 (1H, brs), 6.09-6.13 (1H, m), 7.47-7.52 (1H, m), 7.79-7.85 (1H, m), 8.60-8.65 (1H, m)

ESI-MS Found: m/z 357.1 [M+H]+.

Example 73

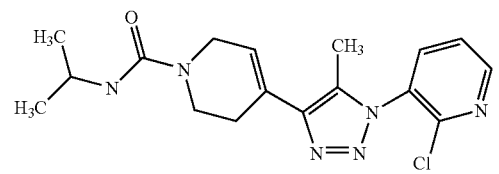

4-[1-(2-Chloropyridin-3-yl)-1H-[112,3]triazol-4-yl]-1,2,3,6-tetrahydropyridine-1-carboxylic acid isopropylamide The same operation as in Example 71 was carried out using the amine substance prepared in 1) of Example 42 to give the title compound.

$^1$HNMR (300 MHz, CDCl$_3$) δ: 1.19 (6H, d, J=6.6 Hz), 2.29 (3H, s), 2.73-2.82 (2H, m), 3.60-3.69 (2H, m), 3.95-4.15 (3H, m), 4.26 (1H, d, J=6.0 Hz), 6.08-6.13 (1H, m), 7.45-7.52 (1H, m), 7.78-7.85 (1H, m), 8.59-8.65 (1H, m)

ESI-MS Found: m/z 361.1 [M+H]+.

Example 74

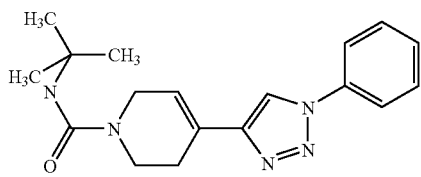

4-[1-Phenyl-1H-[1,2,3]triazol-4-yl]-1,2,3,6-tetra-hydropyridine-1-carboxylic acid tert-butylamide 4-[1-Phenyl-1H-[1,2,3]triazol-4-yl]-1,2,3,6-tetra-hydropyridine (35 mg) prepared in Example 49 was dissolved in 1 ml of pyridine and 1 ml of chloroform and 26 μl of tert-butyl isocyanate was added thereto followed by stirring at room temperature for 6 hours. The reaction solution was concentrated in vacuo and the resulting residue was separated and purified by a preparative thin-layer chromatography (chloroform/methanol=10/1+0.3% aqueous ammonia) and then recrystallized from chloroform-hexane to give 42 mg of the title compound as a white solid.

$^1$HNMR (300 MHz, CDCl$_3$) δ: 1.39 (9H, s), 2.61 (2H, bs), 3.64 (2H, t, J=5.7 Hz), 3.97-4.04 (2H, m), 4.34 (1H, bs), 6.55 (1H, bs), 7.44 (1H, t, J=7.3 Hz), 7.54 (2H, t, J=8.0 Hz), 7.74 (2H, d, J=8.0H), 7.88 (1H, s)

ESI-MS Found: m/z 326.4 [M+H]+.

Example 75

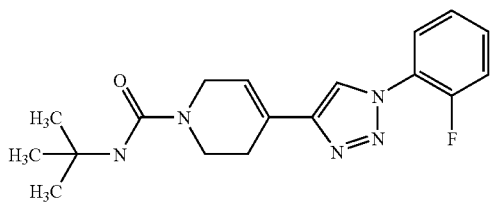

4-[1-(2-Fluorophenyl)-1H-[1,2,3]triazol-4-yl]-1,2,3,6-tetrahydropyridine-1-carboxylic acid tert-butylamide The same operation as in Example 70 was carried out using the amine substance prepared in 1) of Example 46 to give the title compound.

$^1$HNMR (300 MHz, CDCl$_3$) δ: 1.39 (9H, m), 2.53-2.68 (2H, m), 3.58-3.70 (2H, m), 3.93-4.07 (2H, m), 4.35 (1H, brs), 6.50-6.59 (1H, m), 7.20-7.50 (3H, m), 7.91-8.02 (2H, m)

ESI-MS Found: m/z 344.3 [M+H]+.

Example 76

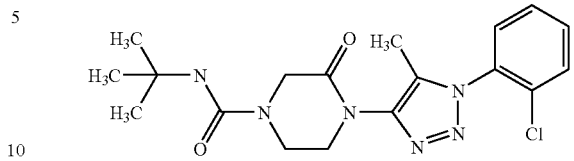

4-[1-(2-Chlorophenyl)-5-methyl-1H-[1,2,3]triazol-4-yl]-3-oxopiperazine-1-carboxylic acid tert-butylamide In a nitrogen atmosphere, 4-[1-(2-chlorophenyl)-5-methyl-1H-[1,2,3]triazol-4-yl]-3-oxopiperazine prepared in 1) of Example 51 was dissolved in 1 ml of chloroform and 0.05 ml of tert-butyl isocyanate and 0.1 ml of triethylamine were added thereto followed by stirring at room temperature for 2 hours. After the solvent was evaporated in vacuo, the resulting residue was purified by a preparative thin-layer silica gel chromatography (chloroform:methanol=9:1) to give 5 mg of the title compound as a white solid.

$^1$HNMR (400 MHz, CDCl$_3$) δ: 1.39 (9H, s), 2.13 (3H, s), 3.83 (2H, t, J=5.4 Hz), 4.04 (2H, t, J=5.4 Hz), 4.17 (2H, s), 4.32 (2H, s), 7.46-7.64 (4H, m)

ESI-MS Found: m/z 391.1 [M+H]+.

Example 77

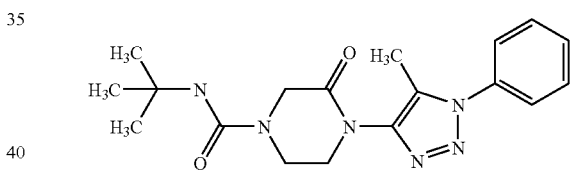

4-(5-Methyl-1-phenyl-1H-[1,2,3]triazol-4-yl)-3-oxo-piperazine-1-carboxylic acid tert-butylamide 1) Production of 4-(5-methyl-1-phenyl-1H-[1,2,3]-triazol-4-yl)-3-oxopiperazine 4N hydrochloric acid/dioxane solution (10 ml) was added to tert-butyl 4-(5-methyl-1-phenyl-1H-[1,2,3]triazol-4-yl)-3-oxopiperazine-1-carboxylate prepared in Example 29 followed by stirring at room temperature for 3 hours and the solvent was evaporated in vacuo to give 60 mg of the title compound as a white solid.

ESI-MS Found: m/z 258.3 [M+H]+.

2) Production of 4-(5-methyl-1-phenyl-1H-[1,2,3]triazol-4-yl)-3-oxo-piperazine-1-carboxylic acid tert-butylamide In a nitrogen atmosphere, 8 mg of the compound prepared in the above 1) was dissolved in 1 ml of chloroform and 0.03 ml of tert-butyl isocyanate and 0.06 ml of triethylamine were added thereto followed by stirring at room temperature for 2 hours. After the solvent was evaporate in vacuo, the resulting residue was purified by a preparative thin-layer silica gel chromatography (chloroform:methanol=9:1) to give 2 mg of the title compound as a white solid.

$^1$HNMR (400 MHz, CDCl$_3$) δ: 1.39 (9H, s), 2.25 (3H, s), 3.82 (2H, t, J=5.2, 10.4 Hz), 3.97-4.02 (2H, m), 4.16 (2H, m), 7.46-7.57 (5H, m)

ESI-MS Found: m/z 357.3 [M+H]+.

Example 78

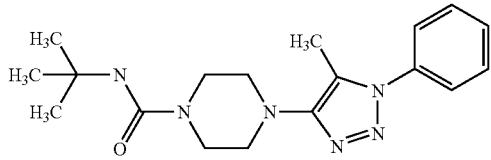

4-(5-Methyl-1-phenyl-1H-[1,2,3]triazol-4-yl)-piperazine-1-carboxylic acid tert-butylamide 4N hydrochloric acid/dioxane solution (3 ml) was added to 1 tert-butyl 4-[5-methyl-1-phenyl-1H-[1,2,3]triazol-4-yl]-piperazine-1-carboxylate prepared in Example 33 followed by stirring at room temperature for 3 hours. The solvent was evaporated in vacuo, the resulting residue was dissolved in 1 ml of chloroform and, in a nitrogen atmosphere, 0.03 ml of tert-butyl isocyanate and 0.06 ml of triethylamine were added thereto followed by stirring at room temperature for one night. After the solvent was evaporate in vacuo, the resulting residue was purified by a preparative thin-layer silica gel chromatography (chloroform:methanol=9:1) to give 2 mg of the title compound as a white solid.

$^1$HNMR (400 MHz, CDCl$_3$) δ: 1.38 (9H, s), 2.26 (3H, s), 3.20 (4H, t, J=5.0 Hz), 3.48 (4H, t, J=5.2 Hz), 7.41-7.55 (5H, m)

ESI-MS Found: m/z 343.4 [M+H]+.

Example 79

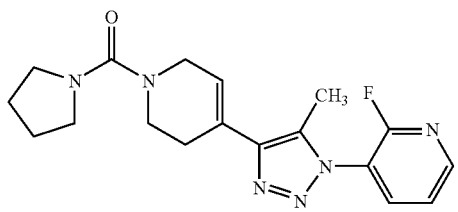

{4-[1-(2-Fluoropyridin-3-yl)-5-methyl-1H-[1,2,3]-triazol-4-yl]-1,2,3,6-tetrahydropyridine-1-carboxylic acid pyrrolidineamide To 5.0 mg of the amine substance prepared in 1) of Example 70 were added 1 ml of methylene chloride, 0.05 ml of triethylamine and 0.02 ml of 1-pyrrolidinecarbonyl chloride followed by stirring at room temperature for 5 minutes. After the solvent was evaporated in vacuo, the residue was separated and purified by a silica gel thin-layer chromatography (ethyl acetate) to give 1.5 mg of the title compound as a colorless amorphous substance.

$^1$HNMR (300 MHz, CDCl$_3$) δ: 1.77-1.92 (4H, m), 2.34 (3H, d, J=2.0 Hz), 2.72-2.83 (2H, m), 3.34-3.58 (6H, m), 3.96-4.03 (2H, m), 6.02-6.12 (1H, m), 7.40-7.49 (1H, m), 7.94-8.05 (1H, m), 8.37-8.43 (1H, m)

ESI-MS Found: m/z 357.1 [M+H]+.

Example 80

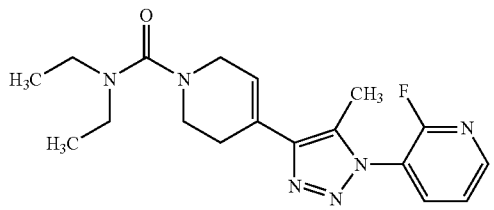

4-[1-(2-Fluoropyridin-3-yl)-5-methyl-1H-[1,2,3]-triazol-4-yl]-1,2,3,6-tetrahydropyridine-1-carboxylic acid diethylamide To 5.0 mg of the amine substance prepared in 1) of Example 70 were added 1 ml of methylene chloride, 0.05 ml of triethylamine and 0.02 ml of diethylcarbamoyl chloride followed by stirring at room temperature for 5 minutes. After the solvent was evaporated in vacuo, the residue was separated and purified by a silica gel thin-layer chromatography (ethyl acetate) to give 2.9 mg of the title compound as a colorless amorphous substance.

$^1$HNMR (300 MHz, CDCl$_3$) δ: 1.16 (6H, t, J=7.1 Hz), 2.35 (3H, d, J=2.1 Hz), 2.75-2.85 (2H, m), 3.26 (4H, q, J=7.1 Hz), 3.42-3.50 (2H, m), 3.91-4.00 (2H, m), 6.09-6.15 (1H, m), 7.41-7.49 (1H, m), 7.95-8.05 (1H, m), 8.38-8.45 (1H, m)

ESI-MS Found: m/z 359.2 [M+H]+.

Example 81

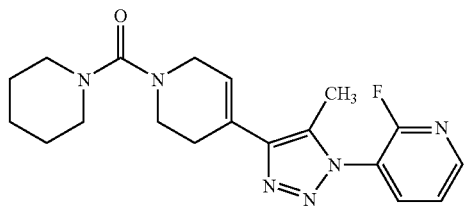

4-[1-(2-Fluoropyridin-3-yl)-5-methyl-1H-[1,2,3]-triazol-4-yl]-1,2,3,6-tetrahydropyridine-1-carboxylic acid piperidineamide The same operation as in Example 80 was carried out using the amine substance prepared in 1) of Example 70 and 1-piperidinecarbonyl chloride.

$^1$HNMR (300 MHz, CDCl$_3$) δ: 1.51-1.68 (6H, m), 2.35 (3H, d, J=2.0 Hz), 2.76-2.82 (2H, m), 3.18-3.30 (4H, m), 3.44-3.52 (2H, m), 3.92-4.02 (2H, m), 6.08-6.13 (1H, m), 7.40-7.45 (1H, m), 7.92-8.05 (1H, m), 8.38-8.44 (1H, m)

ESI-MS Found: m/z 371.3 [M+H]+.

Example 82

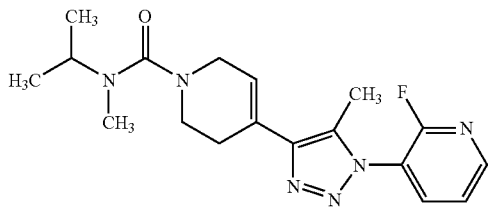

4-[1-(2-Fluoropyridin-3-yl)-5-methyl-1H-[1,2,3]-triazol-4-yl]-1,2,3,6-tetrahydropyridine-1-carboxylic acid isopropylmethylamide 4-[1-(2-Fluoropyridin-3-yl)1H-[1,2,3]triazol-4-yl]-1,2,3,6-tetrahydropyridine-1-carboxylic acid isopropylamide (15 mg) prepared in Example 71 was dissolved in 2 ml of dimethylformamide, cooled down to 0° C., 50 mg of 60% sodium hydride and 0.2 ml of methyl iodide were added thereto and the temperature of mixture was raised up to room temperature and stirred for one night. The reaction was stopped by addition of water, the product was extracted with ethyl acetate and dried over sodium sulfate and the solvent was evaporated. The resulting residue was separated and purified by a silica gel thin-layer chromatography (ethyl acetate) to give 8.4 mg of the title compound as a white solid.

$^1$HNMR (300 MHz, CDCl$_3$) δ: 1.17 (6H, d, J=6.7 Hz), 2.35 (3H, d, J=1.9 Hz), 2.74 (3H, s), 2.74-2.85 (2H, m), 3.40-3.50 (2H, m), 3.90-3.99 (2H, m), 4.10 (1H, sept, J=6.7 Hz), 6.08-6.15 (1H, m), 7.40-7.50 (1H, m), 7.95-8.05 (1H, m), 8.38-8.45 (1H, m)

ESI-MS Found: m/z 359.3 [M+H]+.

Example 83

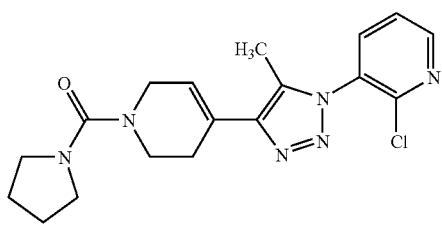

{4-[1-(2-Chloropyridin-3-yl)-5-methyl-1H-[1,2,3]-triazol-4-yl]-1,2,3,6-tetrahydropyridine-1-carboxylic acid pyrrolidineamide Reaction was carried out by the same method as in Example 59 using 1-pyrrolidinecarbamyl chloride in place of 2-methoxyethyl chloroformate used in Example 59 to give the title compound.

$^1$HNMR (400 MHz, CDCl$_3$) δ: 1.83-1.87 (4H, m), 2.29 (3H, s), 2.80 (2H, br), 3.40-3.43 (2H, m), 3.53 (2H, t, J=5.6 Hz), 4.00-4.01 (2H, m), 6.10 (1H, br), 7.47 (1H, dd, J=4.8, 8.0 Hz), 7.80 (1H, dd, J=1.6, 8.0 Hz), 8.60 (1H, dd, J=1.6, 4.8 Hz)

ESI-MS Found: m/z 373.2 [M+H]+.

Example 84

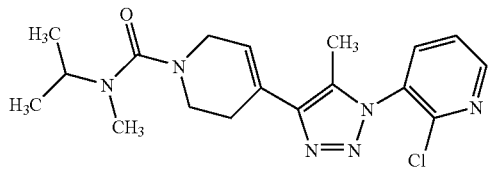

4-[1-(2-Chloropyridin-3-yl)-1H-[1,2,3]triazol-4-yl]-1,2,3,6-tetrahydropyridine-1-carboxylic acid isopropyl-methylamide The same operation as in Example 82 was carried out using 4-[1-(2-chloropyridin-3-yl)-1H-[1,2,3]triazol-4-yl]-1,2,3,6-tetrahydropyridine-1-carboxylic acid isopropylamide prepared in Example 73 to give the title compound.

$^1$HNMR (300 MHz, CDCl$_3$) δ: 1.17 (6H, d, J=6.8 Hz), 2.30 (3H, s), 2.74 (3H, d, J=1.0 Hz), 2.77-2.89 (2H, m), 3.41-3.50 (2H, m), 3.90-3.99 (2H, m), 4.01-4.17 (1H, m), 6.10-6.17 (1H, m), 7.45-7.52 (1H, m), 7.78-7.83 (1H, m), 8.59-8.65 (1H, m)

ESI-MS Found: m/z 375.2 [M+H]+.

Example 85

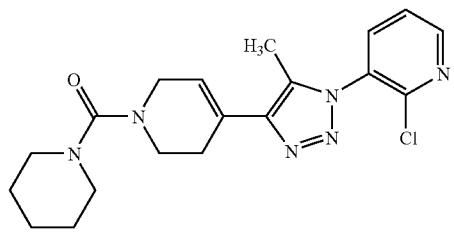

4-[1-(2-Chloropyridin-3-yl)-5-methyl-1H-[1,2,3]-triazol-4-yl]-1,2,3,6-tetrahydropyridine-1-carboxylic acid piperidineamide Reaction was carried out by the same method as in Example 59 using 1-piperidinecarbamyl chloride in place of 2-methoxyethyl chloroformate used in Example 59 to give the title compound.

$^1$HNMR (400 MHz, CDCl$_3$) δ: 1.60-1.62 (6H, m), 2.77 (3H, s), 2.80-2.81 (2H, br), 3.23-3.25 (4H, m), 3.48 (2H, t, J=6.0 Hz), 3.97 (2H, t, J=2.8 Hz), 6.11 (1H, br), 7.47 (1H, dd, J=4.8, 8.0 Hz), 7.80 (1H, dd, J=1.6, 8.0 Hz), 8.60 (1H, dd, J=1.6, 4.8 Hz)

ESI-MS Found: m/z 387.2 [M+H]+.

Example 86

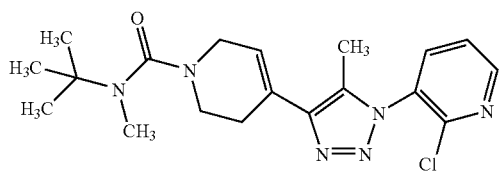

4-[1-(2-Chloropyridin-3-yl)-5-methyl-1H-[1,2,3]-triazol-4-yl]-1,2,3,6-tetrahydropyridine-1-carboxylic acid methyl tert-butylamide The same operation as in Example 82 was carried out using 4-[1-(2-chloropyridin-3-yl)-1H-[1,2,3]triazol-4-yl]-1,2,3,6-tetrahydropyridine-1-carboxylic acid tert-butylamide prepared in Example 72 to give the title compound.

$^1$HNMR (300 MHz, CDCl$_3$) δ: 1.39 (9H, s), 2.30 (3H, s), 2.75-2.85 (5H, m), 3.50-3.58 (2H, m), 3.99-4.05 (2H, m), 6.10-6.16 (1H, m), 7.45-7.52 (1H, m), 7.78-7.85 (1H, m), 8.60-8.66 (1H, m)

ESI-MS Found: m/z 389.2 [M+H]+.

Example 87

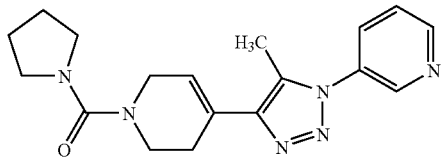

{4-[5-Methyl-1-(pyridin-3-yl)-1H-[1,2,3]-triazol-4-yl]-3,6-dihydro-2H-pyridine}-1 carboxylic acid pyrrolidine-amide In a nitrogen atmosphere, 4-[1-(pyridin-3-yl)-1H-[1,2,3]-triazol-4-yl]-1,2,3,6-tetrahydropyridine (3 mg) prepared in 1) of Example 44 was dissolved in 1 ml of chloroform and 0.03 ml of 1-pyrrolidinecarbonyl chloride and 0.60 ml of triethylamine were added followed by stirring at room temperature for 2 hours. After the solvent was evaporated in vacuo, the resulting residue was purified by a preparative thin-layer silica gel chromatography (chloroform:methanol=9:1) to give 2 mg of the title compound as a white solid.

$^1$HNMR (400 MHz, CDCl$_3$) δ: 1.80-1.90 (4H, m), 2.42 (3H, s), 2.75-2.85 (2H, m), 3.38-3.48 (4H, m), 3.53 (2H, t, J=5.4 Hz), 3.98-4.04 (2H, m), 6.03-6.08 (1H, m), 7.52 (1H, q, J=5.0, 8.2 Hz), 7.58 (1H, dt, J=1.2, 8.4 Hz), 8.73-8.80 (2H, m)

ESI-MS Found: m/z 339.3 [M+H]+.

Example 88

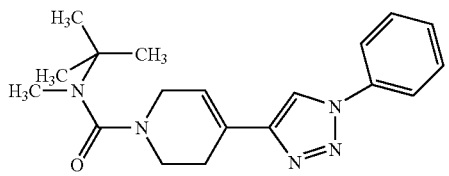

4-[1-Phenyl-1H-[1,2,3]triazol-4-yl]-1,2,3,6-tetrahydropyridine-1-carboxylic acid methyl tert-butylamide 4-[1-Phenyl-1H-[1,2,3]triazol-4-yl]-1,2,3,6-tetra-hydropyridine-1-carboxylic acid tert-butylamide (15 mg) prepared in Example 74 was added to a solution of 35 mg of potassium hydride in 1 ml of tetrahydrofuran washed with hexane. After stirring at room temperature for 10 minutes, 20 μl of methyl iodide was added thereto and the mixture was stirred at room temperature for 30 minutes. Water was added to the reaction solution followed by extracting with chloroform. The resulting organic layer washed with a saturated aqueous solution of sodium bicarbonate and then with a saturated saline solution, dried over sodium sulfate and the solvent was evaporated in vacuo. The resulting residue was separated and purified by a preparative thin-layer chromatography (chloroform/methanol=20/1+0.3% aqueous ammonia) to give 8.5 mg of the title compound as a white solid $^1$HNMR (300 MHz, CDCl$_3$) δ: 1.33 (9H, s), 2.63 (2H, bs), 2.80 (3H, s), 3.54 (2H, t, J=5.6 Hz), 3.97-4.04 (2H, m), 6.55 (1H, bs), 7.44 (1H, t, J=7.2 Hz), 7.53 (2H, t, J=7.9 Hz), 7.74 (2H, d, J=7.8H), 7.87 (1H, s)

ESI-MS Found: m/z 340.2 [M+H]+.

Example 89

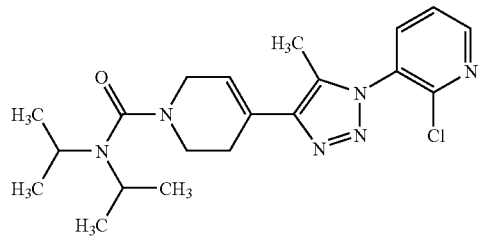

4-[1-(2-Chloropyridin-3-yl)-5-methyl-1H-[1,2,3]-triazol-4-yl]-1,2,3,6-tetrahydropyridine-1-carboxylic acid diisopropylamide Reaction was carried out by the same method as in Example 59 using diisopropylcarbamyl chloride in place of 2-methoxyethyl chloroformate used in Example 59 to give the title compound.

$^1$HNMR (400 MHz, CDCl$_3$) δ: 1.30 (12H, d, J=7.2 Hz), 2.30 (3H, s), 2.81 (2H, br), 3.36 (2H, t, J=5.6 Hz), 3.66 (2H, quintet, J=7.2 Hz), 3.84 (2H, br), 6.13 (1H, br), 7.47 (1H, dd, J=4.8, 8.0 Hz), 7.80 (1H, dd, J=1.6, 8.0 Hz), 8.60 (1H, dd, J=1.6, 4.8 Hz)

ESI-MS Found: m/z 403.2 [M+H]+.

Example 90

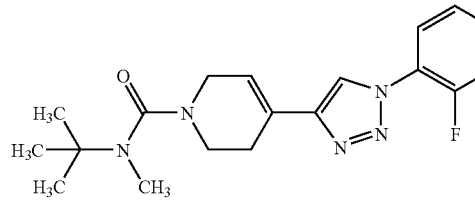

4-[1-(2-Fluorophenyl)-1H-[1,23]triazol-4-yl]-1,2,36-tetrahydropyridine-1-carboxylic acid methyl tert-butylamide 4-[1-(2-Fluorophenyl)-1H-[1,2,3]triazol-4-yl]-1,2,3,6-tetrahydropyridine-1-carboxylic acid tert-butylamide (33 mg) prepared in Example 75 was dissolved in 1.0 ml of N,N- dimethylformamide and 15 mg of sodium hydride and 0.02 ml of methyl iodide were added thereto followed by stirring for one night. Water was added to the reaction solution, the mixture was extracted with ethyl acetate and the ethyl acetate layer washed with a saturated saline solution and dried over sodium sulfate. After the solvent was evaporated in vacuo and the residue was separated and purified by a silica gel column chromatography (hexane/ethyl acetate=3/2) to give 17.4 mg of the title compound as a white solid.

$^1$HNMR (400 MHz, CDCl$_3$) δ: 1.33 (9H, s), 2.62-2.64 (2H, m), 2.80 (3H, s), 3.53 (2H, t, J=5.86 Hz), 4.00 (2H, q, J=2.93 Hz), 6.55 (1H, t, J=1.46 Hz), 7.32-7.33 (2H, m), 7.39-7.45 (2H, m), (1H, dt, J=1.46, 6.96 Hz)

ESI-MS Found: m/z 358.3 [M+H]+.

Examples of the pharmacological tests using the compounds of the present invention as test compounds will be shown as follows.

Pharmacological Test Example 1 mGluR1-Inhibiting Action mGluR1-iiihibiting action was measured using the compounds of the present invention mentioned in Examples 42, 43 and 82.

(Cell Culture)

cDNA of human metabotropic glutamic acid receptor 1a (mGluR1a) was transfected to CHO cells using Lipofectamine (manufactured by Gibco BRL) to give a strain which stably expresses mGluR1a. The CHO cells in which mGluR1a was expressed were incubated in a DMEM medium containing 10% of dialyzed fetal bovine serum, 1% of proline, 100 units/ml of penicillin, 0.1 mg/ml of streptomycin sulfate and 2 mM of glutamine.

(Measurement of Calcium Concentration in the Cells)

On the day before the measurement, 4 μM Fluo-3 was incubated in a CO$_2$ incubator for 1 hour to the CHO cells where mGluR1a was expressed being plated with 50,000 cells per well of a 96-well black plate (View Plate manufactured by Packard). After that, the cells were washed for four times with an HBSS solution containing 20 mM of HEPES and 2.5 mM of Probenecid and then calcium concentration in the cells was measured using a Fluorescence Imaging Plate Reader (FLIPR, manufactured by Molecular Device). Incidentally, the test compound and glutamic acid were prepared using an HBSS solution containing 20 mM HEPES and 2.5 mM Probenecid. The test compound was added before 5 minutes of the stimulation with an agonist and, with regard to the agonist, 10 μM glutamic acid was used.

The result was that the compounds of the present invention mentioned in the following Table 1 did not show an agonistic property until 10 μM to mGluR1. A rise in calcium raised by 10 μM glutamic acid was suppressed in a dose-dependent manner. The IC$_{50}$ values are shown in Table 1.

TABLE 1

|  | IC$_{50}$ (nM) |
| --- | --- |
| Example 42 | 6.7 |
| Example 43 | 6.8 |
| Example 82 | 6.3 |

A model where autonomic motility increases by administration of methamphetamine and a model where pre-pulse inspiration lowers have been known as animal models where known antipsychotic agents such as haloperidol and risperidone show an action.

In both test systems, action of drugs having an mGluR1 antagonistic action was investigated.

Pharmacological Test Example 2

Suppressive Action of the Compound to Autonomic Momentum in Mice which Increases by Methamphetamine Male ICR (CD-1) mice (20 to 40 g) were used and behavior quantity was measured using a behavior quantity measuring device (manufactured by Neuroscience) where movement of animals is perceived by an infrared sensor. A compound or an appropriate solvent was administered to a mouse and, after 30 minutes, a physiological saline solution or methamphetamine was administered. Behavior quantities immediately after that and until 60 minutes thereafter were measured. Difference between the behavior quantity of the methamphetamine-administered group and that of the solvent-administered group during the measuring period was defined as 100% and evaluation was conducted by expressing the inhibitory % in behavior quantity of the test-compound-administered group. By a subcutaneous administration of methamphetamine (2 mg/kg), the behavior quantity during 60 minutes after the administration significantly increased. When a compound (10 mg/kg) having an mGluR1-inhibiting action according to the present invention was intraperitoneally administered 30 minutes before administration of methamphetamine, an increase in behavior quantity by methamphetamine was clearly suppressed. The result is shown in Table 1.

From the above result, it has been found that the compound of the present invention shows a strong antagonistic action on methamphetamine.

TABLE 2

| Compounds of Examples | Motility Quantity (Suppressive %) |
| --- | --- |
| Example 42 | >80% |
| Example 43 | >80% |
| Example 84 | >80% |

Pharmacological Test Example 3

Suppressive Action of the Compound to Pre-Pulse Inhibition which Decreases by Methamphetamine)

Investigation was also carried out in a test system of a pre-pulse inhibition where action of antipsychotic agents is able to be specifically detected. A startle reaction being stimulated by combining sonic stimulations of 63.66 and 72 dB (pre-pulse) prior to pulse stimulation and startle reaction to sonic stimulation of 120 dB (pulse stimulation) in the presence of a back sound of 60 dB was measured using a startle reaction measuring device which perceives the body movement of rats (manufactured by San Diego Instrument). The compound of the present invention or an appropriate solvent was administered to a rat and, after 30 minutes, a physiological saline solution of 3 mg/kg of methamphetamine was administered whereupon measurement of a startle reaction was carried out. The startle reactions upon the pulse stimulation and in the presence of pre-pulse were defined as A and B, respectively and values of pre-pulse inhibition (hereinafter, referred to as PPI) were calculated from the following formula.

Method for calculation of PPI:

$$PPI(\%) = 100 \times (A-B)/A$$

To a startle reaction to pulse stimulation, about 50% attenuation was noted in the startle reaction in the presence of the anteceding pre-pulse of 72 dB (pre-pulse inhibition). When a pre-treatment with methamphetamine was conducted, the startle reaction attenuated to an extent of only about 20% whereby a reduction in pre-pulse inhibition was noted. In the present model, lowering of pre-pulse inhibition by methamphetamine tends to be recovered when a compound having an mGluR1 antagonistic action was orally administered (1 to 10 mg/kg) 30 minutes before the administration of methamphetamine. The result where the compound showed a significant suppressive action on PPI which decreased by methamphetamine is shown in the following Table 3.

From the result as such, it has been noted that the compound of the present invention recovers the PPI disorder induced by methamphetamine.

TABLE 3

| Compounds of Examples | Inhibition Effect to PPI Disorder |
|---|---|
| Example 42 | yes |
| Example 43 | yes |
| Example 82 | yes |

From the results of the above Pharmacological Test Examples 2 and 3, it has been confirmed that the compound of the present invention having an mGluR1 inhibition has an action similar to a treating agent for schizophrenia in animal models in which a treating agent for schizophrenia such as haloperidol and risperidone has an action.

Accordingly, the compound of the present invention having an mGluR1 antagonistic action is a medicament useful as treatment and/or prevention of schizophrenia.

INDUSTRIAL APPLICABILITY

In accordance with the present invention, a novel substance having an mGluR1 inhibiting action is provided.

Diaryl-substituted five-membered heterocyclic derivative represented by the formula (I) provided by the present invention or a pharmaceutically acceptable salt thereof has a powerful mGluR1 inhibiting action and is useful as prevention or treatment of convulsion, acute pain, inflammatory pain or chronic pain, cerebral disturbance such as cerebral infarction or transient cerebral ischemia onset, pathergasia such as schizophrenia, anxiety, chemical dependency, Parkinson's disease or gastrointestinal disorder.

The invention claimed is:

1. A compound of the formula (I):

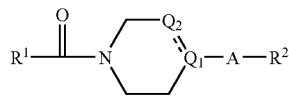

(I)

wherein:
R$^1$ is
(A) a linear or branched alkoxy group, a cycloalkoxy group or a linear or branched lower alkyl group, or
(B) a formula (II):

(II)

wherein:
R$^3$ and R$^4$ each independently is a hydrogen atom, a linear or branched lower alkyl group or a cycloalkyl group or R$^3$, R$^4$ and nitrogen atom in the formula (II) together form a pyrrolidine or a piperidine ring;
R$^2$ is a pyridyl group, which may have one to three substituent(s) selected from the group consisting of halogen atom, a lower alkyl group, cyano group, nitro group, an alkoxy group, a lower alkylsulfonyl group, oxo group and hydroxyl group;
Q$_1$ is carbon atom atom;
Q$_2$ is carbon atom which is unsubstituted or substituted with an oxo group;
the formula (III):

-------- (III)

is a single bond or a double bond;
A is a group of the formula (IV-5):

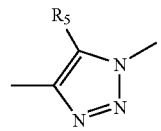 or 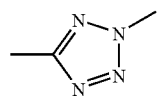

(IV-5)

wherein:
R$^5$ is hydrogen atom, a lower alkyl group, a cyano group, an alkoxy group or a trialkylsilyl group, wherein the lower alkyl group may be substituted with an alkoxy group;
or a pharmaceutically acceptable salt thereof.

2. The compound of claim 1 wherein R$^1$ is a group of the formula (II):

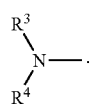

(II)

3. The compound of claim 1 wherein R$^1$ is a group of the formula (II):

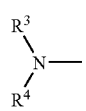

(II)

and where R$^3$, R$^4$ and nitrogen atom in the formula (II) together form a pyrrolidine ring.

4. The compound of claim 1 wherein R$^1$ is a group of the formula (II):

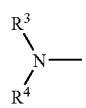

(II)

and where R$^3$, R$^4$ and nitrogen atom in the formula (II) together form a piperidine ring.

5. The compound of claim 1 wherein the six-membered ring formed by $Q_1$, $Q_2$ and the carbon and nitrogen atoms to which they are attached is:

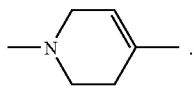

6. A compound which is selected from the group consisting of:
   isopropyl 4-[1-(2-fluoropyridin-3-yl)-5-methyl-1H-[1,2,3]triazol-4-yl]-1,2,3,6-tetrahydropyridine-1-carboxylate,
   4-[1-(2-fluoropyridin-3-yl)-5-methyl-1H-[1,2,3,]triazol-4-yl]-1,2,3,6-tetrahydropyridine-1-carboxylic acid pyrrolidineamide,
   4-[1-(2-fluoropyridin-3-yl)-5-methyl-1H-[1,2,3,]triazol-4-yl]-1,2,3,6-tetrahydropyridine-1-carboxylic acid diethylamide,
   4-[1-(2-fluoropyridin-3-yl)-5-methyl-1H-[1,2,3,]triazol-4-yl]-1,2,3,6-tetrahydropyridine-1-carboxylic acid piperidineamide,
   4-[1-(2-fluoropyridin-3-yl)-5-methyl-1H-[1,2,3]triazol-4-yl]-1,2,3,6-tetrahydropyridine-1-carboxylic acid isopropylmethylamide,
   4-[1-(2-fluoropyridin-3-yl)-5-methyl-1H-[1,2,3]triazol-4-yl]-1,2,3,6-tetrahydropyridine-1-carboxylic acid tert-butylamide,
   isopropyl 4-[1-(2-chloropyridin-3-yl)-5-methyl-1H-[1,2,3]triazol-4-yl]-1,2,3,6-tetrahydropyridine-1-carboxylate,
   isopropyl 4-[1-(2-fluoropyridin-5-yl)-5-methyl-1H-[1,2,3]triazol-4-yl]-1,2,3,6-tetrahydropyridine-1-carboxylate,
   propyl 4-[1-(2-chloropyridin-3-yl)-5-methyl-1H-[1,2,3]triazol-4-yl]-1,2,3,6-tetrahydropyridine-1-carboxylate,
   ethyl 4-[1-(2-chloropyridin-3-yl)-1H-[1,2,3]triazol-4-yl]-1,2,3,6-tetrahydropyridine-1-carboxylate,
   2-methylpropyl 4-[1-(2-chloropyridin-3-yl)-5-methyl-1H-[1,2,3]triazol-4-yl]-1,2,3,6-tetrahydropyridine-1-carboxylate,
   isopropyl 4-[1-(pyridin-3-yl)-1H-[1,2,3]triazol-4-yl]-1,2,3,6-tetrahydropyridine-1-carboxylate,
   {4-[1-(2-chloropyridin-3-yl)-5-methyl-1H-[1,2,3]triazole-4-yl]-1,2,3,6-tetrahydropyridine-1-carboxylic acid pyrrolidineamide,
   4-[1-(2-fluoro-pyridin-3-yl)-1H-[1,2,3]triazol-4-yl]-1,2,3,6-tetrahydropyridine-1-carboxylic acid isopropylamide,
   4-[1-(2-chloro-pyridin-3-yl)-1H-[1,2,3]triazol-4-yl]-1,2,3,6-tetrahydropyridine-1-carboxylic acid isopropylmethylamide,
   4-[1-(2-chloropyridin-3-yl)-5-methyl-1H-[1,2,3]triazol-4-yl]-1,2,3,6-tetrahydropyridine-1-carboxylic acid piperidineamide,
   4-[1-(2-chloropyridin-3-yl)-5-methyl-1H-[1,2,3]triazol-4-yl]-1,2,3,6-tetrahydropyridine-1-carboxylic acid methyl-tert-butylamide,
   4-[1-(2-chloropyridin-3-yl)-1H-[1,2,3]triazol-4-yl]-1,2,3,6-tetrahydropyridine-1-carboxylic acid tert-butylamide,
   1-{4-[1-(2-chloropyridin-3-yl)-1H-[1,2,3]triazol-4-yl]-1,2,3,6-tetrahydropyridin-1-yl}-3-methyl-1-butanone,
   and isopropyl 4-[1-(2-fluoropyridin-3-yl)-1H-[1,2,3]triazol-4-yl]-1,2,3,6-tetrahydropyridine-1-carboxylate,
   or a pharmaceutically acceptable salt thereof.

7. A pharmaceutical composition comprising an inert carrier and the compound of claim 1 or a pharmaceutically acceptable salt thereof.

8. A pharmaceutical composition comprising an inert carrier and the compound of claim 6 or a pharmaceutically acceptable salt thereof.

* * * * *